US012150722B2

United States Patent
Farritor et al.

(10) Patent No.: US 12,150,722 B2
(45) Date of Patent: Nov. 26, 2024

(54) SURGICAL ROBOT POSITIONING SYSTEM AND RELATED DEVICES AND METHODS

(71) Applicant: Virtual Incision Corporation, Lincoln, NE (US)

(72) Inventors: Shane Farritor, Lincoln, NE (US); Nathan Wood, Lincoln, NE (US); Rachael Wagner, Lincoln, NE (US); Parker Durham, Lincoln, NE (US); Lou Cubrich, Lincoln, NE (US); Jay Carlson, Lincoln, NE (US); Mark Reichenbach, Lincoln, NE (US); Robert M. Cicerchia, Westwood, MA (US); Carsten Horn, Fall River, MA (US)

(73) Assignee: Virtual Incision Corporation, Lincoln, NE (US)

( * ) Notice: Subject to any disclaimer, the term of this patent is extended or adjusted under 35 U.S.C. 154(b) by 640 days.

(21) Appl. No.: 17/368,255

(22) Filed: Jul. 6, 2021

(65) Prior Publication Data
US 2022/0000569 A1    Jan. 6, 2022

Related U.S. Application Data

(60) Provisional application No. 63/048,620, filed on Jul. 6, 2020.

(51) Int. Cl.
*A61B 34/30* (2016.01)
*A61G 13/10* (2006.01)
(Continued)

(52) U.S. Cl.
CPC ............ *A61B 34/30* (2016.02); *A61G 13/101* (2013.01); *B25J 9/02* (2013.01); *B25J 9/1035* (2013.01);
(Continued)

(58) Field of Classification Search
CPC .............. A61B 34/30; A61B 2034/302; A61B 2034/303; A61B 2034/305; A61G 13/101; B25J 9/02; B25J 9/1035; B25J 18/007
See application file for complete search history.

(56) References Cited

U.S. PATENT DOCUMENTS 3,870,264 A    3/1975 Robinson
3,989,952 A    11/1976 Timberlake et al.
(Continued)

FOREIGN PATENT DOCUMENTS

CN        102821918      12/2012
DE      102010040405       3/2012
(Continued)

OTHER PUBLICATIONS

Phee et al., "Analysis and Development of Locomotion Devices for the Gastrointestinal Tract," IEEE Transaction on Biomedical Engineering, vol. 49, No. 6, Jun. 2002, pp. 613-616.
(Continued)

*Primary Examiner* — Kira Nguyen
(74) *Attorney, Agent, or Firm* — Fredrikson & Byron, P.A.

(57) ABSTRACT

The various embodiments disclosed herein relate to surgical robot positioning systems and devices that aid in the gross positioning of surgical devices during surgical procedures. For example, a gross positioning system for use with a robotic surgical device may include a positioning body, a yaw mechanism operably coupled to the positioning body at a yaw rotational joint, a pitch mechanism operably coupled to the positioning body at a pitch rotational joint, and a plunge mechanism operably coupled to the pitch mechanism, where the plunge mechanism is configured to slide and to be coupleable to the robotic surgical device.

20 Claims, 36 Drawing Sheets

(51) Int. Cl.
  *B25J 9/02* (2006.01)
  *B25J 9/10* (2006.01)
(52) U.S. Cl.
  CPC ... *A61B 2034/302* (2016.02); *A61B 2034/303* (2016.02); *A61B 2034/305* (2016.02)

(56) References Cited

U.S. PATENT DOCUMENTS

| | | |
|---|---|---|
| 4,246,661 A | 1/1981 | Pinson |
| 4,258,716 A | 3/1981 | Sutherland |
| 4,278,077 A | 7/1981 | Mizumoto |
| 4,538,594 A | 9/1985 | Boebel et al. |
| 4,568,311 A | 2/1986 | Miyaki |
| 4,623,183 A | 11/1986 | Aomori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,922,782 A | 5/1990 | Kawai |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,441,494 A | 1/1995 | Oritz |
| 5,388,528 A | 2/1995 | Pelrine et al. |
| 5,436,542 A | 7/1995 | Petelin et al. |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,497,651 A | 3/1996 | Matter et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,380 A | 4/1997 | Takayama et al. |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyaman et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,792,663 A | 8/1998 | Fry et al. |
| 5,797,538 A | 8/1998 | Heaton et al. |
| 5,797,900 A | 8/1998 | Madhani et al. |
| 5,807,377 A | 9/1998 | Madhani et al. |
| 5,808,665 A | 9/1998 | Green |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,910,129 A | 6/1999 | Koblish et al. |
| 5,911,036 A | 6/1999 | Wright et al. |
| 5,971,976 A | 10/1999 | Wang et al. |
| 5,993,467 A | 11/1999 | Yoon |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,086,529 A | 7/2000 | Arndt |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,139,563 A | 10/2000 | Cosgrove, III et al. |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,307,447 B1 | 10/2001 | Barber et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,382,885 B2 | 5/2002 | Isaksson |
| 6,388,528 B1 | 5/2002 | Buer et al. |
| 6,394,998 B1 | 5/2002 | Wallace et al. |
| 6,398,726 B1 | 6/2002 | Ramans et al. |
| 6,400,980 B1 | 6/2002 | Lemelson |
| 6,408,224 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,458,131 B1 | 10/2002 | Ray |
| 6,458,583 B1 | 10/2002 | Bruhn et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |

(56) References Cited

U.S. PATENT DOCUMENTS

| | | |
|---|---|---|
| 6,491,701 B2 | 12/2002 | Nemeyer et al. |
| 6,493,608 B1 | 12/2002 | Niemeyer et al. |
| 6,496,099 B2 | 12/2002 | Wang et al. |
| 6,497,651 B1 | 12/2002 | Kan et al. |
| 6,508,413 B2 | 1/2003 | Bauer et al. |
| 6,512,345 B2 | 1/2003 | Borenstein |
| 6,515,478 B1 | 2/2003 | Wicklow et al. |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,562,448 B1 | 5/2003 | Chamberlain et al. |
| 6,565,554 B1 | 5/2003 | Niemeyer |
| 6,574,355 B2 | 6/2003 | Green |
| 6,587,750 B2 | 7/2003 | Gerbi et al. |
| 6,588,442 B2 | 7/2003 | Babin |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,624,398 B2 | 9/2003 | Sherrill et al. |
| 6,632,761 B1 | 10/2003 | Ushita et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,657,584 B2 | 12/2003 | Cavallaro et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byrne et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,736,821 B2 | 5/2004 | Squires et al. |
| 6,746,443 B1 | 6/2004 | Morley et al. |
| 6,754,741 B2 | 6/2004 | Alexander et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B2 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,791,231 B2 | 9/2004 | Chang |
| 6,792,135 B1 | 9/2004 | Toyama |
| 6,792,663 B2 | 9/2004 | Krzyzanowski |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,815,640 B1 | 11/2004 | Spear et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,845,646 B2 | 1/2005 | Goto |
| 6,852,107 B2 | 2/2005 | Wang et al. |
| 6,855,583 B1 | 2/2005 | Krivokapic et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tierney et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,878,783 B2 | 4/2005 | Yeager et al. |
| 6,879,880 B2 | 4/2005 | Nowlin et al. |
| 6,892,112 B2 | 5/2005 | Wang et al. |
| 6,895,417 B2 | 5/2005 | Obara et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,036 B2 | 6/2005 | Douk et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,166,113 B2 | 1/2007 | Arambula et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |

(56) References Cited

U.S. PATENT DOCUMENTS

| | | |
|---|---|---|
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,588,537 B2 | 9/2009 | Bass |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,672,168 B2 | 3/2010 | Tanaka et al. |
| 7,678,043 B2 | 3/2010 | Gilad |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,799,088 B2 | 9/2010 | Geitz |
| 7,865,266 B2 | 1/2011 | Moll et al. |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,182,469 B2 | 5/2012 | Anderson et al. |
| 8,231,510 B2 | 7/2012 | Abdo |
| 8,231,610 B2 | 7/2012 | Jo et al. |
| 8,353,897 B2 | 1/2013 | Doyle et al. |
| 8,604,742 B2 | 12/2013 | Farritor et al. |
| 9,089,353 B2 | 7/2015 | Farritor et al. |
| 9,649,020 B2 | 5/2017 | Finlay |
| 11,357,595 B2 | 6/2022 | Reichenbach et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0013601 A1 | 1/2002 | Nobles et al. |
| 2002/0026186 A1 | 2/2002 | Woloszko et al. |
| 2002/0038077 A1 | 3/2002 | de la Torre et al. |
| 2002/0065507 A1 | 5/2002 | Zando-Azizi |
| 2002/0091374 A1 | 6/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 6/2003 | Wang et al. |
| 2003/0139742 A1 | 7/2003 | Wampler et al. |
| 2003/0144656 A1 | 7/2003 | Ocel et al. |
| 2003/0159535 A1 | 8/2003 | Grover et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0191455 A1 | 10/2003 | Sanchez et al. |
| 2003/0229268 A1 | 12/2003 | Uchiyama et al. |
| 2003/0229338 A1 | 12/2003 | Irion et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0117032 A1 | 6/2004 | Roth |
| 2004/0138525 A1 | 7/2004 | Saadat et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0021069 A1 | 1/2005 | Feuer et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0095650 A1 | 5/2005 | Julius et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0234435 A1 | 10/2005 | Layer |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0036264 A1 | 2/2006 | Selover et al. |
| 2006/0046226 A1 | 3/2006 | Bergler et al. |
| 2006/0100501 A1 | 5/2006 | Berkelman et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0135803 A1 | 6/2007 | Belson |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |

(56) References Cited

U.S. PATENT DOCUMENTS

| | | |
|---|---|---|
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0045803 A1 | 2/2008 | Williams et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0109014 A1 | 5/2008 | de la Pena |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0161804 A1 | 6/2008 | Rioux et al. |
| 2008/0164079 A1 | 7/2008 | Ferren et al. |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2008/0269562 A1 | 10/2008 | Marescaux et al. |
| 2009/0012532 A1 | 1/2009 | Quaid et al. |
| 2009/0020724 A1 | 1/2009 | Paffrath |
| 2009/0024142 A1 | 1/2009 | Ruiz Morales |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1 | 9/2009 | Cole et al. |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0185212 A1 | 7/2010 | Sholev |
| 2010/0198231 A1 | 8/2010 | Manzo et al. |
| 2010/0204713 A1 | 8/2010 | Ruiz Morales |
| 2010/0245549 A1 | 9/2010 | Allen et al. |
| 2010/0250000 A1 | 9/2010 | Blumenkranz et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0082365 A1 | 4/2011 | Mcgrogan et al. |
| 2011/0098529 A1 | 4/2011 | Ostrovsky et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0264078 A1 | 10/2011 | Lipow et al. |
| 2011/0270443 A1 | 11/2011 | Kamiya et al. |
| 2011/0276046 A1 | 11/2011 | Heimbecker et al. |
| 2012/0029277 A1 | 2/2012 | Sholev |
| 2012/0029727 A1 | 2/2012 | Sholev |
| 2012/0035582 A1 | 2/2012 | Nelson et al. |
| 2012/0109150 A1 | 5/2012 | Quaid et al. |
| 2012/0116362 A1 | 5/2012 | Kieturakis |
| 2012/0179168 A1 | 7/2012 | Farritor et al. |
| 2012/0253515 A1 | 10/2012 | Coste-Maniere et al. |
| 2013/0041360 A1 | 2/2013 | Farritor et al. |
| 2013/0131695 A1 | 5/2013 | Scarfogliero et al. |
| 2013/0345717 A1 | 12/2013 | Markvicka et al. |
| 2014/0039515 A1 | 2/2014 | Mondry et al. |
| 2014/0046340 A1 | 2/2014 | Wilson et al. |
| 2014/0058205 A1 | 2/2014 | Frederick et al. |
| 2014/0100587 A1 | 4/2014 | Farritor et al. |
| 2014/0249546 A1* | 9/2014 | Shvartsberg ........... B25J 9/0084 606/130 |
| 2014/0276944 A1* | 9/2014 | Farritor .................. A61B 34/30 606/130 |
| 2014/0303434 A1 | 10/2014 | Farritor et al. |
| 2015/0051446 A1 | 2/2015 | Farritor et al. |
| 2015/0297299 A1 | 10/2015 | Yeung et al. |
| 2016/0015461 A1 | 1/2016 | Farritor et al. |
| 2016/0074055 A1 | 3/2016 | Ravikumar et al. |
| 2016/0228154 A1 | 8/2016 | Mickiewicz et al. |
| 2017/0035526 A1 | 2/2017 | Farritor et al. |
| 2017/0354470 A1 | 12/2017 | Farritor et al. |
| 2018/0116734 A1* | 5/2018 | Yeung ................... A61B 34/30 |
| 2018/0140377 A1 | 5/2018 | Reichenbach ........... B25J 18/02 |
| 2019/0090965 A1* | 3/2019 | Farritor ................. A61B 34/30 |
| 2019/0223967 A1 | 7/2019 | Abbott et al. |
| 2020/0046441 A1 | 2/2020 | Liu et al. |
| 2021/0045836 A1 | 2/2021 | Farritor et al. |

FOREIGN PATENT DOCUMENTS

| | | |
|---|---|---|
| EP | 0105656 A2 | 4/1984 |
| EP | 0279591 A1 | 8/1988 |
| EP | 1354670 | 10/2003 |
| EP | 2286756 | 2/2011 |
| EP | 2286756 A1 | 2/2011 |
| EP | 2329787 | 6/2011 |
| EP | 2563261 | 3/2013 |
| EP | 2684528 A1 | 1/2014 |
| EP | 2123225 B1 | 12/2014 |
| EP | 2815705 A1 | 12/2014 |
| EP | 2881046 A2 | 10/2015 |
| EP | 2937047 A1 | 10/2015 |
| JP | H04-144533 A | 5/1992 |
| JP | 05-115425 | 5/1993 |
| JP | 2006508049 | 9/1994 |
| JP | H06-507809 A | 9/1994 |
| JP | H06-508049 A | 9/1994 |
| JP | 07-016235 | 1/1995 |
| JP | 07-136173 | 5/1995 |
| JP | 7306155 | 11/1995 |
| JP | 08-224248 | 9/1996 |
| JP | 2001500510 | 1/2001 |
| JP | 2001505810 | 5/2001 |
| JP | 2002000524 A | 1/2002 |
| JP | 2003220065 | 8/2003 |
| JP | 2004144533 | 5/2004 |
| JP | 2004-180781 | 7/2004 |
| JP | 2004322310 | 11/2004 |
| JP | 2004329292 | 11/2004 |
| JP | 2006507809 | 3/2006 |
| JP | 2009106606 | 5/2009 |
| JP | 2010533045 | 10/2010 |
| JP | 2010536436 | 12/2010 |
| JP | 2011504794 | 2/2011 |
| JP | 2011045500 | 3/2011 |
| JP | 2011115591 | 6/2011 |
| KR | 1020150022414 A | 3/2015 |
| WO | 199221291 | 5/1991 |
| WO | 2001089405 | 11/2001 |
| WO | 2002082979 | 10/2002 |
| WO | 2002100256 | 12/2002 |
| WO | 2005009211 | 7/2004 |
| WO | 2005044095 | 5/2005 |
| WO | 2006052927 | 8/2005 |
| WO | 2006005075 | 1/2006 |
| WO | 2006079108 | 7/2006 |
| WO | 2007011654 | 1/2007 |
| WO | 2007111571 | 10/2007 |
| WO | 2007149559 | 12/2007 |
| WO | 2009023851 | 2/2009 |
| WO | 2009144729 | 12/2009 |

(56) References Cited

FOREIGN PATENT DOCUMENTS

| WO | 2010042611 A1 | 4/2010 |
|---|---|---|
| WO | 2010046823 A1 | 4/2010 |
| WO | 2010050771 | 5/2010 |
| WO | 2011075693 | 6/2011 |
| WO | 2011118646 | 9/2011 |
| WO | 2011135503 | 11/2011 |
| WO | 2013009887 | 1/2013 |
| WO | 2014011238 | 1/2014 |
| WO | 2014160086 A2 | 10/2014 |
| WO | 2015088655 A1 | 6/2015 |
| WO | 2015132549 A1 | 9/2015 |

OTHER PUBLICATIONS

Phee et al., "Development of Microrobotic Devices for Locomotion in the Human Gastrointestinal Tract," International Conference on Computational Intelligence, Robotics and Autonomous Systems (CIRAS 2001), Nov. 28-30, (2001), Singapore.

Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, 1 Pg.

Rentschler et al., "An In Vivo Mobile Robot for Surgical Vision and Task Assistance," Journal of Medical Devices, Mar. 2007, vol. 1: 23-29.

Rentschler et al., "In vivo Mobile Surgical Robotic Task Assistance," 1 pg.

Rentschler et al., "In vivo Robotics during the NEEMO 9 Mission," Medicine Meets Virtual Reality, Feb. 17, 2007, 1 pg.

Rentschler et al., "Mechanical Design of Robotic In Vivo Wheeled Mobility," ASME Journal of Mechanical Design, 2006a, pp. 1-11.

Rentschler et al., "Miniature in vivo Robots for Remote and Harsh Environments," IEEE Transactions on Information Technology in Biomedicine, Jan. 2008; 12(1): 66-75.

Rentschler et al., "Mobile In Vivo Biopsy and Camera Robot," Studies in Health and Infonnatics Medicine Meets Virtual Reality, vol. 119, pp. 449-454, IOS Press, Long Beach, CA, 2006e.

Rentschler et al., "Mobile In Vivo Camera Robots Provide Sole Visual Feedback for Abdominal Exploration and Cholecystectomy," Journal of Surgical Endoscopy, 20-1: 135-138, 2006b.

Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.

Rentschler et al., "Modeling, Analysis, and Experimental Study of In Vivo Wheeled Robotic Mobility," IEEE Transactions on Robotics, 22 (2): 308-321, 2005c.

Rentschler et al., "Natural Orifice Surgery with an Endoluminal Mobile Robot," The Society of American Gastrointestinal Endoscopic Surgeons, Dallas, TX, Apr. 2006d, 14 pp.

Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28—Oct. 2, 2004, pp. 1-9.

Rentschler et al., "Toward In Vivo Mobility," Studies in Health Technology and Infonnatics—Medicine Meets Virtual Reality, ISO Press, Long Beach, CA, 2005a, III: 397-403.

Rentschler et al., "Mobile In Vivo Biopsy Robot," IEEE International Conference on Robotics and Automation, Orlando, Florida, May 2006, pp. 4155-4160.

Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.

Riviere et al., "Toward Active Tremor Canceling in Handheld Microsurgical Instruments," IEEE Transactions on Robotics and Automation, Oct. 2003, 19(5): 793-800.

Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.

Rosen et al., "Objective Laparoscopic Skills Assessments of Surgical Residents Using Hidden Markov Models Based on Haptic Information and Tool/Tissue Interactions," Studies in Health Technology and Infonnatics—Medicine Meets Virtual Reality, Jan. 2001, 7 pp.

Rosen et al., "Spherical Mechanism Analysis of a Surgical Robot for Minimally Invasive Surgery—Analytical and Experimental Approaches," Studies in Health Technology and Infonnatics—Medicine Meets Virtual Reality, pp. 442-448, Jan. 2005.

Rosen et al., "The Blue Dragon—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.

Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.

Ruurda et al., "Feasibility of Robot-Assisted Laparoscopic Surgery," Surgical Laparoscopy, Endoscopy & Percutaneous Techniques, 2002; 12(1 ):41-45.

Ruurda et al., "Robot-Assisted surgical systems: a new era in laparoscopic surgery," Ann R. Coll Surg Engl., 2002; 84: 223-226.

Sackier et al., "Robotically assisted laparoscopic surgery," Surgical Endoscopy, 1994; 8: 63-66.

Salky, "What is the Penetration of Endoscopic Techniques into Surgical Practice?" Digestive Surgery, 2000; 17:422-426.

Satava, "Surgical Robotics: The Early Chronicles," Surgical Laparoscopy, Endoscopy & Percutaneous Techniques, 2002; 12(1): 6-16.

Schippers et al., (1996) "Requirements and Possibilities of Computer-Assisted Endoscopic Surgery," In: Computer Integrated Surgery: Technology and Clinical Applications, pp. 561-565.

Schurr et al., "Robotics and Telemanipulation Technologies for Endoscopic Surgery," Surgical Endoscopy, 2000; 14: 375-381.

Schwartz, "In the Lab: Robots that Slink and Squirm," The New York Times, Mar. 27, 2007, 4 pp.

Sharp LL-151-3O, http://www.sharp3d.com, 2006, 2 pp.

Slatkin et al., "The Development of a Robotic Endoscope," Proceedings of the 1995 IEEE International Conference on Robotics and Automation, pp. 162-171, 1995.

Smart Pill "Fastastic Voyage: Smart Pill to Expand Testing," http://www.smartpilldiagnostics.com, Apr. 13, 2005, 1 pg.

Southern Surgeons Club (1991), "A prospective analysis of 1518 laparoscopic cholecystectomies," N. Eng. 1 Med. 324 (16): 1073-1078.

Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.

Stiff et al., "Long-term Pain: Less Common After Laparoscopic than Open Cholecystectomy," British Journal of Surgery, 1994; 81: 1368-1370.

Strong, et al., "Efficacy of Novel Robotic Camera vs. a Standard Laproscopic Camera," Surgical Innovation vol. 12, No. 4, Dec. 2005, Westminster Publications, Inc., pp. 315-318.

Suzumori et al., "Development of Flexible Microactuator and its Applications to Robotics Mechanisms," Proceedings of the IEEE International Conference on Robotics and Automation, 1991: 1622-1627.

Taylor et al., "A Telerobotic Assistant for Laparoscopic Surgery," IEEE Eng Med Biol, 1995; 279-287.

Tendick et al., "Applications of Micromechatronics in Minimally Invasive Surgery," IEEE/AS ME Transactions on Mechatronics, 1998; 3(1): 34-42.

Tendick et al. (1993), "Sensing and Manipulation Problems in Endoscopic Surgery: Experiment, Analysis, and Observation," Presence 2(1): 66-81.

(56) References Cited

OTHER PUBLICATIONS

Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,106, filed Nov. 26, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy a Breakthrough Diagnostic Tool for Small Intestine Imaging," vol. 25, No. 1, 2002, Gastroenterology Nursing, pp. 24-27.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughlin, M.L., Hespanha, J.P., and Sukhatme, G., editors. Touch in virtual environments, IMSC Series in Multimedia 2001, 28pp.

Dumpert et al., "Stereoscopic In Vivo Surgical Robots," IEEE Sensors Special Issue on In Vivo Sensors for Medicine, Jan. 2007, 10 pp.
Green, "Telepresence Surgery", Jan. 1, 1995, Publisher: IEEE Engineering in Medicine and Biology.
Cleary et al., "State of the Art in Surgical Rootics: Clinical Applications and Technology Challenges", "Computer Aided Surgery", Jan. 1, 2002, pp. 312-328, vol. 6.
Stoianovici et al., "Robotic Tools for Minimally Invasive Urologic Surgery", Jan. 1, 2002, pp. 1-17.
Franzino, "The Laprotek Surgical System and the Next Generation of Robotics," Surg Clin North Am, 2003 83(6): 1317-1320.
Franklin et al., "Prospective Comparison of Open vs. Laparoscopic Colon Surgery for Carcinoma: Five-Year Results," Dis Colon Rectum, 1996; 39: S35-S46.
Flynn et al, "Tomorrow's surgery: micromotors and microrobots for minimally invasive procedures," Minimally Invasive Surgery & Allied Technologies, 1998; 7(4): 343-352.
Fireman et al., "Diagnosing small bowel Crohn's desease with wireless capsule endoscopy," Gut 2003; 52: 390-392.
Fearing et al., "Wing Transmission for a Micromechanical Flying Insect," Proceedings of the 2000 IEEE International Conference to Robotics & Automation, Apr. 2000; 1509-1516.
Faraz et al., "Engineering Approaches to Mechanical and Robotic Design for Minimaly Invasive Surgery (MIS)," Kluwer Academic Publishers (Boston), 2000, 13pp.
Falcone et al., "Robotic Surgery," Clin. Obstet. Gynecol. 2003, 46(1): 37-43.
Fraulob et al., "Miniature assistance module for robot-assisted heart surgery," Biomed. Tech. 2002, 47 Suppl. 1, Pt. 1: 12-15.
Fukuda et al., "Mechanism and Swimming Experiment of Micro Mobile Robot in Water," Proceedings of the 1994 IEEE International Conference on Robotics and Automation, 1994: 814-819.
Fukuda et al., "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Dumpert et al., "Improving in Vivo Robot Visioin Quality," from the Proceedings of Medicine Meets Virtual Realtiy, Long Beach, CA, Jan. 26-29, 2005. 1 pg.
Dakin et al., "Comparison of laparoscopic skills performance between standard instruments and two surgical robotic systems," Surg Endosc., 2003; 17: 574-579.
Cuschieri, "Technology for Minimal Access Surgery," BMJ, 1999, 319: 1-6.
Grady, "Doctors Try New Surgery for Gallbladder Removal," The New York Times, Apr. 20, 2007, 3 pp.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Chanthasopeephan et al., (2003), "Measuring Forces in Liver Cutting: New Equipment and Experimeal Results," Annals of Biomedical Engineering 31: 1372-1382.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Guber et al., "Miniaturized Instrument Systems for Minimally Invasive Diagnosis and Therapy," Biomedizinische Technic. 2002, Band 47, Erganmngsband 1: 198-201.
Abbou et al., "Laparoscopic Radical Prostatectomy with a Remote Controlled Robot," The Journal of Urology, Jun. 2001, 165: 1964-1966.
Glukhovsky et al., "The development and application of wireless capsule endoscopy," Int. J. Med. Robot. Comput. Assist. Surgery, 2004; I (1): 114-123.

(56) References Cited

OTHER PUBLICATIONS

Gong et al., Wireless endoscopy, Gastrointestinal Endoscopy 2000; 51(6): 725-729.
Guo et al., "Fish-like Underwater Microrobot with 3 DOF," Proceedings of the 2002 IEEE International Conference on Robotics & Automation, May 2002: 738-743.
Guo et al., "Micro Active Guide Wire Catheter System—Characteristic Evaluation, Electrical Model and Operability Evaluation of Micro Active Catheter," Proceedings of the 1996 IEEE International Conference on Robotics and Automation, Apr. 1996: 2226-2231.
Hanly et al., "Robotic Abdominal Surgery," The American Journal of Surgery 188 (Suppl.to Oct. 1994): 19S-26S, 2004.
Hanly et al., "Value of the SAGES Learning Center in introducing new technology," Surgical Endoscopy, 2004; 19 (4): 477-483.
Heikkinen et al., "Comparison of laparoscopic and open Nissen fundoplication two years after operation: A prospective randomized trial," Surgical Endoscopy, 2000; 14: 1019-1023.
Hissink, "Olympus Medical develops capsule camera technology," Dec. 2004, accessed Aug. 29, 2007, http://www.letsgodigital.org , 3 pp.
Horgan et al., "Technical Report: Robots in Laparoscopic Surgery," Journal of Laparoendoscopic & Advanced Surgical Techniques, 2001; 11(6): 415-419.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136: 180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
Macfarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, ¼-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 2004, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13 (3):181-184.
Palm, William, "Rapid Prototyping Primer" May 1998 (revised Jul. 30, 2002) (http://www.me.psu.edu/lamancusa/rapidpro/primer/chapter2.htm).
Park et al., "Experimental studies of transgastric gallbladder surgery: cholecystectomy and cholecystogastric anastomosis (videos)," Gastrointestinal Endoscopy, 2005; 61 (4): 601-606.
Park et al., "Trocar-less Instrumentation for Laparoscopy: Magnetic Positioning of Intra-abdominal Camera and Retractor," Ann Surg, Mar. 2007; 245(3): 379-384.
Patronik et al., "Crawling on the Heart: A Mobile Robotic Device for Minimally Invasive Cardiac Interventions," MICCAI, 2004, pp. 9-16.
Patronik et al., "Development of a Tethered Epicardial Crawler for Minimally Invasive Cardiac Therapies," IEEE, 2004, pp. 239-240.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Roh et al. "Development of the SAIT single-port surgical access robot—slave arm based on RCM Mechanism" 2015 37th Annual International Conference of the IEEE Engineering in Medicine and Biology Society, Aug. 25, 2015, pp. 6.
European Patent Office "Extended European Search Report" from Application No. 21838524.3, Dated Jul. 5, 2024, pp. 10.

* cited by examiner

SURGICAL ROBOT POSITIONING SYSTEM AND RELATED DEVICES AND METHODS

CROSS-REFERENCE TO RELATED APPLICATION

This application claims the benefit under 35 U.S.C. § 119(e) to U.S. Provisional Application 63/048,620, filed Jul. 6, 2020 and entitled "Surgical Robot Positioning System and Related Devices and Methods," which is hereby incorporated herein by reference in its entirety.

FIELD

The various embodiments herein relate to robotic surgical systems, and more specifically to surgical robot positioning systems and devices that aid in the gross positioning of surgical devices during surgical procedures. The combination of a gross positioning system with an in vivo surgical device results in an increase in the degrees of freedom of the in vivo device without increasing the size of the device.

BACKGROUND

The known positioning systems currently used for robotic surgery are large and cumbersome. For example, the Da Vinci SP Surgical System™ takes up a significant portion of the operating room and creates a crowded space over the surgical site, and the system created by Waseda University has bulky motor housings that create a larger than necessary profile. In a further example, the Raven™ mimics current laparoscopic techniques by inserting a single tool (in contrast to the in vivo robot systems used in the other two systems discussed above).

Certain of these known systems include a known, generic spherical mechanism that can be used to reach the extents of the abdominal cavity of a patient. A "spherical mechanism" is a physical mechanism or software application that can cause all end effector motions to pass through a single point, thereby allowing a surgical system to use long rigid tools that perform procedures through incisions that serve as single pivot points. As an example, both COBRASurge and the Raven have mechanical spherical mechanisms, while Da Vinci has a software-based spherical mechanism.

There is a need in the art for an improved positioning system.

BRIEF SUMMARY

Discussed herein are various gross positioning systems for use with robotic surgical devices such as in vivo surgical devices.

In Example 1, a gross positioning system for use with a robotic surgical device comprises a positioning body, a yaw mechanism operably coupled to the positioning body at a first rotational joint, a pitch mechanism operably coupled to the positioning body at a second rotational joint, and a plunge mechanism slidably coupled to the pitch mechanism such that the plunge mechanism can move along a length of a plunge axis, wherein the plunge mechanism is configured to be coupleable to the robotic surgical device.

Example 2 relates to the gross positioning system according to Example 1, wherein the yaw mechanism further comprises a motor operably engaged with an output shaft configured to rotate the positioning body around the first rotational joint.

Example 3 relates to the gross positioning system according to Example 2, wherein the yaw mechanism further comprises: a drive gear coupled to the motor, a driven gear operably engaged with the drive gear, a screw coupled to the driven gear, and a wheel is coupled to the output shaft, wherein the wheel is operably engaged with the screw.

Example 4 relates to the gross positioning system according to Example 1, wherein the pitch mechanism further comprises a motor operably engaged with a curved output rail configured to rotate the plunge mechanism around the second rotational joint.

Example 5 relates to the gross positioning system according to Example 4, wherein the pitch mechanism further comprises: a screw coupled to the motor, a wheel operably engaged with the screw, and a rotatable gear operably coupled to the wheel, wherein the rotatable gear is operably engaged with the curved output rail.

Example 6 relates to the gross positioning system according to Example 1, wherein the plunge mechanism further comprises a motor operably engaged with an elongate output rail configured to translationally move the plunge mechanism along the plunge axis.

Example 7 relates to the gross positioning system according to Example 1, wherein the plunge mechanism further comprises a clamp configured to be coupleable to the robotic surgical device.

Example 8 relates to the gross positioning system according to Example 1, wherein a first axis of rotation of the first rotational joint, a second axis of rotation of the second rotational joint, and the plunge axis intersect at a single point of intersection.

Example 9 relates to the gross positioning system according to Example 8, further comprising two or more lasers configured to emit light beams intersecting at the single point of intersection.

Example 10 relates to the gross positioning system according to Example 1, further comprising a controller operably coupled to the gross positioning system and the robotic surgical device, wherein the gross positioning system and robotic surgical device are configured to operate together to position the robotic surgical device within a body cavity of a patient.

In Example 11, a gross positioning system for use with a robotic surgical device comprises a positioning body, a yaw mechanism operably coupled to the positioning body at a first rotational joint, a pitch mechanism operably coupled to the positioning body at a second rotational joint, a plunge mechanism slidably coupled to the pitch mechanism such that the plunge mechanism can move along a length of a plunge axis, wherein the plunge mechanism is configured to translationally move the robotic surgical device along the length of the plunge axis, and the robotic surgical device operably coupled to the plunge mechanism, the robotic surgical device comprising a device body and an arm operably coupled to the device body, the arm comprising an end effector, wherein the robotic surgical device is positionable through an insertion point in a patient such that the arm and at least a portion of the device body is positionable within a body cavity of the patient.

Example 12 relates to the gross positioning system according to Example 11, wherein a first axis of rotation of the first rotational joint, a second axis of rotation of the second rotational joint, and the plunge axis intersect at a single point of intersection.

Example 13 relates to the gross positioning system according to Example 12, wherein the single point of intersection is disposed at some point along a portion of the robotic surgical device.

Example 14 relates to the gross positioning system according to Example 12, wherein the single point of intersection is disposed at an insertion point of a patient and the arm is partially disposed through the single point of intersection.

Example 15 relates to the gross positioning system according to Example 14, wherein the insertion point comprises an incision or a natural orifice.

In Example 16, an external gross positioning system for use with an internal robotic surgical device comprises a support arm, a positioning body operably coupled to the support arm, a yaw mechanism operably coupled to the positioning body at a first rotational joint, a pitch mechanism operably coupled to the positioning body at a second rotational joint, a plunge mechanism slidably coupled to the pitch mechanism such that the plunge mechanism can move along a length of a plunge axis, wherein the plunge mechanism is configured to be coupleable to the internal robotic surgical device, and a single point of intersection of an axis of rotation of the first rotational joint, an axis of rotation of the second rotational joint, and the plunge axis.

Example 17 relates to the external gross positioning system according to Example 16, wherein the support arm further comprises a clamp configured to couple with a bed rail, a rod coupled to the clamp, a first elongate arm operably coupled to the rod at a third rotational joint, and a second elongate arm operably coupled to the first elongate arm at a fourth rotational joint and operably coupled to the positioning body at a fifth rotational joint.

Example 18 relates to the external gross positioning system according to Example 17, wherein the third rotational joint, the fourth rotational joint, and the fifth rotational joint are each configured to rotate around parallel axes.

Example 19 relates to the external gross positioning system according to Example 16, wherein the robotic surgical device comprises at least one arm, wherein the external gross positioning system and robotic surgical device are configured to operate together to position the robotic surgical device within a body cavity of a patient.

Example 20 relates to the external gross positioning system according to Example 19, further comprising a central processing unit operably coupled to the external gross positioning system and the robotic surgical device, wherein the central processing unit comprises software configured to transmit control instructions to the external gross positioning system and the robotic surgical device, and a controller operably coupled to the central processing unit.

In Example 21, a method for performing surgery comprises rotating, at a first rotational joint, a yaw mechanism operably coupled to a positioning body at the first rotational joint, rotating, at a second rotational joint, a pitch mechanism operably coupled to the positioning body at the second rotational joint, and sliding, along a length of a plunge axis, a plunge mechanism operably coupled to the pitch mechanism, wherein a robotic surgical device is configured to slide with the robotic surgical device along the length of the plunge axis.

In Example 22, a method for performing surgery comprises adjusting a first arm of a support arm operably coupled to a positioning body, rotating, at a first rotational joint, a yaw mechanism operably coupled to the positioning body at the first rotational joint, rotating, at a second rotational joint, a pitch mechanism operably coupled to the positioning body at the second rotational joint, sliding, along a length of a plunge axis, a plunge mechanism operably coupled to the pitch mechanism, wherein a robotic surgical device is configured to slide with the robotic surgical device along the length of the plunge axis, and aligning the robotic surgical device at a single point of intersection of an axis of rotation of the first rotational joint, an axis of rotation of the second rotational joint, and the plunge axis.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

DETAILED DESCRIPTION

Figure 1:
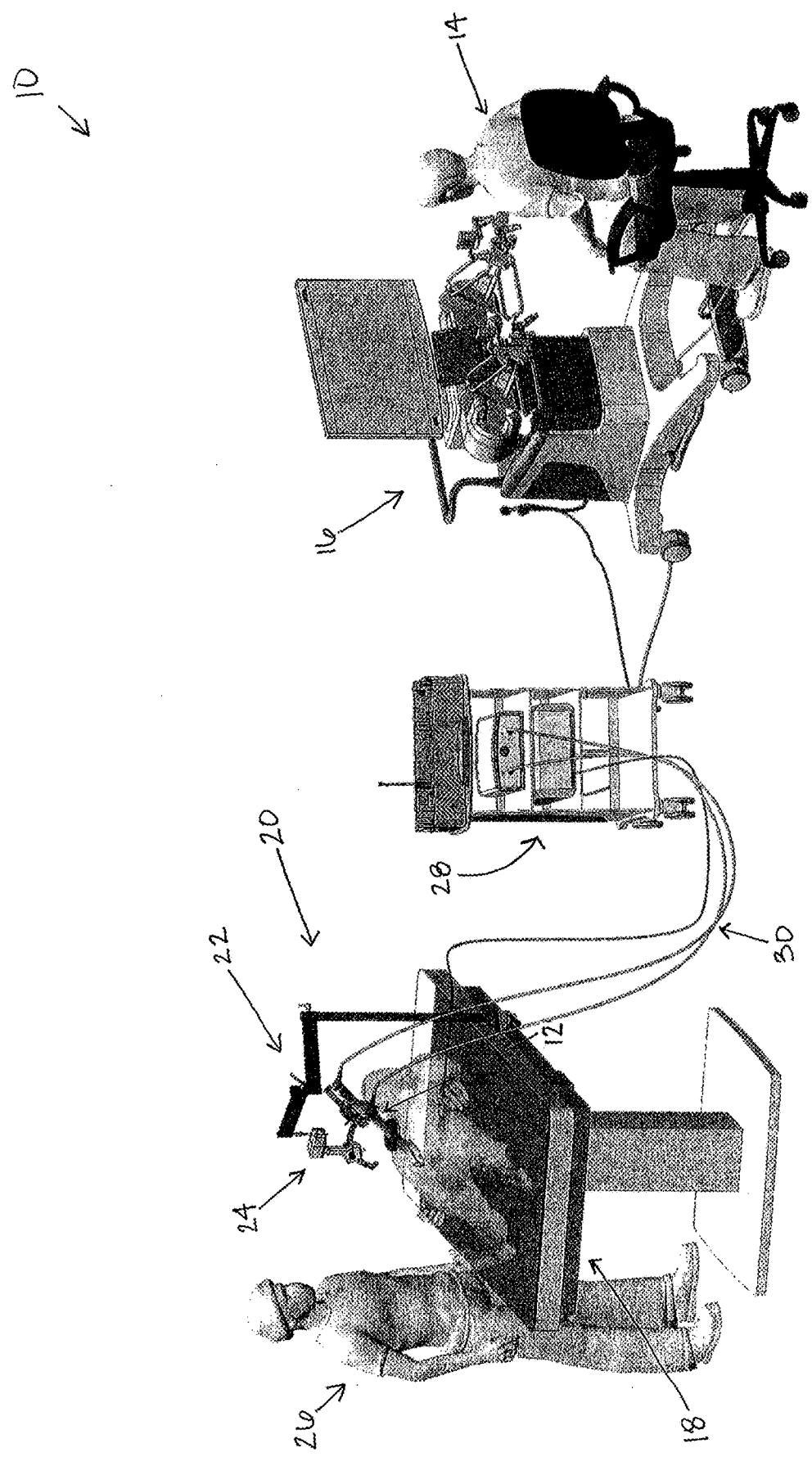
FIG. 1 is a robotic surgical system, according to one embodiment.

The various embodiments disclosed or contemplated herein relate to a surgical robot positioning system that includes a passive support arm and a gross positioning robotic device. A dexterous in vivo surgical robotic device is coupleable to the gross positioning robotic device such that the positioning system can be used for global orientation of the surgical robotic device within the cavity of a patient as described in further detail herein.

The various gross positioning system implementations disclosed or contemplated herein can be used to automatically grossly position a surgical device inside a cavity of a patient. "Gross positioning," as used herein, is intended to mean general positioning of an entire moveable surgical device (in contrast to precise movement and placement of the specific components of such a device, such as an arm or end effector). In known robotic surgical systems, the gross positioning of those devices during a surgical procedure can be a challenging task. Further, minimally invasive surgical procedures (using either robotic or non-robotic systems) frequently require a surgical technician to reposition the surgical equipment, such as a laparoscope. Such gross repositioning takes time and additional effort. In some cases, the surgical technician is a junior medical student who is not fully trained in laparoscopy. As a result, the repositioning instructions from the surgeon often result in an obstructed and/or fogged view of the surgical site, requiring additional cognitive resources from the surgeon. For example, the Da Vinci® system as well as known single incision surgical devices often require timely manual repositioning of the patient, the robotic system, or both while performing complicated procedures.

The various gross positioning systems contemplated herein aid in the gross repositioning of surgical devices throughout the procedure without additional intervention or manual repositioning from the surgical staff. The surgical devices may include, for example, any surgical devices that have a device body, rod, or tube configured to be positioned through an incision and at least one robotic arm coupled to or positioned through the device body or tube that is positioned entirely within the cavity of the patient. The gross positioning system embodiments can control the degrees of freedom, azimuth and elevation angle, and roll and translation about the axis of insertion of laparoscopic surgical tools, including robotic laparoscopic surgical tools. As a result, the gross positioning system embodiments disclosed and contemplated herein can grossly position a surgical device through an incision, port, or orifice (including a natural orifice) into a patient cavity, such as the abdominal cavity, with high manipulability, reducing the operative time and stress induced upon the surgical staff. The combination of the external gross positioning system with the internal surgical device system will allow the degrees of freedom of the internal system to effectively increase without increasing the size of the surgical robot/device.

In one implementation, the various systems and devices described and contemplated herein can be used with any single site surgical device or system with an available external positioning fixture, such as a protruding body, rod, tube, or magnetic handle. Further, it is understood that the various embodiments of positioning systems disclosed herein can be used with any other known medical devices, systems, and methods that are positioned through an incision, port, or orifice (including a natural orifice). For example, the various embodiments disclosed herein may be used with any of the medical devices and systems disclosed in U.S. Pat. No. 8,968,332 (issued on Mar. 3, 2015 and entitled "Magnetically Coupleable Robotic Devices and Related Methods"), U.S. Pat. No. 8,834,488 (issued on Sep. 16, 2014 and entitled "Magnetically Coupleable Surgical Robotic Devices and Related Methods"), U.S. Pat. No. 10,307,199 (issued on Jun. 4, 2019 and entitled "Robotic Surgical Devices and Related Methods"), U.S. Pat. No. 9,579,088 (issued on Feb. 28, 2017 and entitled "Methods, Systems, and Devices for Surgical Visualization and Device Manipulation"), U.S. Patent Application 61/030,588 (filed on Feb. 22, 2008), U.S. Pat. No. 8,343,171 (issued on Jan. 1, 2013 and entitled "Methods and Systems of Actuation in Robotic Devices"), U.S. Pat. No. 8,828,024 (issued on Sep. 9, 2014 and entitled "Methods and Systems of Actuation in Robotic Devices"), U.S. Pat. No. 9,956,043 (issued on May 1, 2018 and entitled "Methods and Systems of Actuation in Robotic Devices"), U.S. patent application Ser. No. 15/966,606 (filed on Apr. 30, 2018 and entitled "Methods, Systems, and Devices for Surgical Access and Procedures"), U.S. patent application Ser. No. 12/192,663 (filed on Aug. 15, 2008 and entitled "Medical Inflation, Attachment, and Delivery Devices and Related Methods"), U.S. patent application Ser. No. 15/018,530 (filed on Feb. 8, 2016 and entitled "Medical Inflation, Attachment, and Delivery Devices and Related Methods"), U.S. Pat. No. 8,974,440 (issued on Mar. 10, 2015 and entitled "Modular and Cooperative Medical Devices and Related Systems and Methods"), U.S. Pat. No. 8,679,096 (issued on Mar. 25, 2014 and entitled "Multifunctional Operational Component for Robotic Devices"), U.S. Pat. No. 9,179,981 (issued on Nov. 10, 2015 and entitled "Multifunctional Operational Component for Robotic Devices"), U.S. Pat. No. 9,883,911 (issued on Feb. 6, 2018 and entitled "Multifunctional Operational Component for Robotic Devices"), U.S. patent application Ser. No. 15/888,723 (filed on Feb. 5, 2018 and entitled "Multifunctional Operational Component for Robotic Devices"), U.S. Pat. No. 8,894,633 (issued on Nov. 25, 2014 and entitled "Modular and Cooperative Medical Devices and Related Systems and Methods"), U.S. Pat. No. 8,968,267 (issued on Mar. 3, 2015 and entitled "Methods and Systems for Handling or Delivering Materials for Natural Orifice Surgery"), U.S. Pat. No. 9,060,781 (issued on Jun. 23, 2015 and entitled "Methods, Systems, and Devices Relating to Surgical End Effectors"), U.S. Pat. No. 9,757,187 (issued on Sep. 12, 2017 and entitled "Methods, Systems, and Devices Relating to Surgical End Effectors"), U.S. Pat. No. 10,350,000 (issued on Jul. 16, 2019 and entitled "Methods, systems, and devices relating to surgical end effectors"), U.S. patent application Ser. No. 16/512,510 (filed on Jul. 16, 2019 and entitled "Methods, Systems, and Devices Relating to Surgical End Effectors"), U.S. Pat. No. 9,089,353 (issued on Jul. 28, 2015 and entitled "Robotic Surgical Devices, Systems, and Related Methods"), U.S. Pat. No. 10,111,711 (issued on Oct. 30, 2018 and entitled "Robotic Surgical Devices, Systems, and Related Methods"), U.S. patent application Ser. No. 16/123,619 (filed on Sep. 6, 2018 and entitled "Robotic Surgical Devices, Systems and Related Methods"), U.S. Pat. No. 9,770,305 (issued on Sep. 26, 2017 and entitled "Robotic Surgical Devices, Systems, and Related Methods"), U.S. patent application Ser. No. 15/661,147 (filed on Jul. 27, 2017 and entitled "Robotic Devices with On Board Control & Related Systems & Devices"), U.S. patent application Ser. No. 13/833,605 (filed on Mar. 15, 2013 and entitled "Robotic Surgical Devices, Systems, and Related Methods"), U.S. patent application Ser. No. 13/738,706 (filed on Jan. 10, 2013 and entitled "Methods, Systems, and Devices for Surgical Access and Insertion"), U.S. patent application Ser. No. 14/661,465 (filed on Mar. 18, 2015 and entitled "Methods, Systems, and Devices for Surgical Access and Insertion"), U.S. patent application Ser. No. 15/890,860 (filed on Feb. 7, 2018 and entitled "Methods, Systems, and Devices for Surgical Access and Insertion"), U.S. Pat. No. 9,498,292 (issued on Nov. 22, 2016 and entitled "Single Site Robotic Devices and Related Systems and Methods"), U.S. Pat. No. 10,219,870 (issued on Mar. 5, 2019 and entitled "Single site robotic device and related systems and methods"), U.S. patent application Ser. No. 16/293,135 (filed Mar. 3, 2019 and entitled "Single Site Robotic Device and Related Systems and Methods"), U.S. Pat. No. 9,010,214 (issued on Apr. 21, 2015 and entitled "Local Control Robotic Surgical Devices and Related Methods"), U.S. Pat. No. 10,470,828 (issued on Nov. 12, 2019 and entitled "Local Control Robotic Surgical Devices and Related Methods"), U.S. patent application Ser. No. 16/596,034 (filed on Oct. 8, 2019 and entitled "Local Control Robotic Surgical Devices and Related Methods"), U.S. Pat. No. 9,743,987 (issued on Aug. 29, 2017 and entitled "Methods, Systems, and Devices Relating to Robotic Surgical Devices, End Effectors, and Controllers"), U.S. patent application Ser. No. 15/687,787 (filed on Aug. 28, 2017 and entitled "Methods, Systems, and Devices Relating to Robotic Surgical Devices, End Effectors, and Controllers"), U.S. Pat. No. 9,888,966 (issued on Feb. 13, 2018 and entitled "Methods, Systems, and Devices Relating to Force Control Surgical Systems"), U.S. patent application Ser. No. 15/894,489 (filed on Feb. 12, 2018 and entitled "Methods, Systems, and Devices Relating to Force Control Surgical Systems"), U.S. patent application Ser. No. 14/212,686 (filed on Mar. 14, 2014 and entitled "Robotic Surgical Devices, Systems, and Related Methods"), U.S. patent application Ser. No. 14/334,383 (filed on Jul. 17, 2014 and entitled "Robotic Surgical Devices, Systems, and Related Methods"), U.S. patent application Ser. No. 14/853,477 (filed on Sep. 14, 2015 and entitled "Quick-Release End Effectors and Related Systems and Methods"), U.S. patent application Ser. No. 16/504,793 (filed on Jul. 8, 2019 and entitled "Quick-Release End Effectors and Related Systems and Methods"), U.S. Pat. No. 10,376,322 (issued on Aug. 13, 2019 and entitled "Robotic Device with Compact Joint Design and Related Systems and Methods"), U.S. patent application Ser. No. 16/538,902 (filed on Aug. 13, 2019 and entitled "Robotic Device with Compact Joint Design and Related Systems and Methods"), U.S. patent application Ser. No. 15/227,813 (filed on Aug. 3, 2016 and entitled Robotic Surgical Devices, System and Related Methods") U.S. patent application Ser. No. 15/599,231 (filed on May 18, 2017 and entitled "Robotic Surgical Devices, Systems, and Related Methods"), U.S. patent application Ser. No. 15/687,113 (filed on Aug. 25, 2017 and entitled "Quick-Release End Effector Tool Interface"), U.S. patent application Ser. No. 15/691,087 (filed on Aug. 30, 2017 and entitled "Robotic Device with Compact Joint Design and an Additional Degree of Freedom and Related Systems and Methods"), U.S. patent application Ser. No. 15/826,166 (filed on Nov. 29, 2017 and entitled "User controller with user presence detection and related systems and methods"), U.S. patent application Ser. No. 15/842,230 (filed on Dec. 14, 2017 and entitled "Releasable Attachment Device for Coupling to Medical Devices and Related Systems and Methods"), U.S. patent application Ser. No. 16/144,807 (filed on Sep. 27, 2018 and entitled "Robotic Surgical Devices with Tracking Camera Technology and Related Systems and Methods"), U.S. patent application Ser. No. 16/241,263 (filed on Jan. 7, 2019 and entitled "Single-Manipulator Robotic Device With Compact Joint Design and Related Systems and Methods"), U.S. Pat. No. 7,492,116 (filed on Oct. 31, 2007 and entitled "Robot for Surgical Applications"), U.S. Pat. No. 7,772,796 (filed on Apr. 3, 2007 and entitled "Robot for Surgical Applications"), and U.S. Pat. No. 8,179,073 (issued on May 15, 2011, and entitled "Robotic Devices with Agent Delivery Components and Related Methods"), all of which are hereby incorporated herein by reference in their entireties.

Certain device and system implementations disclosed in the applications listed above can be positioned within a body cavity of a patient, or a portion of the device can be placed within the body cavity, in combination with a positioning system such as any of the embodiments disclosed or contemplated herein. An "in vivo device" as used herein means any device that can be positioned, operated, or controlled at least in part by a user while being positioned within a body cavity of a patient, including any device that is coupled to a support component such as a rod, tube, body, or other such component that is disposed through an opening or orifice of the body cavity, also including any device positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

In certain implementations, any robotic device that is coupleable to the various positioning system embodiments disclosed or contemplated herein can be positioned through an insertion port. The insertion port can be a known, commercially-available flexible membrane (referred to herein as a "gelport") placed transabdominally to seal and protect the abdominal incision. This off-the-shelf component is the same device or substantially the same device that is used in substantially the same way for Hand-Assisted Laparoscopic Surgery (HALS). The only difference is that the arms of the robotic device according to the various embodiments herein are inserted into the abdominal cavity through the insertion port rather than the surgeon's hand. The robotic device body, rod, or tube seals against the insertion port when it is positioned therethrough, thereby maintaining insufflation pressure. The port is single-use and disposable. Alternatively, any known port can be used. In further alternatives, the various devices that can be used in combination with the various positioning system embodiments herein can be inserted through an incision without a port or through a natural orifice.

FIG. 1 depicts one embodiment of a robotic surgical system 10 having several components that will be described in additional detail below. The components of the various positioning system implementations disclosed or contemplated herein can be used with a full surgical system 10 that includes an external control console 16 and a robotic surgical device 12. In accordance with the implementation of FIG. 1, the robotic surgical device 12 is shown mounted to the operating table 18 (or a rail thereof) via a robot positioning system 20 according to one embodiment as described in additional detail below. The robot positioning system 20 has a passive support arm 22 and a robotic positioning device 24 coupled to the arm 22. The support arm 22 is coupled to the operating table 18 and the robotic device 12 is coupleable to the robotic positioning device 24. The system 10 can be, in certain implementations, operated by the surgeon 14 at the console 16 and one surgical assistant 26 positioned at the operating table 18. That is, the surgeon 14 at the console 16 can control both the robotic device 12 and the gross positioning robotic device 24, and the surgical assistant 26 can control the remaining system 10 components (e.g., passive support arm 22). Alternatively, one surgeon 14 can operate the entire system 10. In a further alternative, three or more people can be involved in the operation of the system 10. It is further understood that the surgeon (or user) 14 can be located at a remote location in relation to the operating table 18 such that the surgeon 14 can be in a different city or country or on a different continent from the patient on the operating table 18. The console 16 can be any console as disclosed in any of the various patents and/or applications incorporated by reference above. Alternatively, the console 16 can be any known console for operating a robotic surgical system or device.

In this specific implementation, the robotic device 12 is connected to the interface pod and electrosurgical unit 28 via connection cables 30. Further, the gross positioning robotic device 24 is also coupled to the interface pod and electrosurgical unit 28 via the connection cables 30. Alternatively, any wired or wireless connection configuration can be used. Further, the interface pod and electrosurgical unit 28 is coupled to the console 16 as shown (and alternatively can be coupled via any known wired or wireless connection). In certain implementations, the system 10 can also interact with other devices during use such as auxiliary monitors, etc.

According to various embodiments, the gross positioning robotic device 24 of the positioning system 20 can dock or otherwise couple with the surgical robotic device 12 and control the position of the workspace of the device 12 by supporting and moving the surgical robotic device 12 during a surgical procedure. This allows the surgeon 14 (and the assistant 26) to have complete control of the robotic device 12 with respect to the target surgical area (the target cavity of the patient).

Figure 2A:
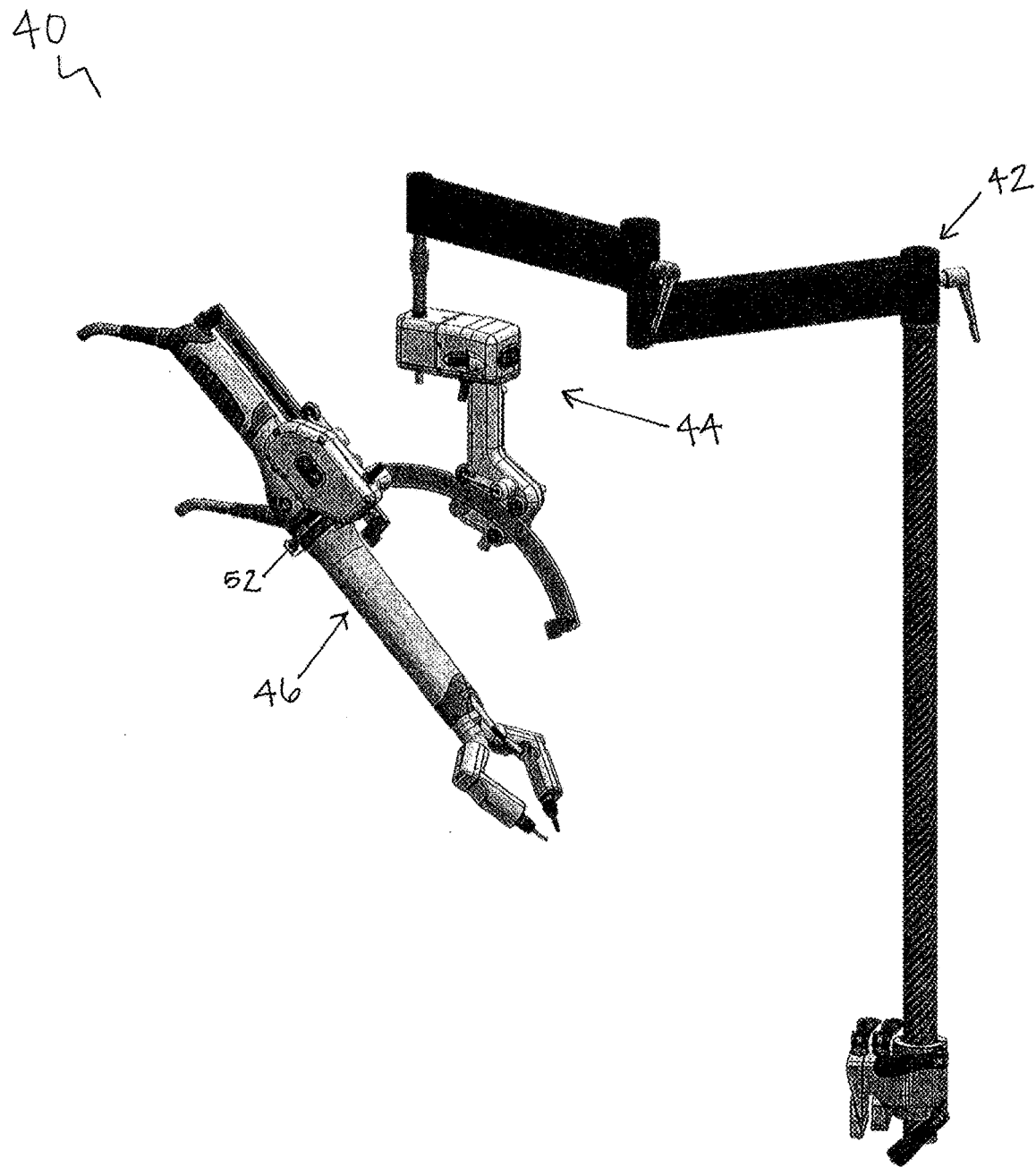
FIG. 2A is a perspective view of a robotic surgical device positioning system coupled to an in vivo robotic device, according to one embodiment.
Figure 2B:
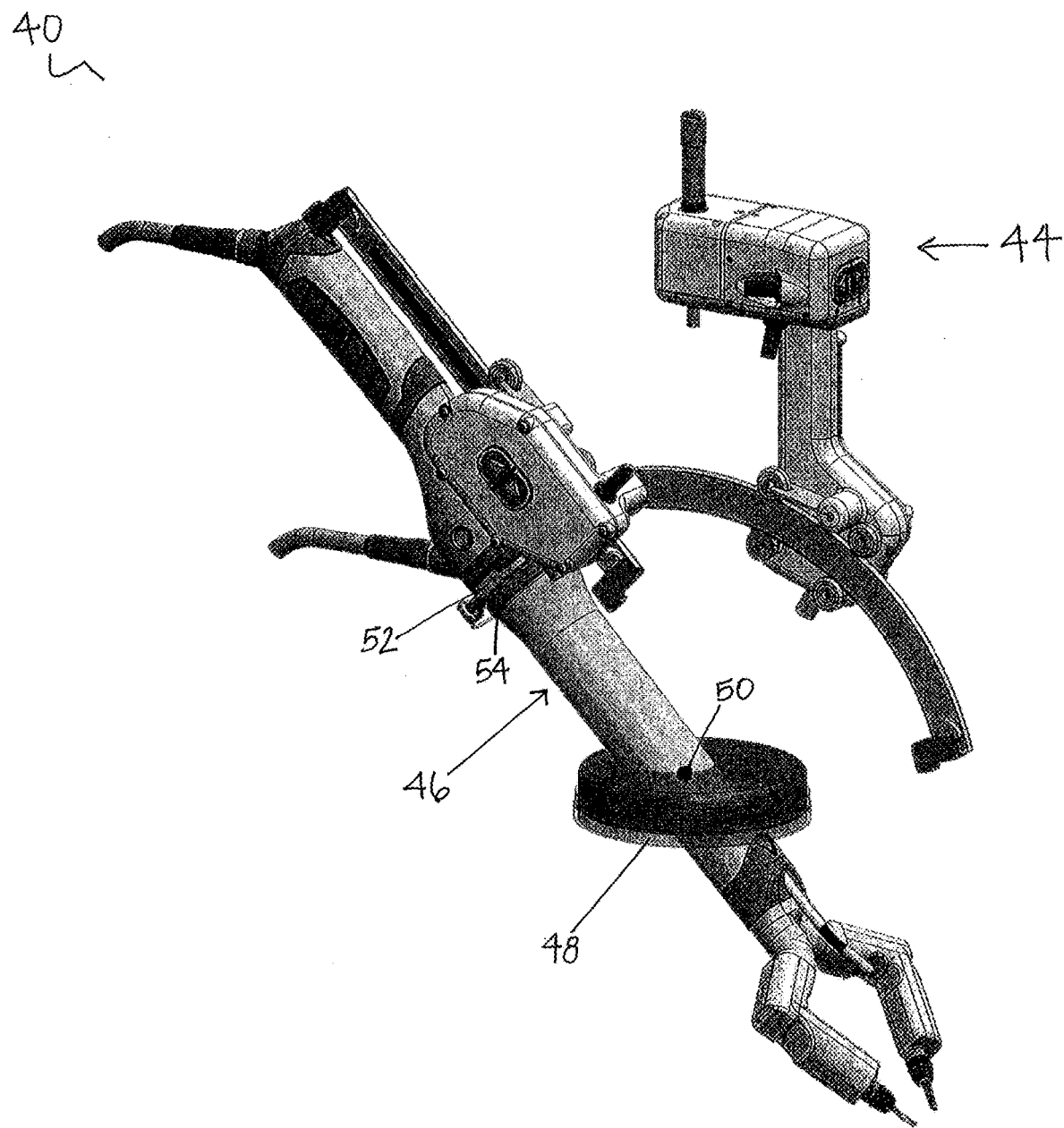
FIG. 2B is a detailed view of a gross positioning system coupled to an in vivo robotic device that is disposed within a cavity of a patient, according to one embodiment.

One embodiment of a robotic surgical device positioning system 40 is depicted in FIGS. 2A and 2B. The system 40 includes a passive support arm 42 and a gross robot positioning device 44 rotatably coupled to the arm 42. Further, any known robotic device 46, which in this specific exemplary implementation is represented by the surgical device 46 as shown, can be removably coupled to the positioning device 44 such that the robotic surgical device 46 is disposed through an opening, orifice, incision, or port into the target cavity of the patient. In this specific embodiment, the robotic surgical device 46 is disposed through a port 48 as best shown in FIG. 2B. In certain embodiments, the port 48 is a gelport 48.

The gross positioning device 44 in this implementation—and various other embodiments as disclosed or contemplated herein—is a 3 degree-of-freedom ("DOF") robotic remote center-of-motion (RCM) mechanism. It is understood that an RCM is the point about which a rotational joint rotates and further that an RCM mechanism is a device where all the kinematic joints move through the same RCM point. For the various gross positioning devices herein (including the robot positioning device 44), the RCM point is within the workspace of the robot positioning device 44 such that, while the end effector of the robotic surgical device 46 can still desirably be manipulated, there is a point of no relative motion with respect to the rest of the mechanism. More specifically, in many implementations the RCM is approximately located at the incision, port, or orifice during surgical use. For example, in the specific embodiment as best shown in FIG. 2B, the RCM point 50 is positioned at the port 48. As such, there is no relative motion at this patient-device interface that could cause harm to the patient, while still allowing the robotic surgical device 46 full access to the target surgical site (a cavity within the patient).

Figure 9A:
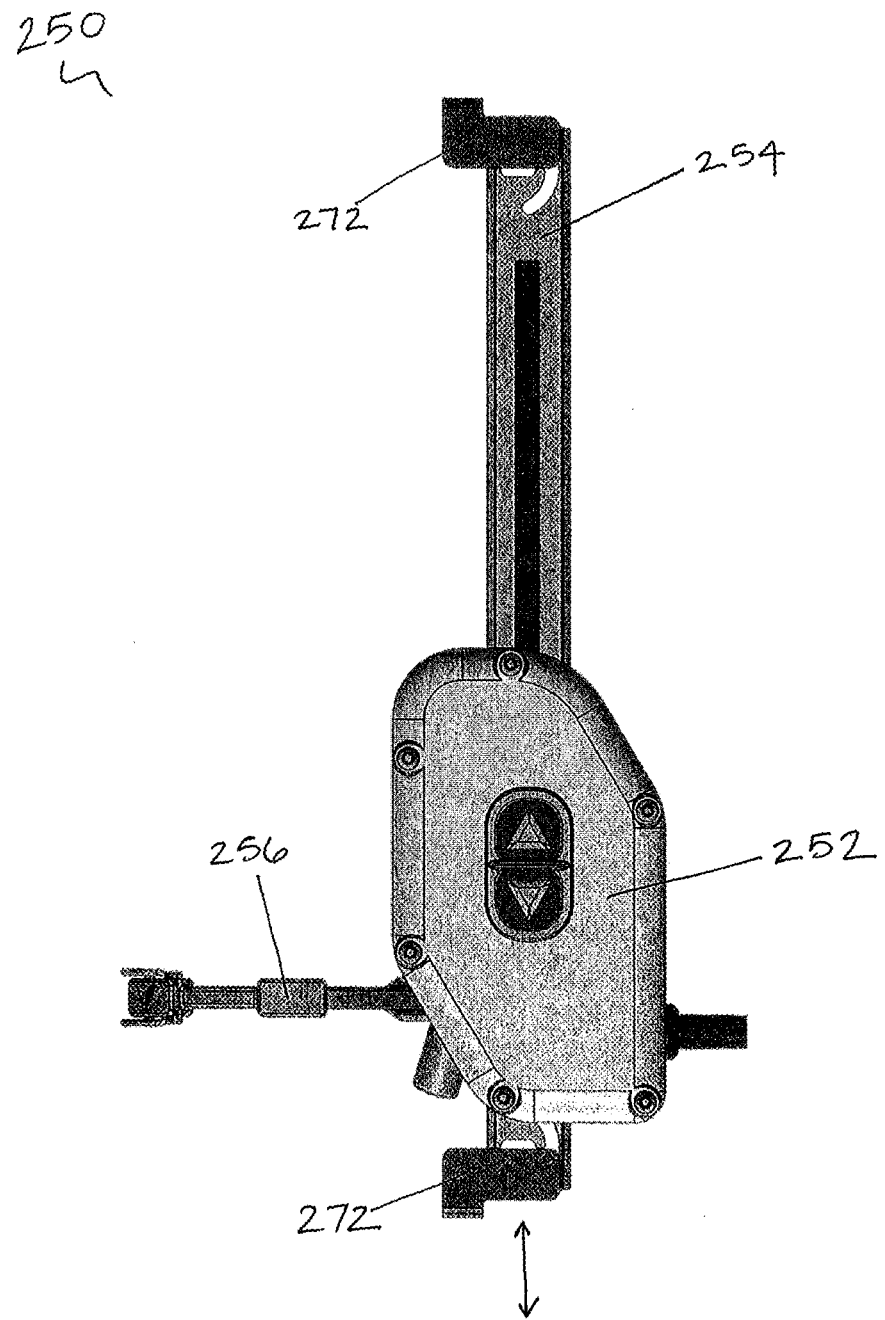
FIG. 9A is a perspective view of a plunge mechanism of a gross positioning system, according to one embodiment.
Figure 9B:
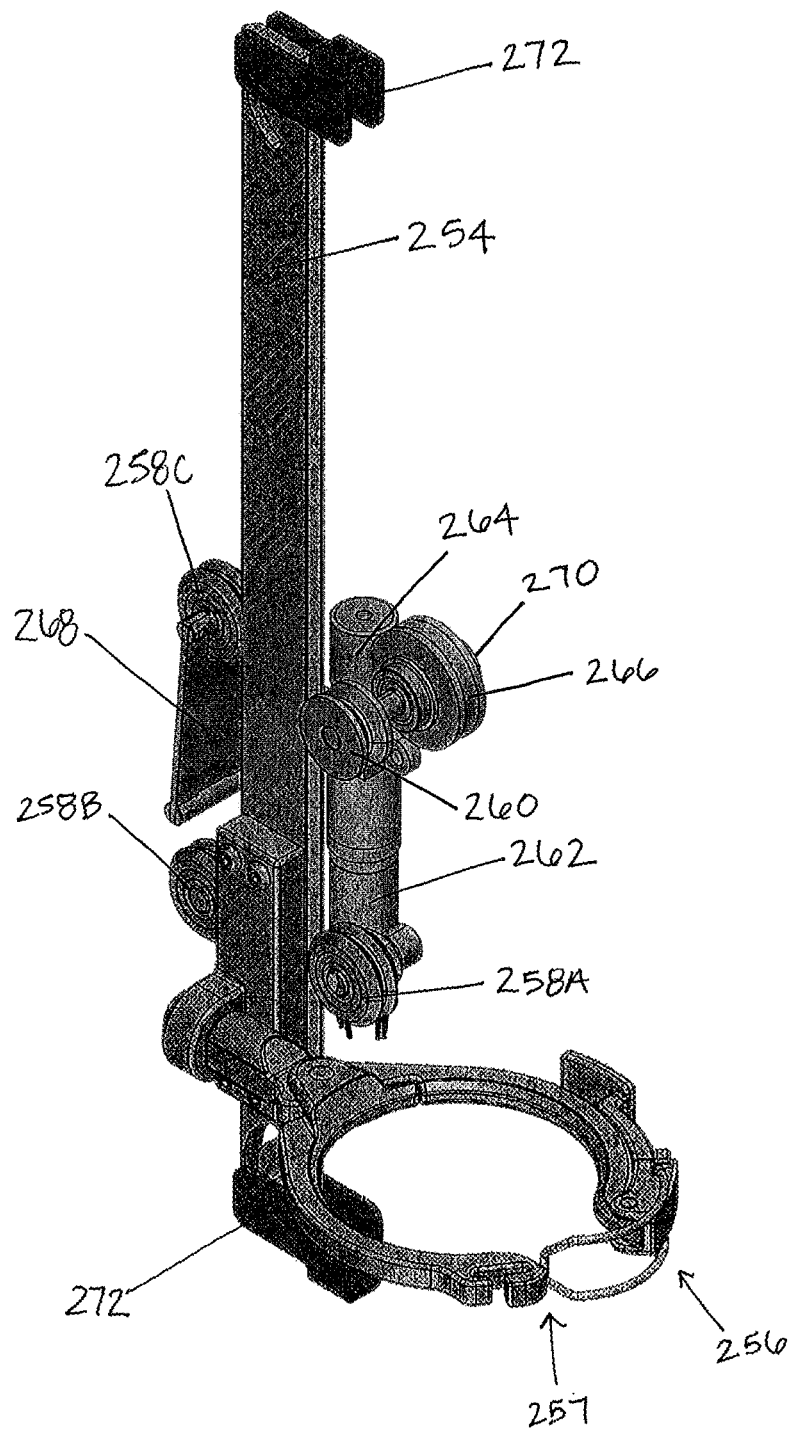
FIG. 9B is a detailed view of the components of the plunge mechanism of FIG. 9A.

The surgical robotic device 46 can be docked or otherwise removably coupled to the gross positioning device 44 via a connecting clamp 52, as best shown in FIGS. 2A-2B, 3B, and 9B. In this particular embodiment, the clamp 52 is coupleable to the robot positioning device 44 at a specific location on the robotic surgical device 44 having a recessed area 54 (e.g., a clamping groove) around the external surface of the device 44 such that the clamp 52 can easily be disposed within the recessed area 54. For example, as shown in FIG. 9B, a similar clamp 256 embodiment has a latch mechanism 257. Alternatively, any known coupling feature or mechanism can be used. In this embodiment, when the surgical robotic device 46 is docked with the gross positioning device 44, it does not move or rotate with respect to the clamp 52. The attachment mechanism 52 is easily and quickly disengaged when desired by the user.

As discussed above, the port 48 as best shown in FIG. 2B can come in various forms. One embodiment would be a gelport that includes a gel like substance that would seal around the circumference of the robot, to maintain insufflation, while still allowing the robot to move. Another port would use air flow to maintain patient insufflation. Others might use various types of mechanical seals such as diaphragm, duck bill, O-ring or other types of seals or ports. Any known port that can maintain a fluidic seal can be used.

Figure 3A:
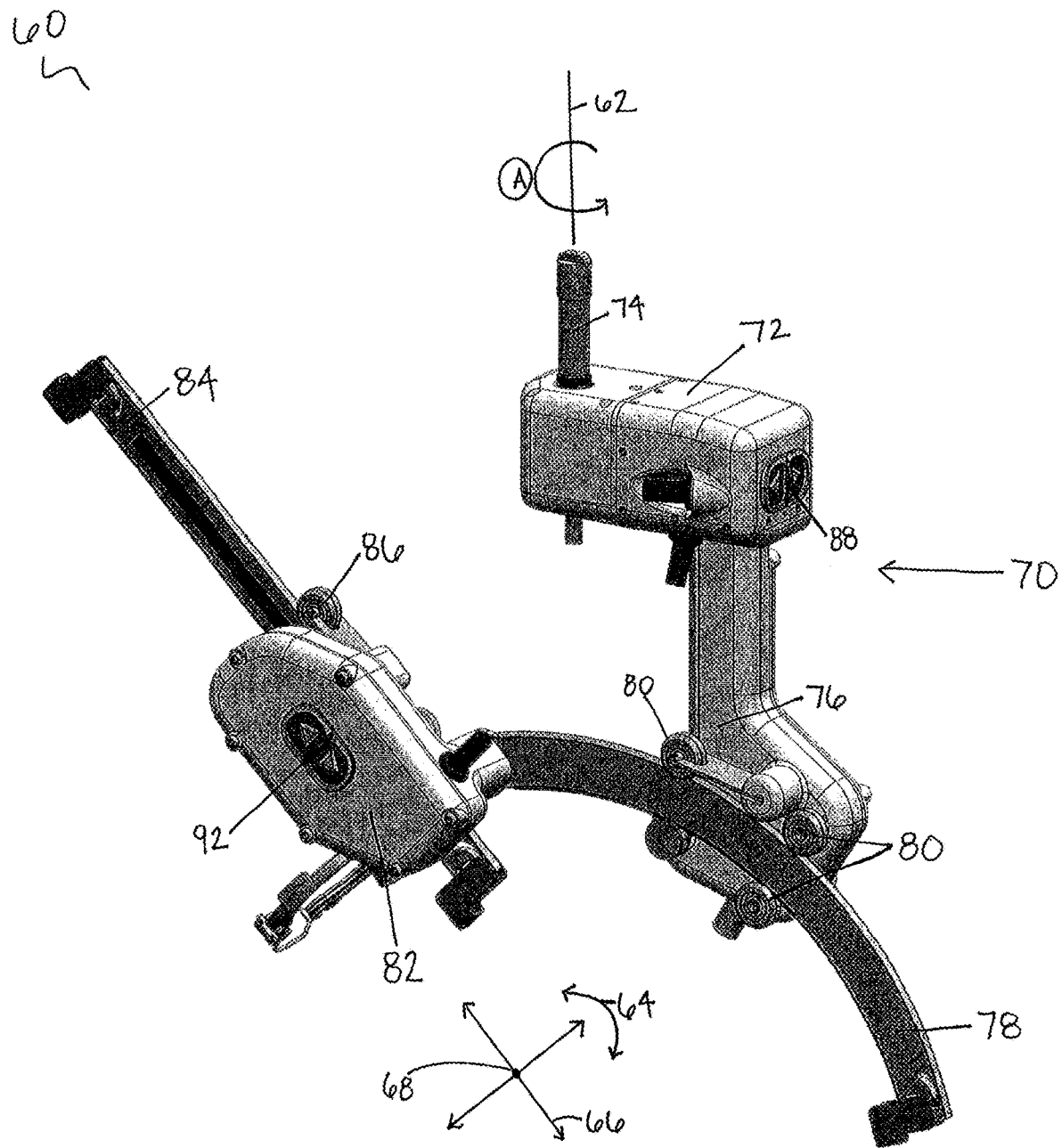
FIG. 3A is a detailed perspective view of a gross positioning system, according to one embodiment.
Figure 3B:
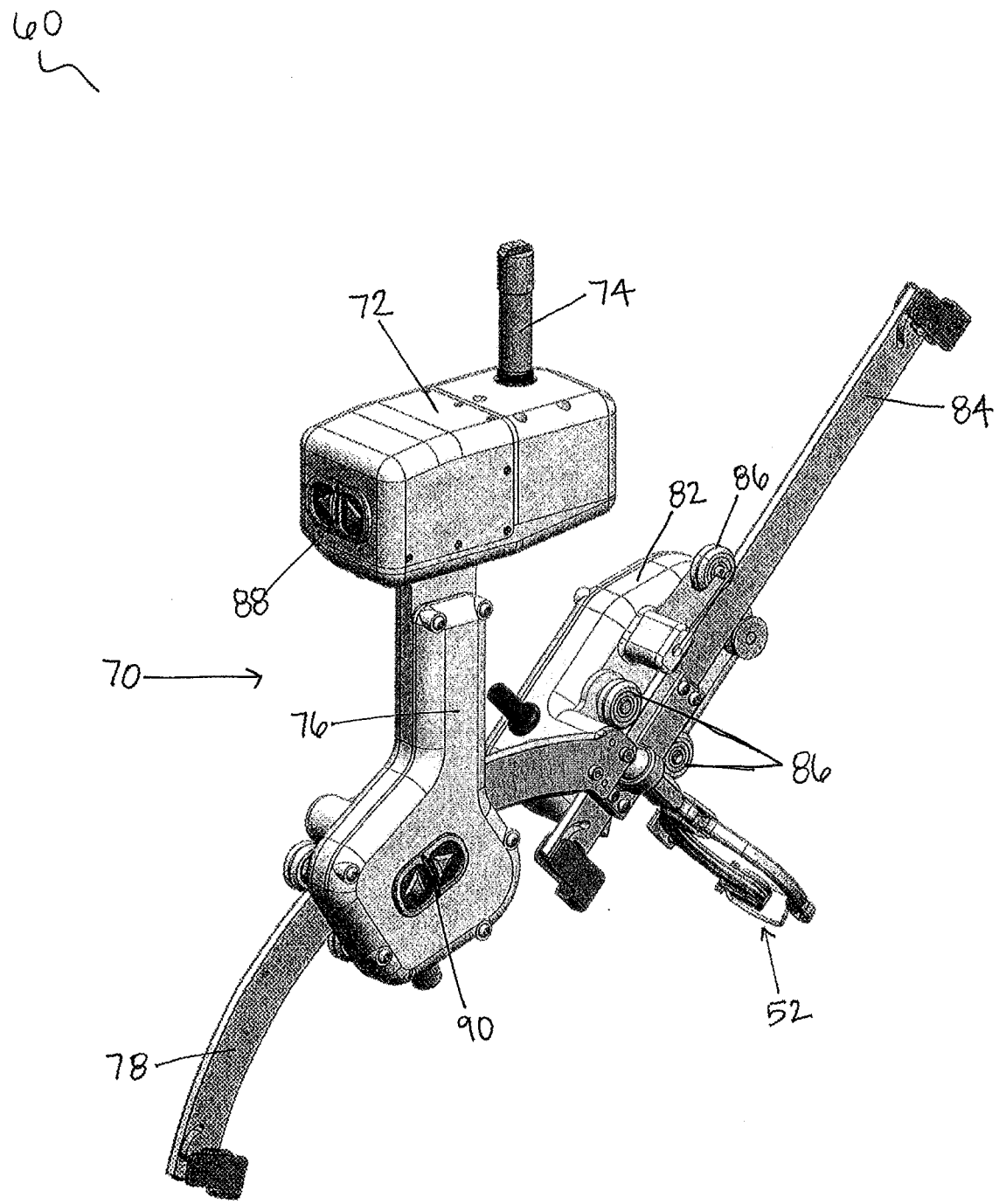
FIG. 3B is another detailed perspective view of a gross positioning system, according to one embodiment.

According to another embodiment of a gross positioning device 60 as shown in FIGS. 3A and 3B, the positioning device 60 has three joints: yaw (joint 1) 62, pitch (joint 2) 64, and plunge (joint 3) 66. Yaw 62 and pitch 64 rotate about the RCM, and plunge 66 moves through the RCM 68. In this embodiment, each joint is fully decoupled and is controlled independently. Further, in certain embodiments, motors and motor controllers (not shown) are co-located at each joint 62, 64, 66. In addition, it is understood that each joint 62, 64, 66 can be, but does not have to be, backdriveable.

The yaw joint 62 originates from the body 70 of the gross robot positioning device 60, and more specifically in the yaw mechanism structure 72. More specifically, a rotatable yaw output shaft 74 extends from the yaw mechanism structure 72 and constitutes the yaw joint 62. As such, rotation of the output shaft 74 creates the yaw motion about the yaw joint 62. The yaw actuator 88 may be actuated to adjust the yaw orientation of the robot positioning device 60, for example, to adjust the yaw mechanism structure 72 and body 70 to the left or the right as shown by arrow A. That is, the yaw actuator 88 can be actuated to cause the output shaft 74 to rotate and thereby cause the structure 72 and body 70 to rotate in either direction as desired. Additionally, the rotation of the body 70 also rotates the pitch mechanism 76 and the plunge mechanism 82.

The pitch joint 64 also originates from the body 70 of the device 60, and more specifically in the pitch mechanism structure 76. More specifically, an output rail 78 is operably coupled to the pitch mechanism structure 76 via rotatable bearings 80 (e.g., grooved rotatable bearings) such that movement of the output rail 78 in relation to the pitch mechanism structure 76 (as described in detail below) creates the pitch joint 64. In some examples, the rotatable bearings 80 engage with the corresponding geometry of the edges of the output rail 78. As such, actuation of the output rail 78 to move in one direction or the other along the bearings 80 creates the pitch at the pitch joint 64. As best shown in FIG. 3B, the pitch actuator 90 may be actuated to adjust the pitch orientation of the plunge mechanism structure 82. That is, the pitch actuator 90 can be actuated to cause the output rail 78 to move in the desired direction to cause the structure 82 to move as desired.

The plunge joint 66 originates from the plunge mechanism structure 82, which is operably coupled to the output rail 78. More specifically, an extendable rail 84 is operably coupled to the plunge mechanism structure 82 via rotatable bearings 86 (as best shown according to one example in FIGS. 3B and 9A-9B below). In some examples, the rotatable bearings 86 engage with the corresponding geometry of the edges of the extendable rail 84. As such, extension of the extendable rail 84 in the distal direction creates the plunge at the plunge joint 66. The plunge actuator 92 may be actuated to adjust the position of the extendable rail 84 along the plunge joint. That is, the plunge actuator 92 can be actuated to cause the extendable rail 84 to move in the desired direction to cause any device attached thereto to move as desired. Thus, movement of the extendable rail 84 will also move the clamp 52 and a device 46, if docked.

Figure 4A:
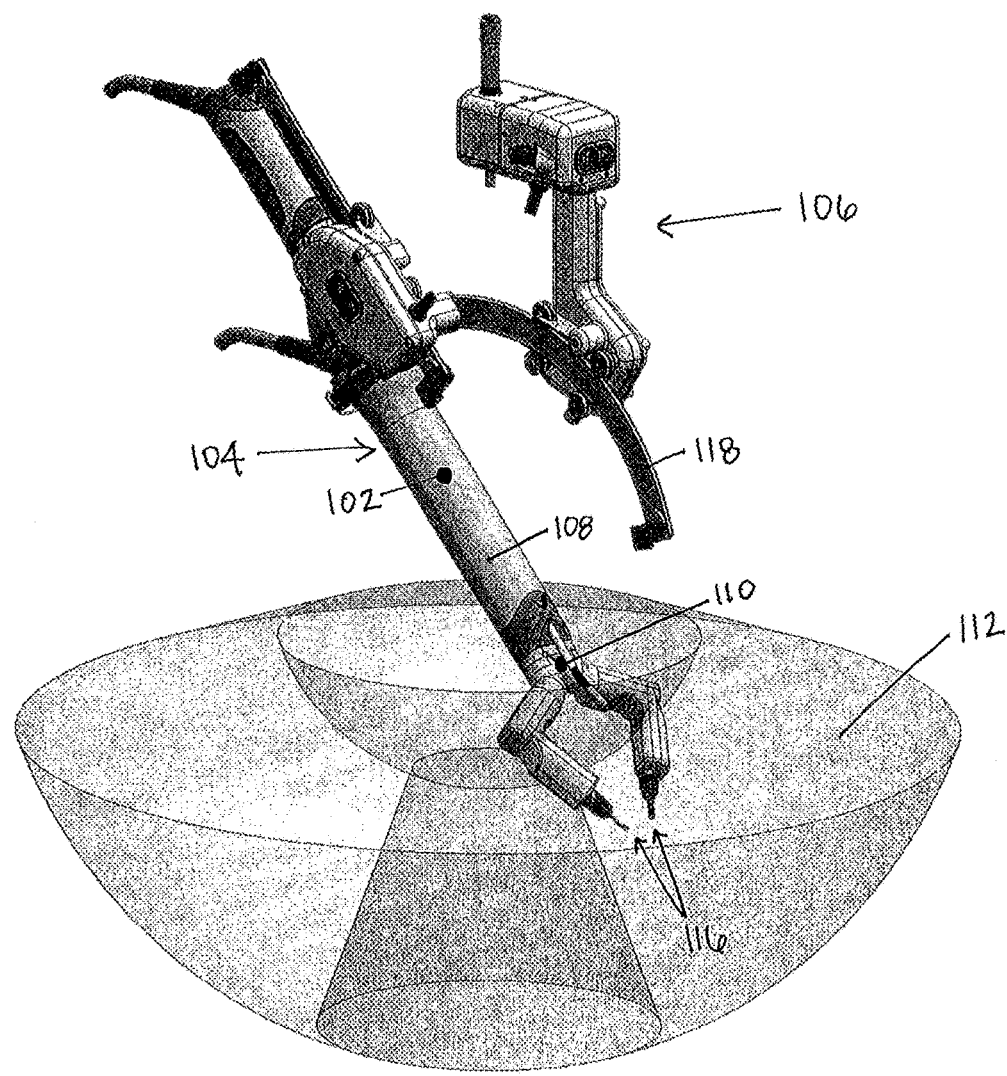
FIG. 4A is a detailed perspective view of the workspace of a gross positioning system coupled to an in vivo robotic device, according to one embodiment.
Figure 4B:
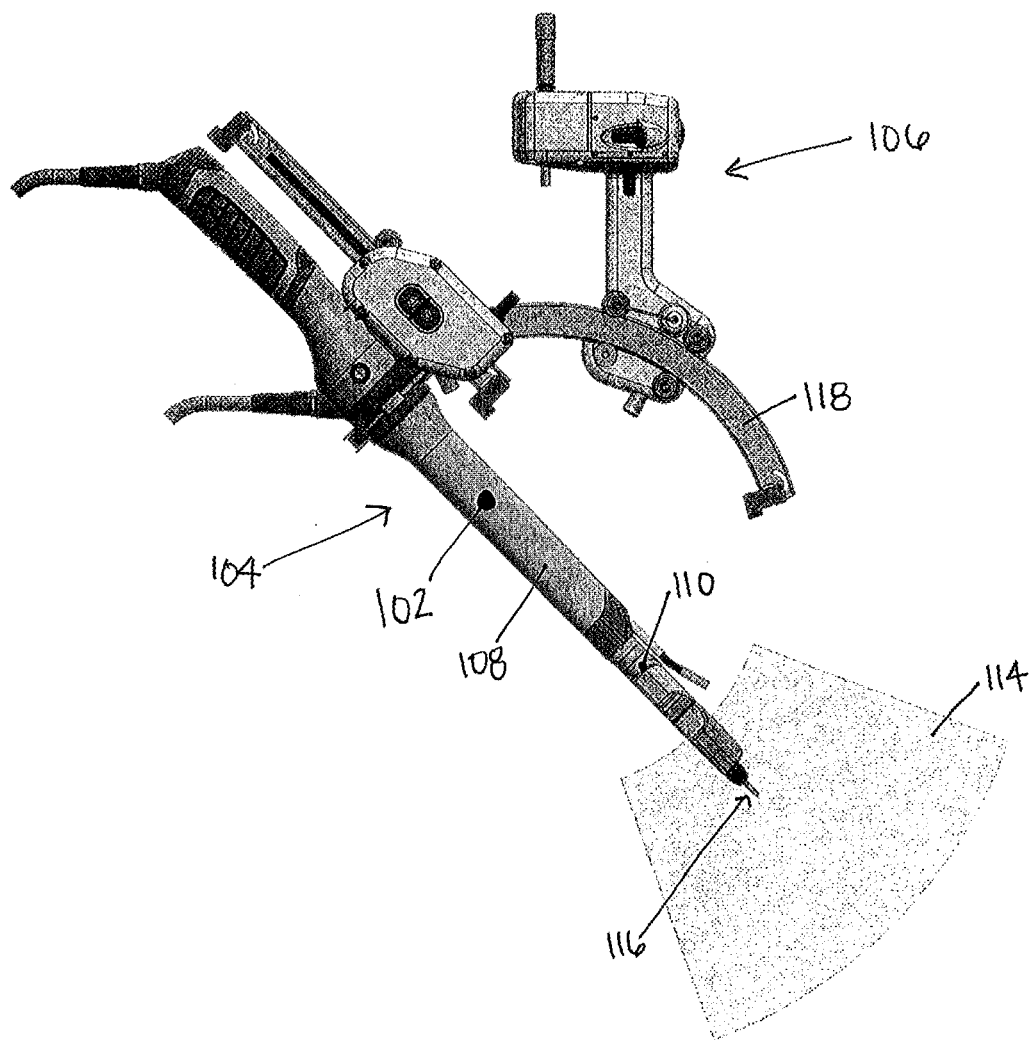
FIG. 4B is a detailed side view of a cross section of the workspace of a gross positioning system coupled to an in vivo robotic device of FIG. 4A.

As best shown in FIGS. 4A and 4B, another implementation of a device positioning system 100 has an RCM 102 that is located at the center of the circular pitch arc as at least partially defined by the curved rail 118. Alternatively, the RCM 102 can be disposed in any known position in relation to the gross positioning device 106. When a robotic surgical device—such as device 104—is docked (or otherwise coupled) to the gross robot positioning device 106, the RCM 102 is disposed within the elongate body (or tube) 108 of the robotic surgical device 104 and approximately colinear with its kinematic origin 110, as shown. FIG. 4A also depicts the workspace 112 of the robot positioning device 106 in the context of the robotic surgical device 104. The gross positioning device 106 can be used to move the kinematic origin 110 and thus, the robotic surgical device 104 such that the end effectors 116 can be moved to any location within the workspace 112 (e.g., a toroidal workspace). The cross-section of the workspace 112, which is governed by pitch and plunge, is an annulus sector 114 as best shown in FIG. 4B.

Returning to FIG. 4A, the yaw joint (such as joint 62 at the output shaft 74 as discussed in detail above with respect to FIG. 3A) is a rotational joint and can be articulated over a sweep angle of at least 165 degrees. In the embodiment of FIG. 4A, the workspace 112 depicts rotation around the output shaft 74 (yaw) with 360 degrees of travel, meaning the gross positioning device 106 can, according to certain embodiments, rotate endlessly in either direction (as cabling adjustment permits). The pitch joint (such as joint 64 created by the rail 78 as discussed in detail above with respect to FIG. 3A) allows rotation about the RCM 102 with motion along the output pitch rail 118. For pitch, according to certain implementations, a 50-degree arc can be traversed, with pitch angles approximately between 20 and 70 degrees from vertical. In some alternative embodiments, a 40-degree arc can be traversed, with pitch angles approximately between 20 and 60 degrees from vertical. In addition, the plunge joint (such as joint 66 created by rail 84 as discussed in detail above with respect to FIG. 3A) is a translational joint and can be translated a total length of at least 100 cm, according to various embodiments.

Figure 5:
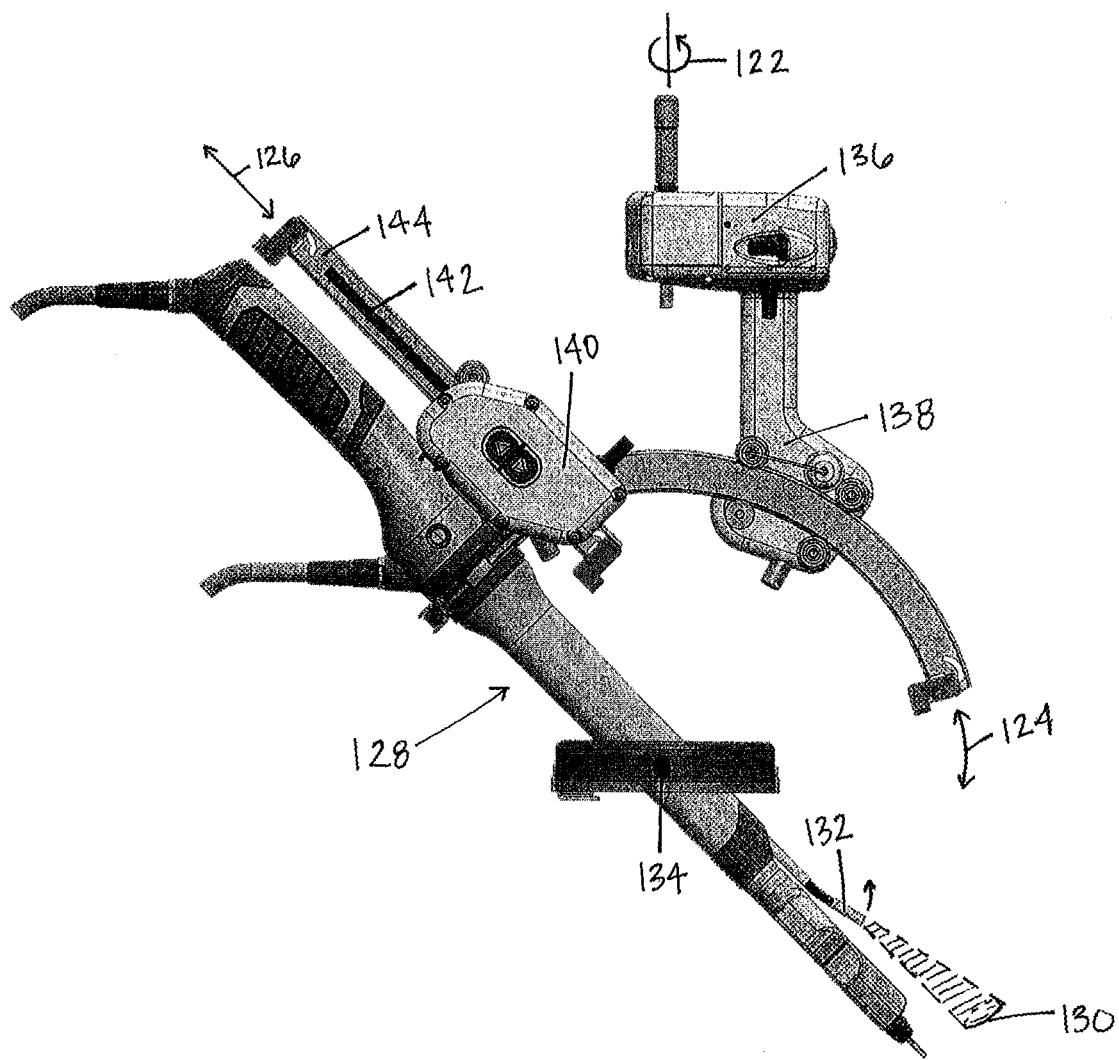
FIG. 5 is a detailed side view of a gross positioning system coupled to an in vivo robotic device with a camera, according to one embodiment.

In the embodiment of the robotic gross positioning device 120 depicted in FIG. 5, each joint 122 (yaw), 124 (pitch), and 126 (plunge) can be moved independently, or they can be moved together in any combination and at any rate. Often, the robotic surgical device 128 is repositioned with respect to the frame of view 130 of the camera 132 on the device 128. Because the camera 132 is robotically articulated in this implementation, its field of view 130 may not always be coaxial with the RCM 134. Therefore, sometimes a combination of the joints 122, 124, and 126 must be articulated to move the robotic surgical device 128 in the camera frame 130 as desired, like in the example shown.

The pitch 124 and plunge 126 joints can, in certain embodiments, have precise absolute position control, and can articulate the full workspace allowed by the gross robot positioning device 120 configuration in most surgical situations. It is understood that absolute position sensing can be achieved with encoders (not shown) on the motors (not shown) used to drive the pitch 124 and plunge 126 stages. Alternatively, a vision-based system that reads markings on the drive rails can be used for absolute position sensing. In a further alternative, absolute position sensing in pitch can be accomplished using a pair of inertial measurement units (IMU), with one IMU mounted normal to the yaw joint 122 within the yaw mechanism structure 136 and a second IMU mounted normal to the translational axis of the plunge joint 126 within the plunge mechanism structure 140. Each IMU may be configured to measure the direction of the gravitational acceleration vector relative to the sensor's normal vector. The absolute pitch angle may then be determined (e.g., in real time or on a delay) by calculating the difference between the two IMU readings. For absolute position sensing along the translational axis of the plunge joint 126, a strip 142 (e.g., a Linear Magnetic Scale Nonius Strip) may be located on or embedded in the plunge rail 144. In some cases, the position of this strip may be determined through the use of a pair of anisotropic magnetoresistance sensors mounted on the inside of the plunge mechanism structure 140 proximate to the strip 142. Alternatively, any known sensors or mechanisms can be used to achieve absolute position control.

Figure 6B:
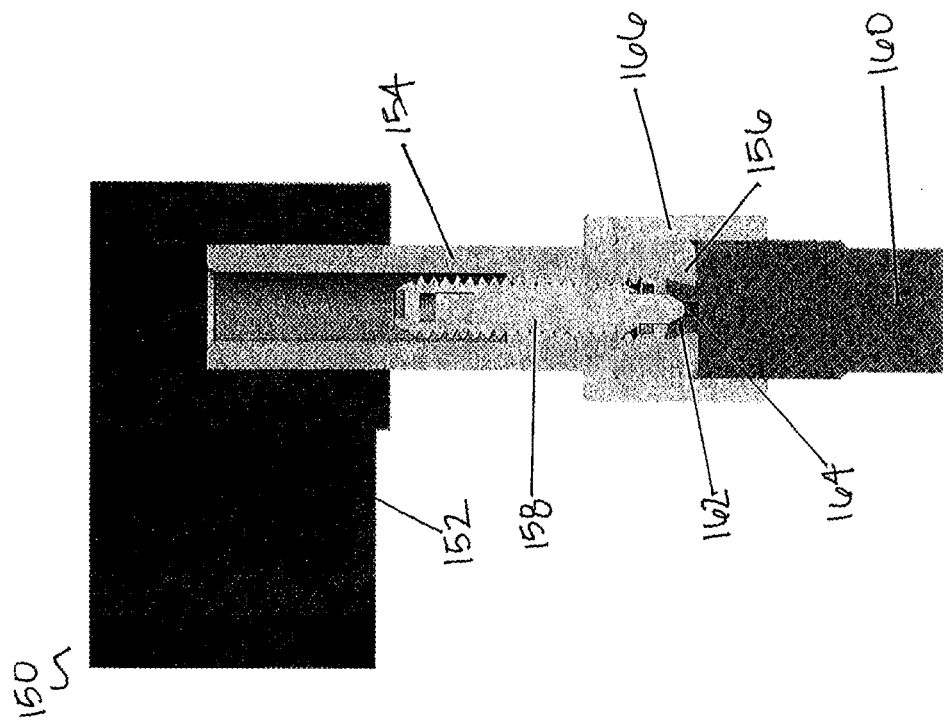
FIG. 6B is an exploded cross-sectional view of the yaw mechanism of a gross positioning system of FIG. 6A.
Figure 6A:
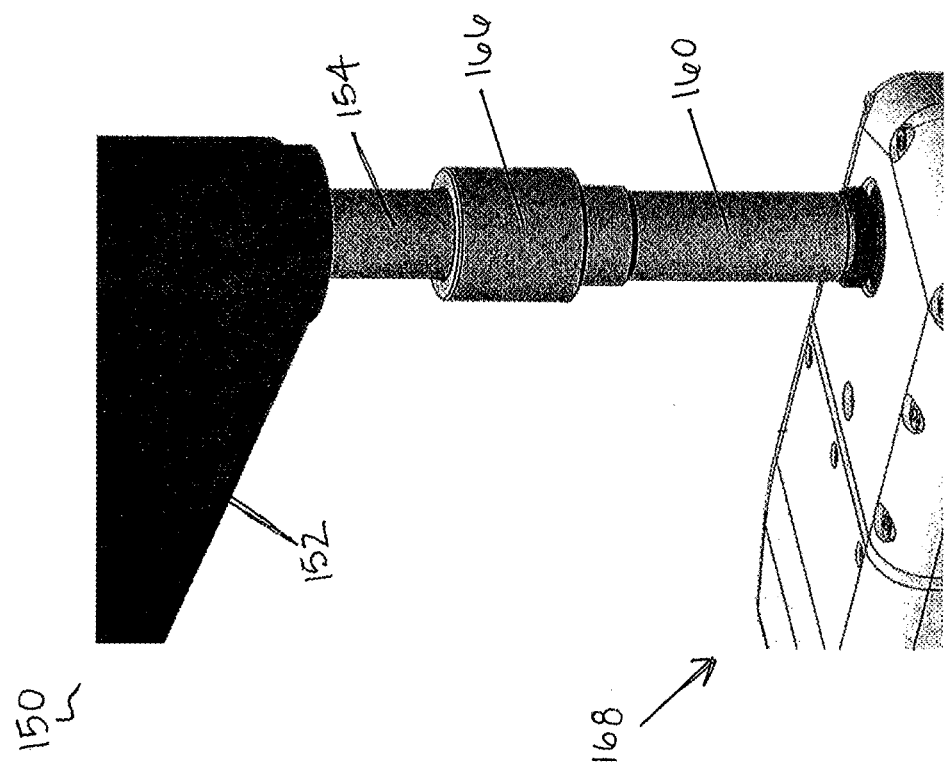
FIG. 6A is a perspective view of a yaw mechanism and the support arm of a gross positioning system, according to one embodiment.

FIGS. 6A and 6B depict one exemplary embodiment of yaw mechanism 150, including an output shaft 160 (similar to the output shaft 74 discussed above) coupled to a connection shaft 154 of a support arm 152. FIG. 6A depicts a perspective view of the output shaft 160 coupled to the connection shaft 154, while FIG. 6B shows a cross-sectional view of the output shaft 160 coupled to the connection shaft 154. In this specific implementation, the coupling and uncoupling of the output shaft 160 and the connection shaft 154 is a relatively fast and simple way to attach/detach the gross positioning device 168 to/from the support arm 152 at the output shaft 160, according to one embodiment.

As shown in FIG. 6B, the output shaft 160 has a male dovetail feature 162 that slides into a female dovetail feature 156 of the connection shaft 154 until a spring-loaded ball detent 158 engages with a center drilled hole 164 of the output shaft 160. This ball detent 158 may preload the connection of the male and female dovetail features 162, 156 and align the output shaft 160 coaxially with the connection shaft 154. To complete the connection, a sleeve 166 is slid down over the connection of the output shaft 160 and the connection shaft 154 to secure the connection and prevent unintended decoupling. The connection supports the weight of the device(s) and prevents rotational motion between the output shaft 160 and the connection shaft 154, while the sleeve 166 prevents relative translation. Alternatively, any other known quick connection mechanisms (such as, for example, the mechanism shown in FIGS. 19A and 19B) can be used for easy docking and undocking of the gross positioning device 168 to the robot support arm 152, such as for cleaning and sterilization.

Figure 7A:
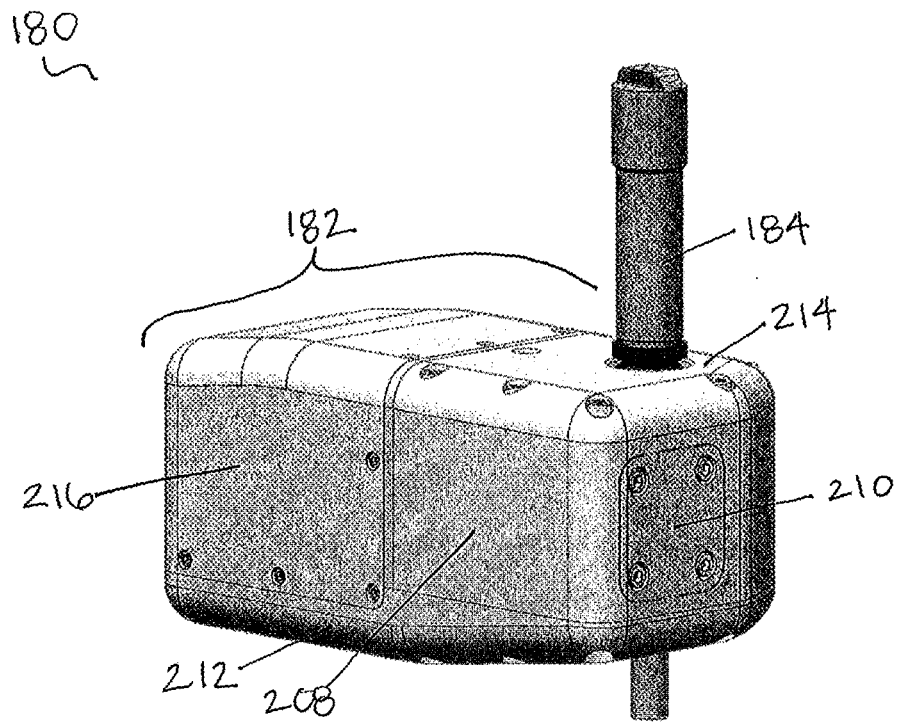
FIG. 7A is a perspective view of a yaw mechanism of a gross positioning system, according to one embodiment.

FIGS. 7A-7D depict a yaw joint (similar to joint 62 as discussed above) 180, according to one embodiment. More specifically, FIG. 7A depicts a yaw mechanism structure 182 having an output shaft 184 rotatably extending from the structure 182 such that the yaw joint 180 originates from the output shaft 184. The structure 182 in one embodiment can have a motor housing (or section) 216 and a drivetrain housing (or section) 208. Alternatively, the structure 182 has only one section or housing. The output shaft 184 can be rotated by the yaw mechanism structure 182 to cause the gross positioning robot (not shown) to rotate in relation to the robot support arm (not shown).

Figure 7B:
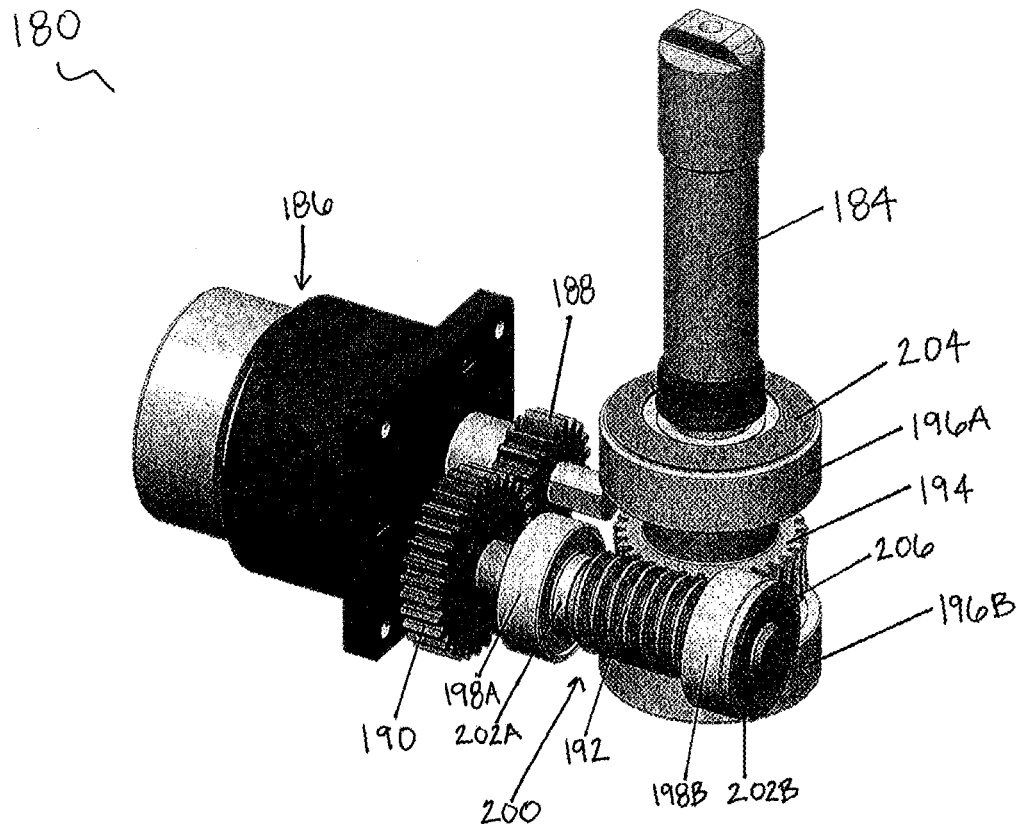
FIG. 7B is a detailed view of the components of the yaw mechanism of FIG. 7A.
Figure 7C:
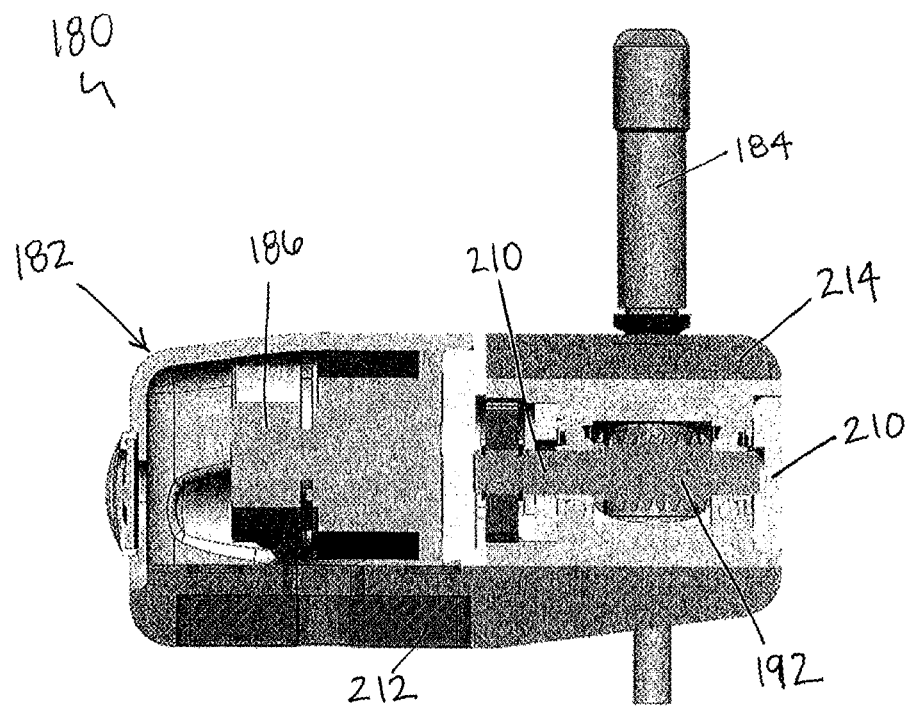
FIG. 7C is a side cross-sectional view of the yaw mechanism of FIG. 7A.
Figure 7D:
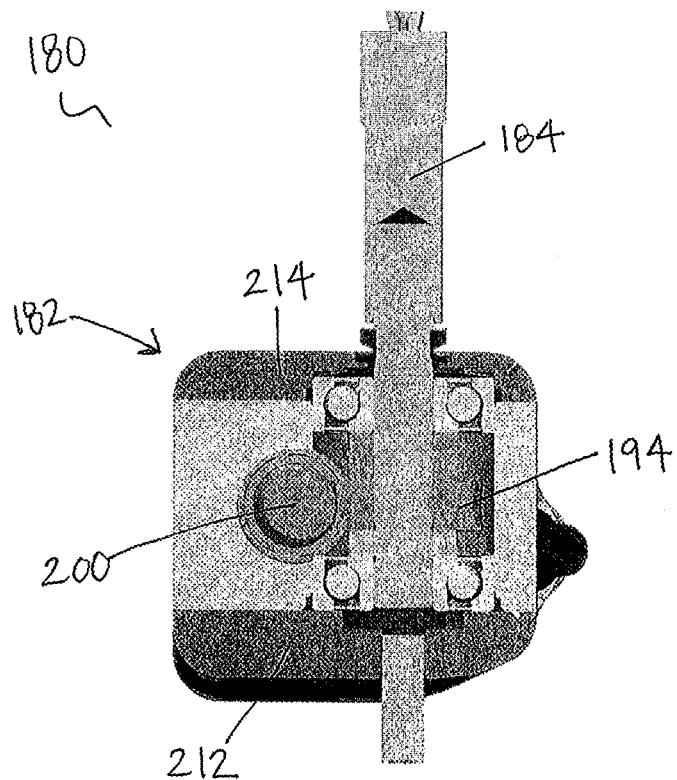
FIG. 7D is a front cross-sectional view of the yaw mechanism of FIG. 7A.

In one embodiment, as best shown in FIGS. 7B-7D, the structure 182 has a motor 184 rotatably coupled to the output shaft 184 via a series of gears such that the motor 184 can rotate the shaft 184. As best shown in FIG. 7B in which the housing of the structure 182 is not depicted, the gears in this exemplary implementation include a drive gear 188 rotationally constrained to the motor 186 and rotatably coupled to the driven gear 190. The driven gear 190 is rotationally constrained to a worm screw 192, which is threadably coupled to a worm wheel 194 such that rotation of the driven gear 190 causes rotation of the worm screw 192 and thus rotation of the worm wheel 194. The worm wheel 194 is rotationally constrained to the output shaft 184. As such, actuation of the motor 186 causes rotation of the drive gear 188, which rotates the driven gear 190, which rotates the worm screw 192, which rotates the worm wheel 194, which causes rotation of the output shaft 184. In one implementation, the gears can provide a total reduction that converts the high-speed motor output to the low speed and high torque required. Alternatively, other known gears or rotational elements may be used to cause the rotation of the output shaft 184.

The motor and drivetrain components can be supported and positioned within the structure 182 via various known mechanisms and features. Thus, the specific bearings, washers, spacers, and other components discussed below are exemplary and non-limiting. For example, in this embodiment, the output shaft 184 can be supported by two bearings 196A, 196B (e.g., opposing angular contact bearings) that can be flanged or capped to support the weight of the system. In addition, a retaining ring (not shown) can be provided that constrains the shaft axially against the bearings 196A, 196B. Torque can be transmitted from the worm gear 192 to the wheel 194 to the output shaft 184, for example with a key and keyway (not shown). The drive gear 188/driven gear 190 stage can protect the motor 186 from axial loads, while the intermediate parallel shaft 200 is supported against axial thrust on the worm with angular contact bearings 198A, 198B. The preload can be achieved with a disc spring 206 as shown, but other methods include the use of an axial wave or spring washers (not shown). Precision spacers 202 can be used to locate all bearing and gears on the shafts.

The gear train in one embodiment is disposed within the drivetrain housing 208. The worm screw bearing caps 210 retain the worm screw 192, the angular contact bearings 198, the spacers 202, and the disc spring 206 within the housing 208. As best shown in FIGS. 7C and 7D, the body 182 can have a baseplate 212 while the drivetrain housing 208 can have a top plate 214. Further, the motor 186, motor controller (not shown), and cabling (not shown) can be housed together within the motor housing 216. Further, the yaw mechanism structure (or "housing") 182 can be securely fastened to the pitch mechanism structure (not shown) using a pair of locating pins (not shown) and low-profile shoulder screws (not shown) or the like to better transmit torque and move the entire device.

The specific yaw mechanism structure 182 is only one example of an appropriate structure with appropriate internal components that can be used to create the desired yaw movement. Any other known structure and known internal mechanisms can be incorporated herein to accomplish the same movement.

Figure 8A:
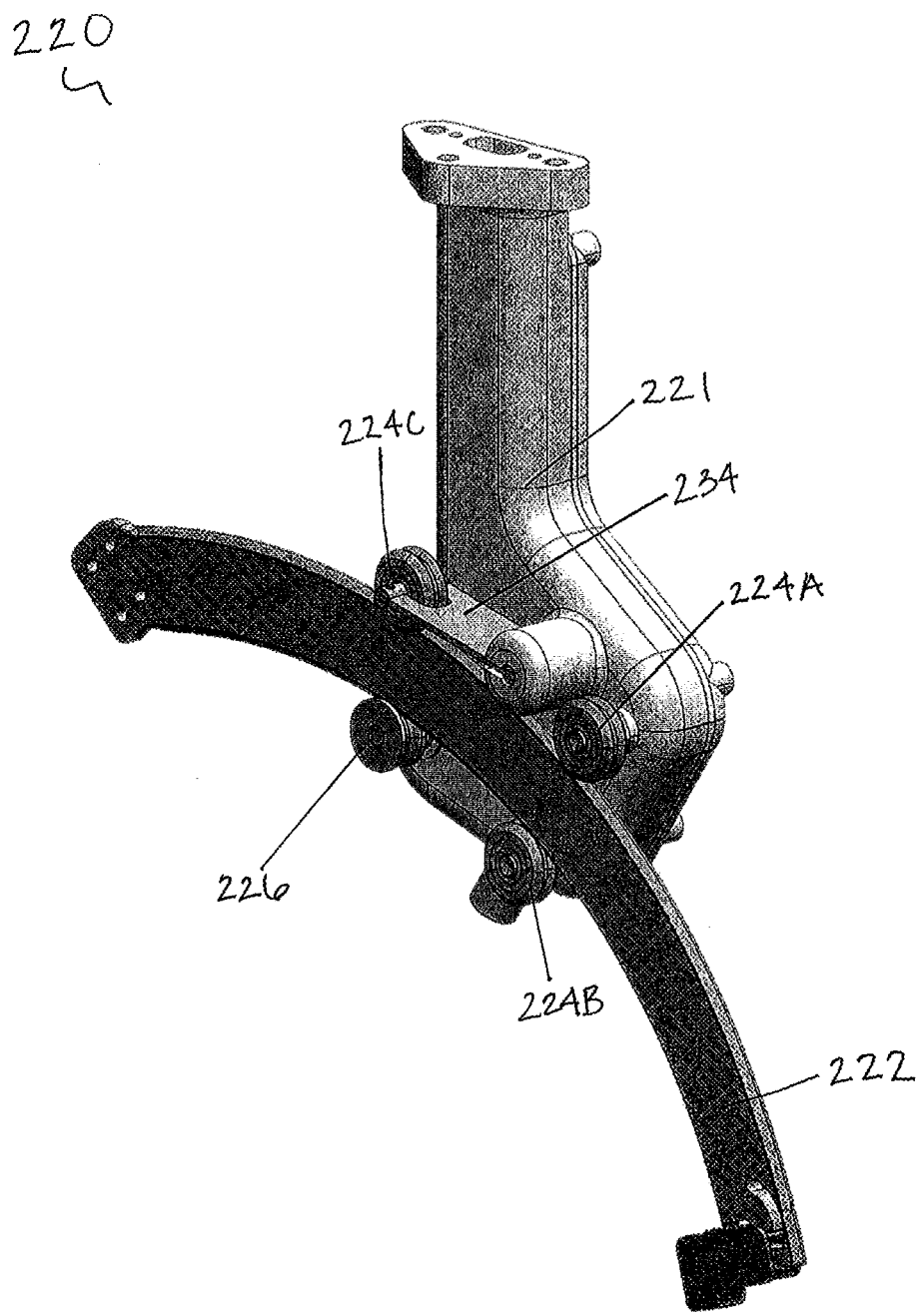
FIG. 8A is a perspective view of a pitch mechanism of a gross positioning system, according to one embodiment.
Figure 8B:
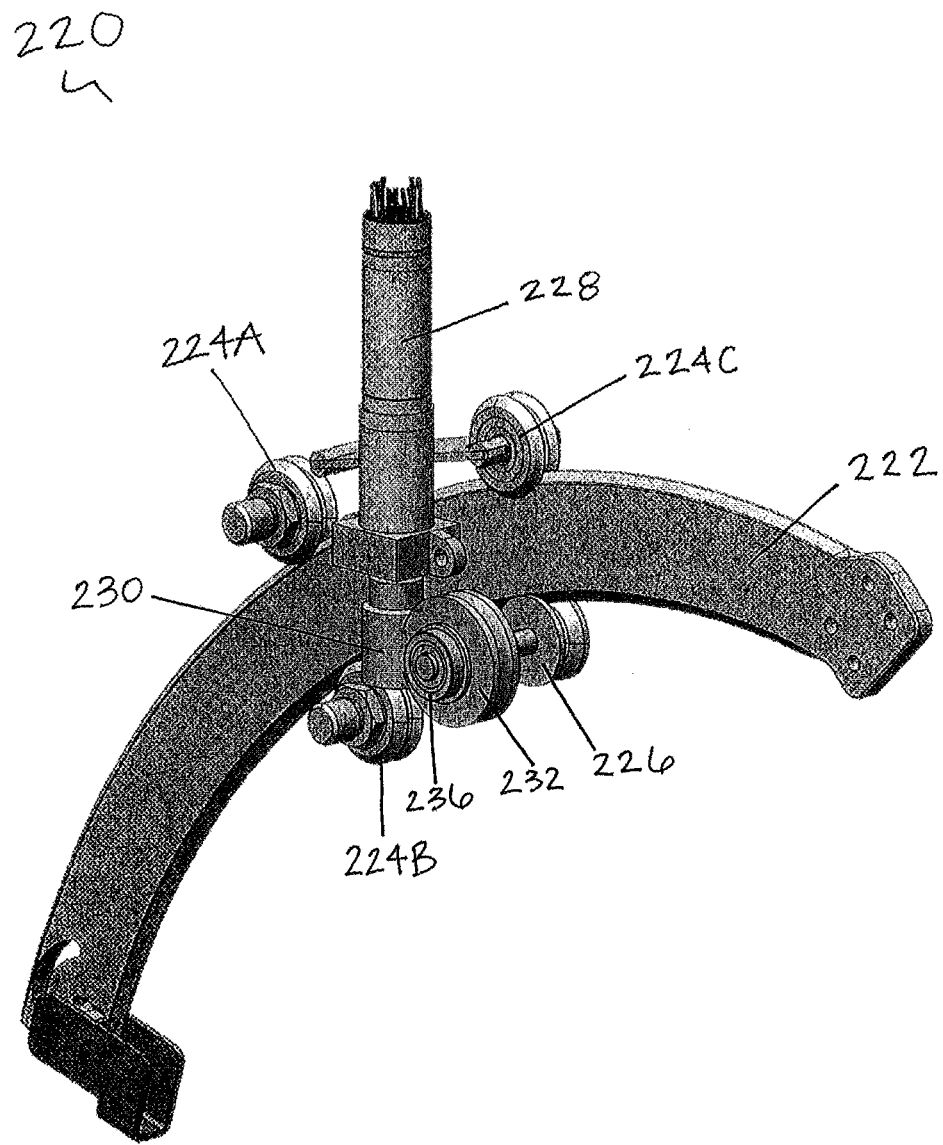
FIG. 8B is a detailed view of the components of the pitch mechanism of FIG. 8A.
Figure 8C:
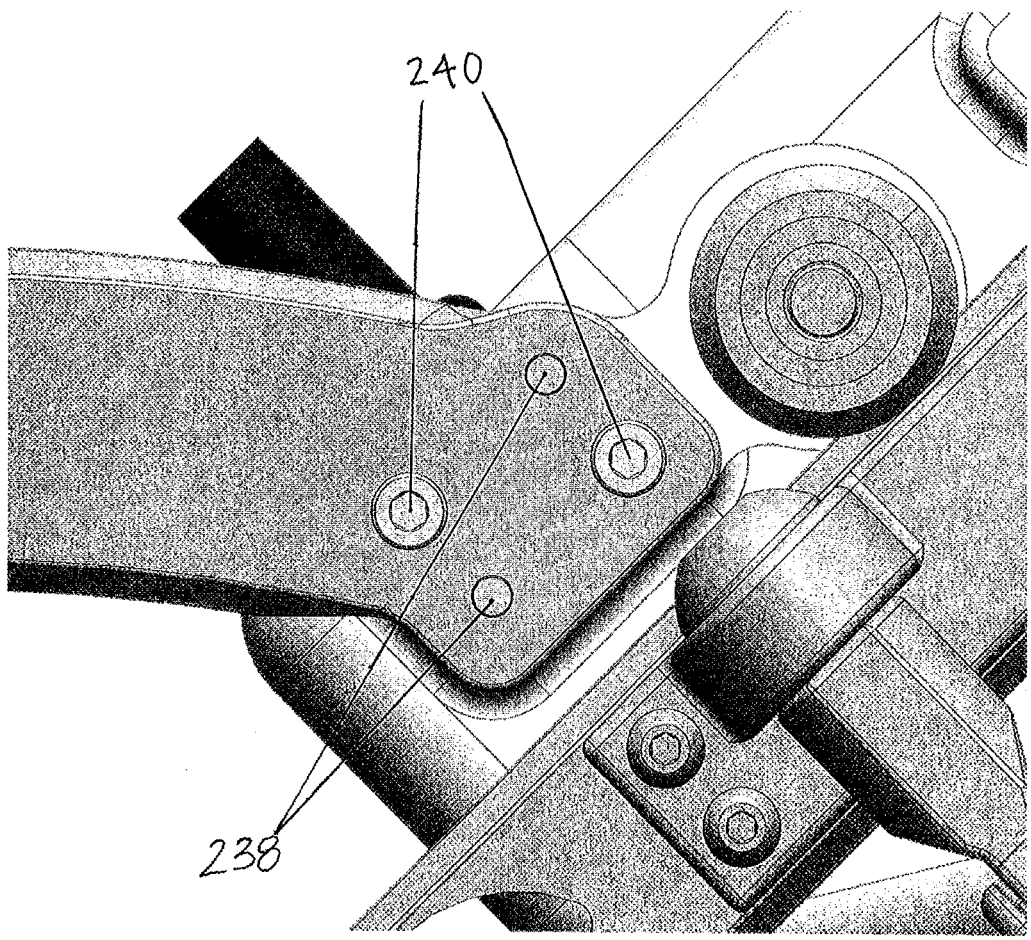
FIG. 8C is a detailed view of the rail of the pitch mechanism of FIG. 8A connected to a plunge mechanism.

FIGS. 8A-8C depict a pitch mechanism 220 (similar to joint 64 as discussed above), according to one embodiment. The mechanism 220 has a body 221 and a curved output rail 222 slidably coupled to the body 221 such that the pitch results from movement of the output rail 222 in relation to the body 221. The output rail 222 is an elongate curved structure 222 that, according to one embodiment, constitutes of segment of a circular arc. Further, the output rail 222 is slidably coupled to the pitch mechanism body 221 as described below and further is fixedly coupled at one end of the rail 222 to the plunge housing (as discussed elsewhere herein) such that movement of the rail 222 causes rotation of the plunge housing (and any attached robotic surgical device) about the RCM (not shown). The rail 222 can be a bar or any other elongate curved structure.

In one embodiment, the output rail 222 is coupled to the pitch mechanism body 221 via rotatable bearings 224 and a drive roller 226. In the specific implementation as shown, there are three bearings 224 (e.g., grooved rotatable bearings) and the drive roller 226 (e.g., a grooved friction-drive roller) that are positioned on either side of the rail 222 such that the rail 222 is in contact with each of the bearings 224 and the roller 226 and can be urged to move translationally by the drive roller 226 in relation to the bearings 224. Further, as described in additional detail below, two of the bearings 224A, 224B are positioned opposite each other, above and below the pitch rail 222. Additionally, a third bearing 224C is mounted on the end of a leaf spring 234 tensionably coupled to the body 221 such that the third bearing 224C is positioned above the rail 222 opposite of the drive roller 226. The leaf spring 234 may be deflected when the rail 222 is installed, which may result in a perpendicular preload force being applied to the roller 226 through the rail 222 as a result of the leaf spring 234. The friction between the roller 226 and the pitch rail 222 from this preload force engages the roller 226 with the pitch rail 222 (e.g., the edge of the rail 226) without slipping. Alternatively, any tensionable component or other mechanism can be used to apply sufficient force to the rail 226 or the drive roller 226 to ensure that the roller 226 engages the rail 222 without any slipping. Further, instead of the specific configuration of bearings 224A-224C and drive roller 226, any one or more known components that can allow for movement of the rail 222 in relation to the body 221 can be incorporated herein to accomplish the desired pitch movement.

As best shown in FIG. 8B (in which the body 221 housing is not shown), the drive roller 226 is actuated by a motor 228 that is rotatably coupled to the drive roller 226 and thus the output rail 222 via a series of rotational elements. It is understood that the specific rotational elements described with respect to this specific embodiment are exemplary, and any known rotational elements or other mechanisms and configurations thereof can be used. The rotational elements in this exemplary implementation include a drive gear 230 that is a worm screw 230 that is rotationally constrained to the motor 228 and threadably/rotatably coupled to a worm wheel 232. Alternatively, the drive gear 230 can be any type of gear or component coupled to any type of wheel 232 or similar component. The worm wheel 232 is rotationally constrained to the roller 226, which is rotatably coupled to the pitch rail 222 as described above. Thus, actuation of the motor 228 causes rotation of the drive gear 230, which causes rotation of the worm wheel 232, which causes rotation of the roller 226 and thus translation of the rail 222. In one implementation, the gears can provide a total reduction that converts the high-speed motor output to the low speed and high torque required.

In one embodiment, the shaft containing the worm wheel 232 and the rotatable roller 226 can be supported with two bearings 236 on opposing ends of the shaft, which are on opposing sides of the worm wheel 232. Alternatively, the supporting components can be any known components or mechanisms for supporting a set of gears in a drivetrain. The shaft may be disposed within the body 221. Further, in one embodiment, the motor 228, gear train, motor controller (not shown), and cabling (not shown) are also housed together in the body 221. Further, as discussed in detail below, the output rail 222 is fastened to the plunge housing with alignment pins 238 and screws 240, as best shown in FIG. 8C. Alternatively, the output rail 222 can be coupled to the plunge housing via any known coupling mechanisms or features.

FIGS. 9A-9B depict a plunge device or mechanism (similar to joint 66 as discussed above) 250, according to one embodiment. More specifically, FIG. 9A depicts a plunge mechanism structure (or "body" or "housing") 252 having an output rail 254 movably coupled to the structure 252 such that the plunge results from translational movement of the output rail 254 in relation to the structure 252 as a result of the structure 252 actuating the rail 254 to move. The output rail 254 is a substantially straight elongate structure 254 that is movably coupled to the plunge mechanism housing 252 as described below and further is fixedly coupled at one end of the rail 254 to the robot attachment clamp 256 such that movement of the rail 254 causes movement of any robotic device (not shown) disposed within the clamp 256, thereby translating the robotic device in and out of the port (or incision or opening) at the surgical site. The rail 254 can be a bar or any other elongate structure.

In one embodiment as best shown in FIG. 9B (in which the body 252 housing is not depicted), the output rail 254 is coupled to the plunge mechanism structure 252 via rotatable bearings 258A, 258B, 258C (e.g., three grooved bearings) and a drive roller 260 (e.g., a grooved friction drive roller). In the specific implementation as shown, the bearings 258A-C are positioned on either side of the rail 254 such that the rail 254 is in contact with each of the bearings 258A-C and can move translationally in relation to the bearings 258A-C. Two of the bearings 258A, 258B are positioned opposite each other on either side of the rail 254 at one end of the plunge mechanism structure 252. A third bearing 258C is coupled to a leaf spring 268 tensionably coupled to the body 221 opposite the roller 260 at a second end of the plunge mechanism structure 252. In some cases, a deflection in the leaf spring 268 may occur when the plunge rail 254 is installed, which may apply a preload force through the rail 254 perpendicularly against the roller 260 as a result of the leaf spring 268. The preload force and the friction created between the drive roller 260 and plunge rail 254 may enable the drive roller 260 to engage with the plunge rail 254 (e.g., the edge of the rail 254) without slipping. Alternatively, any tensionable component or other mechanism can be used to apply sufficient force to the rail 254 or the drive roller 260 to ensure that the roller 260 engages the rail 254 without any slipping. Further, instead of the specific configuration of bearings 258A-258C and drive roller 260, any one or more known components that can allow for movement of the rail 254 in relation to the body 252 can be incorporated herein to accomplish the desired plunge movement.

As best shown in FIG. 9B, according to one implementation, the drive roller 260 is actuated by a motor 262 that is rotatably coupled to the drive roller 260 and thus the output rail 254 via a series of rotational elements. It is understood that the specific rotational elements described with respect to this specific embodiment are exemplary, and any known rotational elements or other mechanisms and configurations thereof can be used. The rotational elements in this exemplary implementation include a drive gear 264 that is a worm screw 264 that is rotationally constrained to the motor 262 (e.g., at the output shaft of the motor 262) and threadably/rotatably coupled to a worm wheel 266. The worm wheel 266 is rotationally constrained to the roller 260, which is coupled to the edge of the plunge rail 254 by friction. Thus, actuation of the motor 262 causes rotation of the drive gear 264, which causes rotation of the worm wheel 266, which causes rotation of the roller 260 and thus translation of the rail 254. Alternatively, the actuation of rail 254 could be also be accomplished using a spur gear to engage with a rack attached to the plunge rail 254. In certain implementations, the gears can provide a total reduction that converts the high-speed motor output to the low speed and high torque required.

According to one embodiment, the shaft containing the worm wheel 266 and the roller 260 can be supported with two bearings 270 on opposing ends of the shaft, which are on opposing sides of the worm wheel 266. Alternatively, the supporting components can be any known components or mechanisms for supporting a set of gears in a drivetrain. The shaft may be disposed within the plunge housing 252. Further, in one embodiment, the motor 262, gear train, motor controller (not shown), and cabling (not shown) are also housed together in the plunge housing 252.

It is understood that alternative versions of these three yaw, pitch, and plunge joints can use any known mechanisms other than friction drive rollers. For example, each of the joints could use gears or be directly driven by a motor. In further alternatives, motion along the rails may not use gears, but may instead simply drive one of the support rollers to produce motion along the rail. In addition, hydraulic, pneumatic, or cable drives could be used in other known designs to produce the desired output motion.

Figure 10:
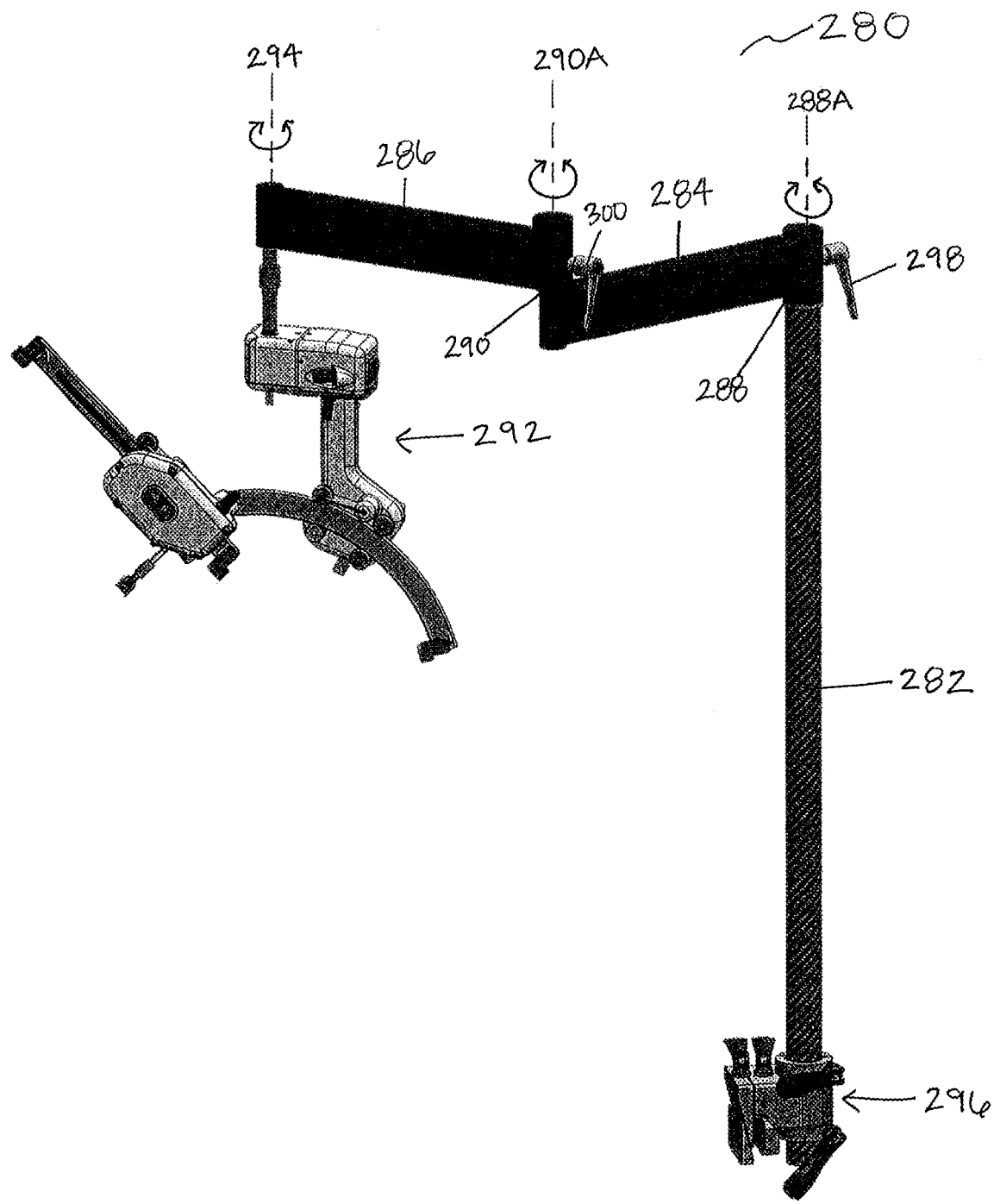
FIG. 10 is a robotic surgical device positioning system, according to one embodiment.

FIG. 10 depicts one embodiment of a robot support arm 280. In this implementation, the support arm 280 has a vertical (or "base column") rod 282, a first elongate arm 284 rotatably coupled to the rod 282 at a first rotatable joint 288, and a second elongate arm 286 rotatably coupled to the first arm 284 at a second rotatable joint 290. The first joint 288 has a first axis of rotation 288A and the second joint 290 has a second axis of rotation 290A such that the two axes of rotation 288A, 290A are vertically parallel. This allows for planar (X/Y directions) positioning of the gross positioning robotic device 292 with respect to the patient. In addition, the yaw axis 294 of the gross positioning robotic device 292 (similar to yaw axis 62 as discussed above) is also vertically parallel to the other two axes of rotation 288A, 290A.

The vertical positioning (Z direction) of the support arm 280 can be adjusted at the bed rail (not shown) using the clamp 296. The vertical rod 282 may be coupled with the clamp 296 before or after the clamp is attached to the bed rail. Once a vertical placement of the rod 282 has been selected, the gross positioning robotic device 292 can be docked or otherwise attached to the support arm 280. Then, the arm 280 can be horizontally positioned as needed, including throughout the robotic surgical device (not shown) insertion process. Once a final position for the robotic surgical device (not shown) has been selected, the gross positioning robotic device 292 is docked with the robotic surgical device (not shown). Typically, this is accomplished by locating the RCM approximately at the port/incision/opening. At this point, the support arm 280 can be locked into position using joint locks 298, 300.

Figure 11A:
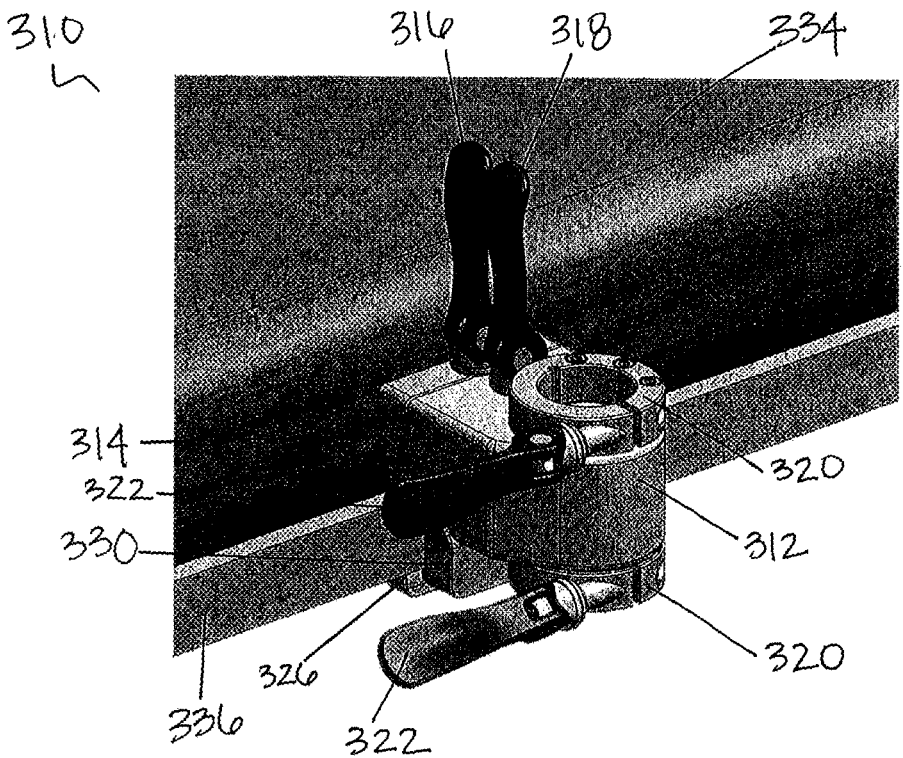
FIG. 11A is a detailed view of a clamping mechanism of a gross positioning system in an unlocked position, according to one embodiment.
Figure 11B:
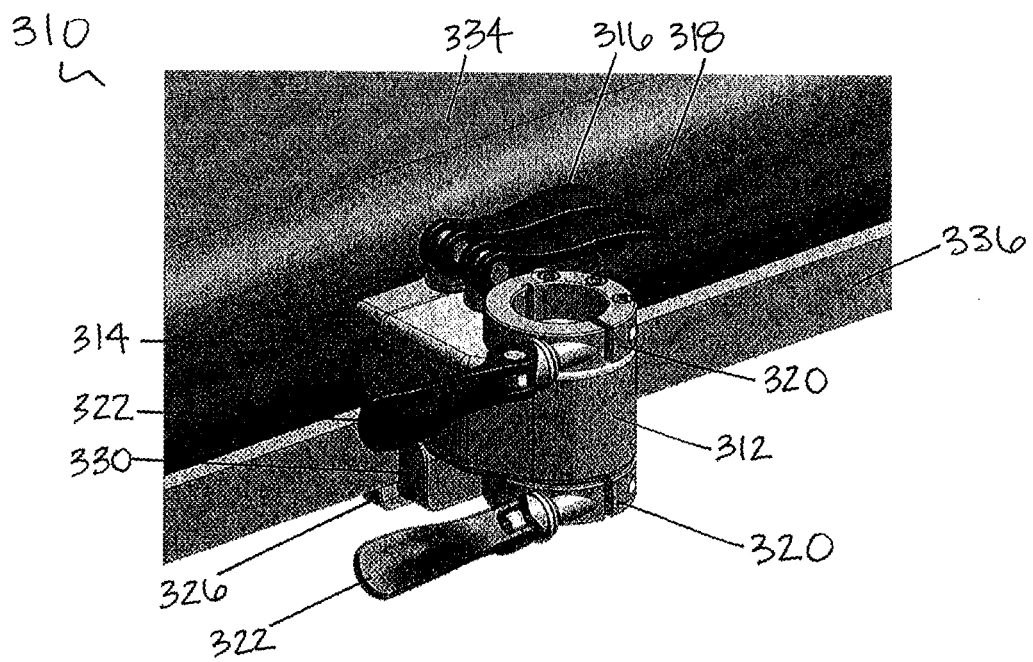
FIG. 11B is a detailed view of the clamping mechanism of FIG. 11A in a locked position.
Figure 11C:
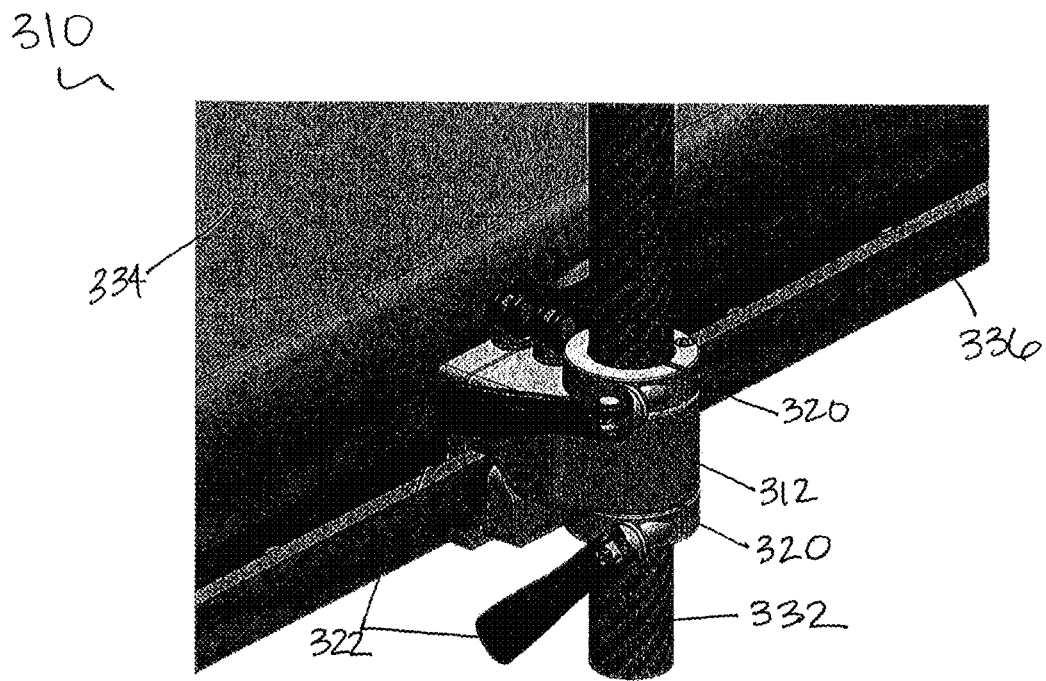
FIG. 11C is a detailed view of the clamping mechanism of FIG. 11A in a locked position and a support arm of the gross positioning system.
Figure 11D:
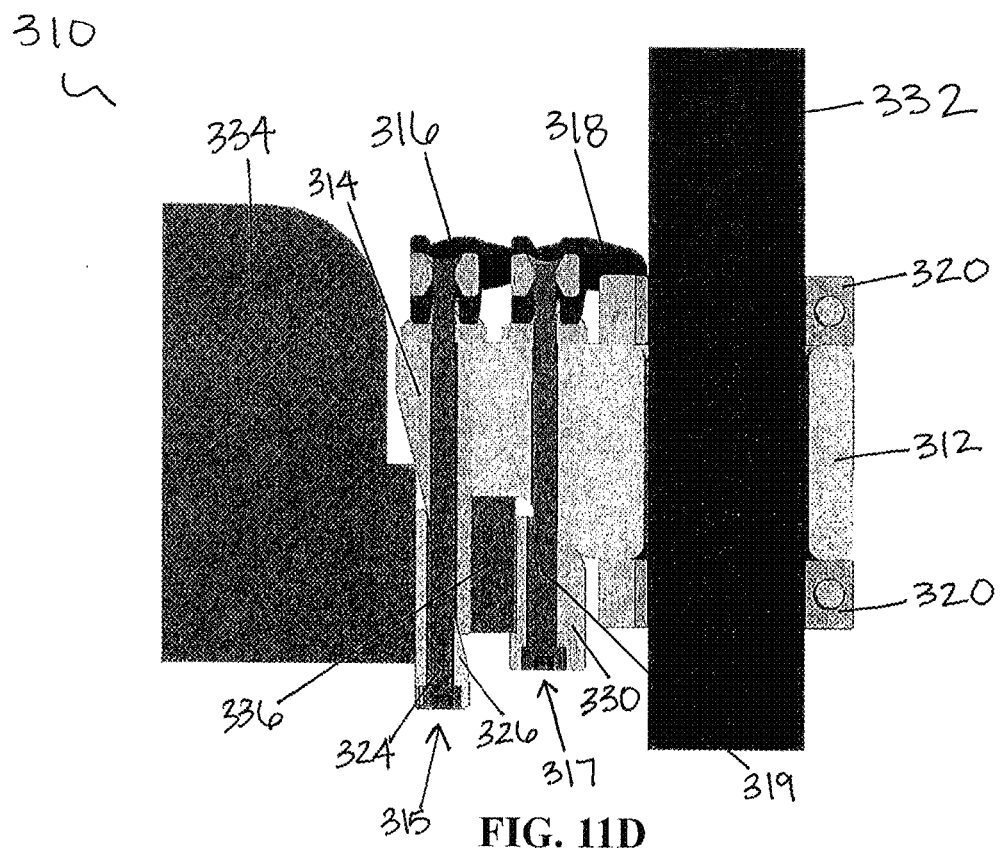
FIG. 11D is a cross-sectional view of the clamping mechanism of FIG. 11A in a locked position.

In one embodiment, a bed rail clamp 310 (similar to clamp 296, for example) is depicted in FIGS. 11A-11D. Loose or flexible bed rails have the potential to cause large deflections when using bed-mounted support arms, which act as cantilevered beams. To combat this, a robot support arm (such as arm 280) can be fastened to a standard surgical bed rail using the bed rail clamp 310. The clamp 310 has a clamp body 312 with two clamping shaft collars 320 coupled thereto, with one collar 320 on each end of the body 312, such that the clamp body 312 can receive the rod 332 of the support arm (similar to arm 280) and the collars 320 can secure the rod 332 thereto, as will be described in detail below. Further, as best shown in FIG. 11D, the clamp 310 can be securably attached to the bed rail 336 via the two attachment mechanisms 315, 317 attached to the clamp 310. The first or outer attachment mechanism 315 has an actuable bolt 324 that is actuated by the first handle 316 and is operably coupled to first and second wedges 314, 326. The first attachment mechanism 315 can be disposed between the rail 336 and the bed 334. The second or inner attachment mechanism 317 has an actuable bolt 319 that is actuated by the second handle 318 and is operably coupled to a clamping jaw 330. The second attachment mechanism 317 is disposed adjacent to the rail 336 on the outer face of the rail (opposite the first attachment mechanism 315.

In use, to secure the bed rail clamp 310 to the bed rail 336, the bed rail clamp 310 is positioned in relation to the rail 336 such that first attachment mechanism 315 is positioned between the rail 336 and the bed 334 while the second attachment mechanism 317 is positioned adjacent to the outer face of the rail 336. Once seated in the desired location, the handle 316 (e.g., a spreading clamp cam handle) can be urged into a down, locked position (as best shown in FIGS. 11B and 11D) to urge the actuable bolt 324 upward, thereby causing the bottom wedge 326 to be urged upward such that the angled face of the bottom wedge 326 engages with the angled face of the top wedge 314 such that the both wedges 326, 314 are urged laterally. As such, the bottom wedge 326 is urged against the bed 334 while the top wedge 314 is urged against the inner face of the rail 336, thereby tensionably securing the clamp 310 to the rail 336 and bed 334. After the handle 316 is in the locked position, the handle 318 (e.g., a rail clamp cam handle) can be urged into a down, locked position (as best shown in FIGS. 11B and 11D) to urge the actuable bolt 319 upward, thereby causing the clamp jaw 330 to move upward into contact with a bottom face of the rail 336, thereby securing the clamp 310 from shifting caused by forces applied to the vertical rod 332.

Once the bed rail clamp 310 is securely mounted to the bed 334, the rod 332 can be inserted through the clamping shaft collars 320 attached to the bed rail mount main body 312. As shown in FIG. 11C, the column clamp cam handles 322 are engaged in a locked position to secure the support column at the desired height by tightening the collars 320 around the rod 332. These column clamp cam handles 322 can be disengaged and re-engaged to allow the user to manually raise and lower the support arm column 332 as desired. It is understood that alternative methods for raising and lowering the support arm column can be used, such as the use of a hand crank or motor to adjust the height of the column via a leadscrew mechanism.

Figure 12:
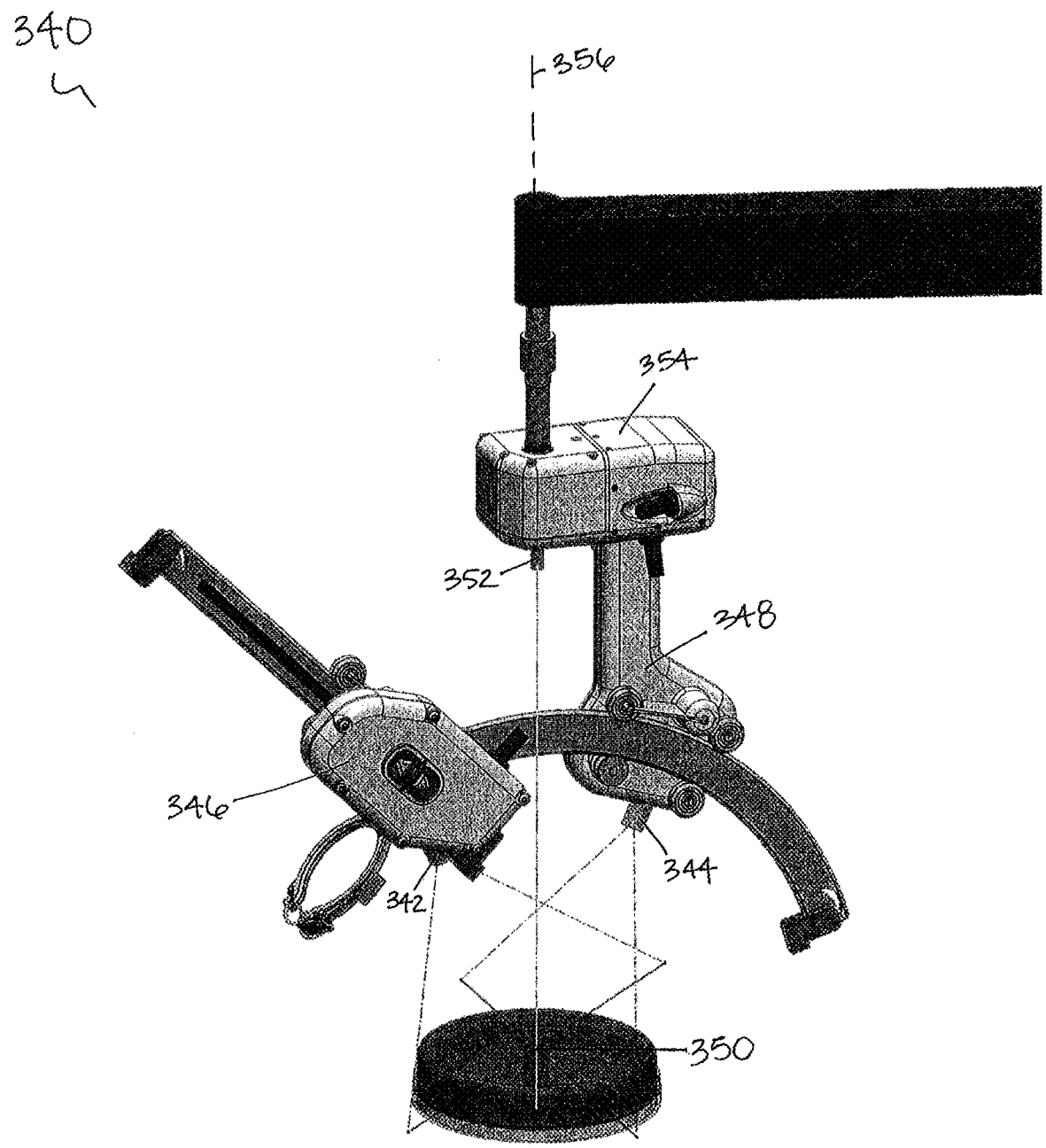
FIG. 12 is a robotic surgical device positioning system with lasers, according to one embodiment.
Figure 25:
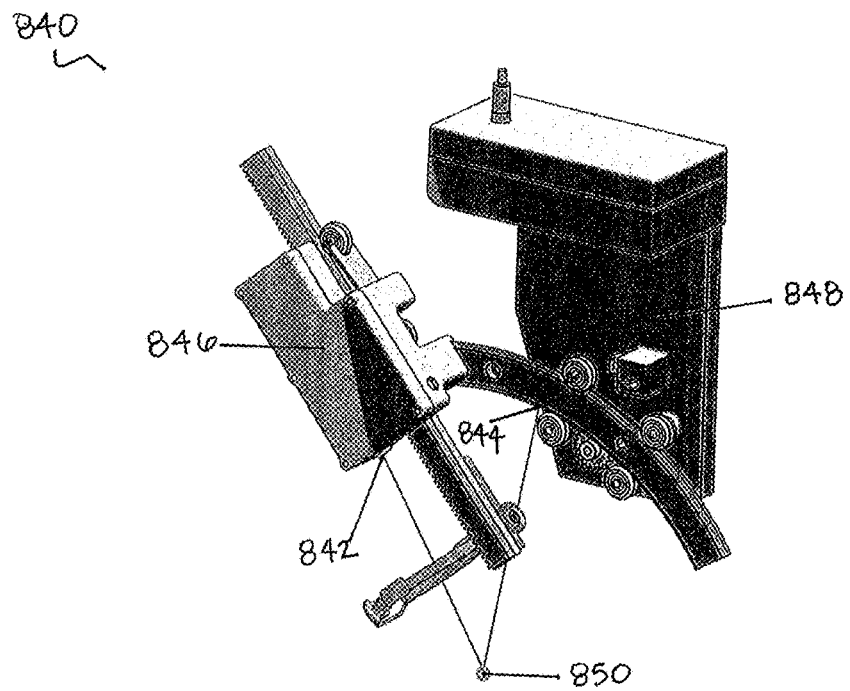
FIG. 25 is a robotic surgical device positioning system with lasers, according to one embodiment.

According to one alternative embodiment, any of the gross positioning robotic device embodiments herein can have an additional feature—laser-aided positioning. More specifically, one gross positioning robotic device 340 embodiment as shown in FIG. 12 has three line lasers 342, 344, 352 with one laser 342 disposed on the plunge housing 346, one laser 344 disposed on the pitch housing 348, and one laser 352 disposed on the yaw housing 354. The laser 352 may be mounted coaxially with the yaw axis 356. The lasers 342, 344, 352 are positioned and aimed to cause the laser light from each laser 342, 344, 352 to intersect at the RCM 350. Thus, in one embodiment, the lasers 342, 344, 352 can help with easy docking and positioning of the gross positioning robotic device 340, and the RCM 350 as shown by the lasers can easily be located at the patient incision/port/opening by the user. It is understood that alternative numbers of lasers may be used (such as, for example, two lasers as shown in FIG. 25). The various laser embodiments disclosed or contemplated herein can be incorporated into any gross positioning device embodiment disclosed herein.

Figure 13A:
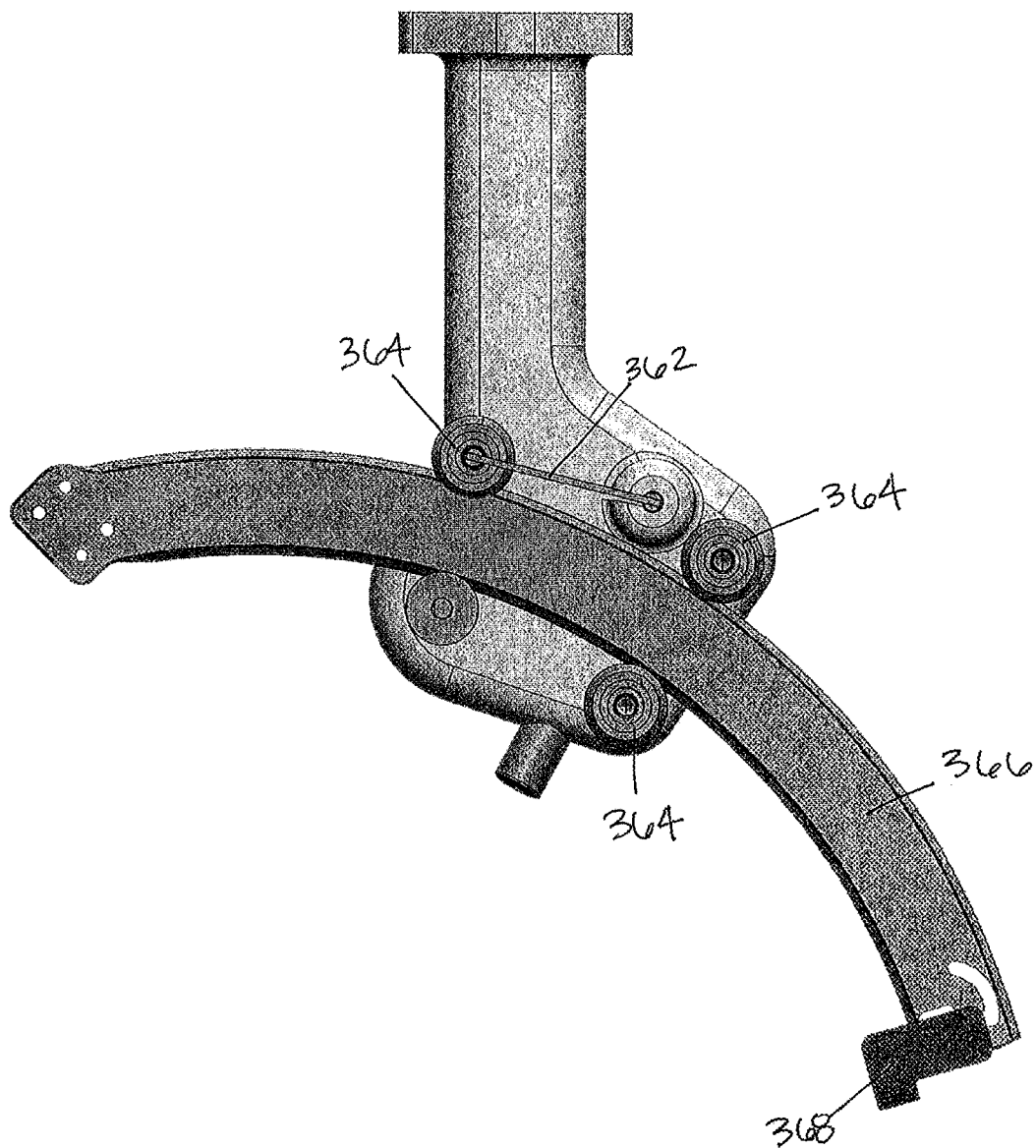
FIG. 13A is a perspective view of a pitch mechanism of a gross positioning system, according to one embodiment.
Figure 13B:
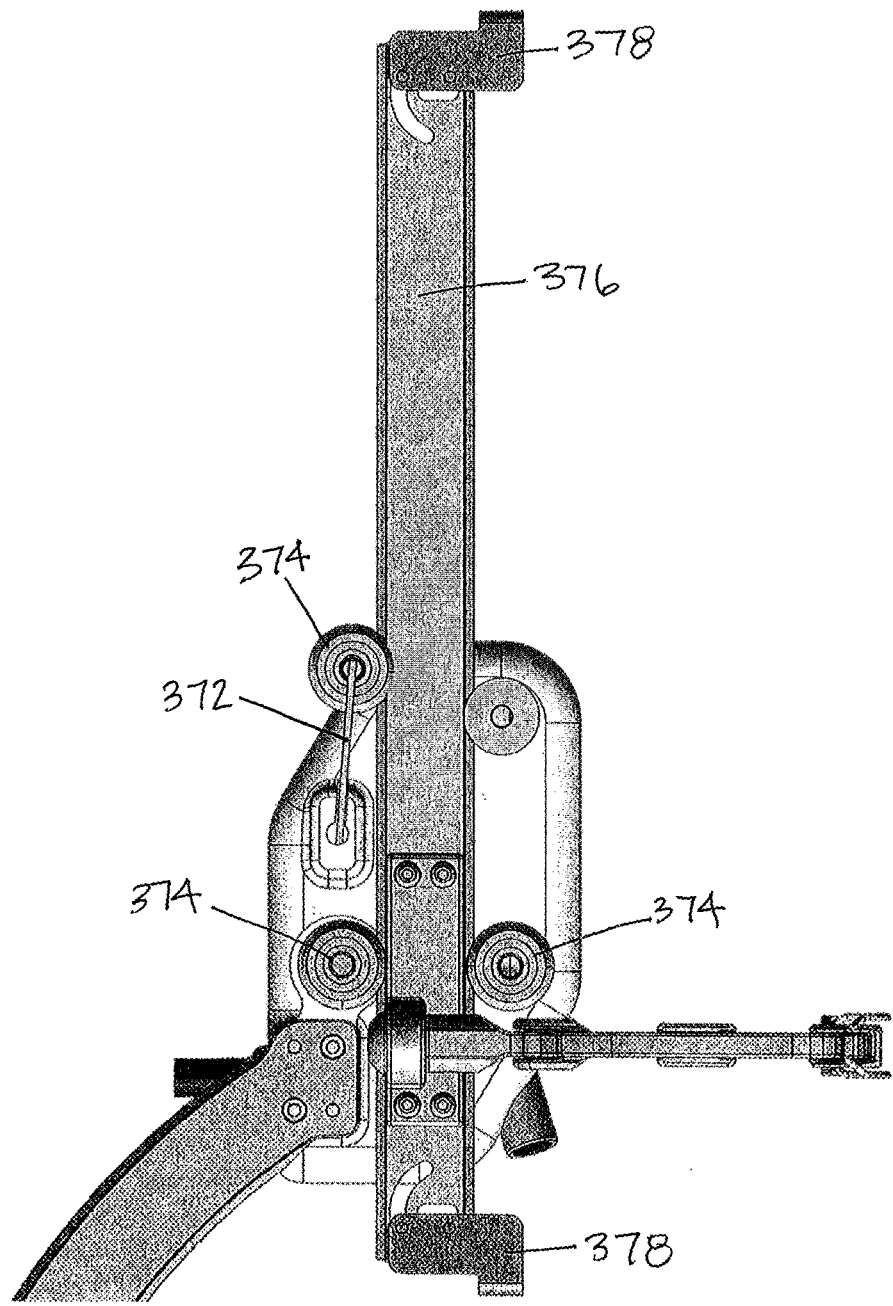
FIG. 13B is a perspective view of a plunge mechanism of a gross positioning system, according to one embodiment.

As shown in FIGS. 13A and 13B, and as discussed above with respect to FIGS. 8A and 9B, various implementations of the gross positioning device embodiments herein can also include tensioned mechanisms that provide tensioned force applied to at least one bearing of the pitch housing and/or the plunge housing to ensure contact of the bearings with the rails. More specifically, as shown in FIG. 13A, one exemplary embodiment of a pitch housing 360 has a leaf spring 362 that applies force to the bearing 364 that urges the bearing 364 into contact with the rail 366.

The leaf spring 362 can be manually de-tensioned or otherwise urged away from the rail 366, removing the bearing 364 from contacting the rail 366. This allows the rail 366 to be disengaged from the pitch housing 360. Additionally or alternatively, the pitch rail 376 includes a hard stop or "protrusion" 368. The toggleable protrusion 368 located at the end of the pitch rail 366 can be disengaged to allow for the rail 366 to be disengaged from the pitch housing 360. Then each subcomponent is easily disassembled as needed for cleaning and sterilization.

Similarly, as shown in FIG. 13B, one exemplary embodiment of a plunge housing 370 has a leaf spring 372 that applies force to the bearing 374 that urges the bearing 374 into contact with the rail 376. The leaf spring 372 can be manually de-tensioned or otherwise urged away from the rail 376, removing the bearing 374 from contacting the rail 376. This allows the rail 376 to be disengaged from the pitch housing 370. Additionally or alternatively, the plunge rail 376 includes a hard stop or "protrusion" 378. The toggleable protrusion 378 can be disengaged to allow the plunge rail 376 to be disengaged from the pitch housing 370. Then each subcomponent is easily disassembled as needed for cleaning and sterilization. It is understood that any known tensioning mechanism can be used in place of the leaf springs 362, 372 and any known toggleable mechanisms can be used in place of the protrusions 368, 378.

In a further alternative embodiment, any gross positioning robotic device as disclosed or contemplated herein can be controlled at the bedside using a local interface, such as a button (e.g., actuators 88, 90, 92) a joystick (not shown), a tablet, or any other known interface to drive each joint independently. The user can jog each joint individually or simultaneously with the interface. The gross positioning robotic device can be set aside while the robotic surgical device is inserted and then easily be introduced for docking when needed with this function. The interface can be intuitive, with the button or joystick articulation direction corresponding to the drive direction. To achieve this, the user interface can be localized at each joint or can be centrally located. For robot extraction, the robotic surgical device can be un-docked, and the gross positioning robotic device can be jogged out of the way.

Figure 14A:
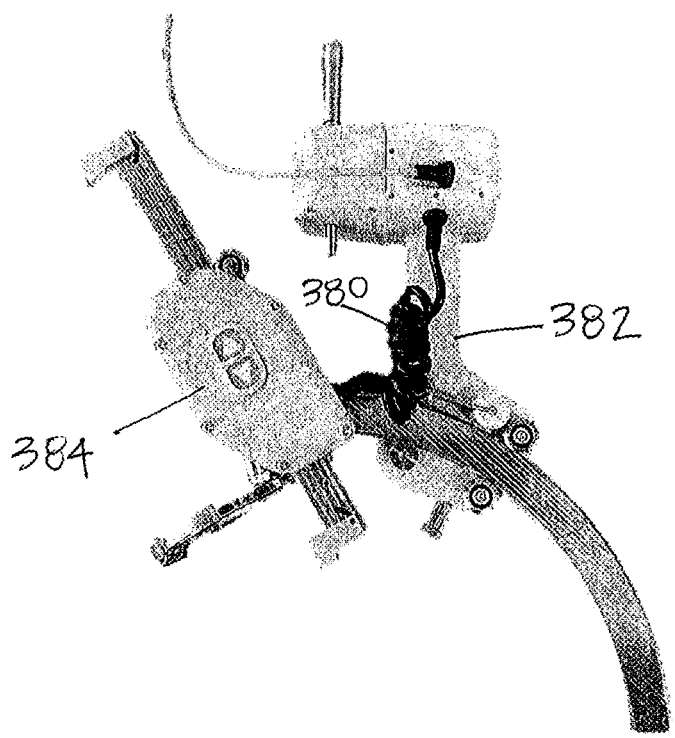
FIG. 14A is a perspective view of a gross positioning system, according to one embodiment.
Figure 14B:
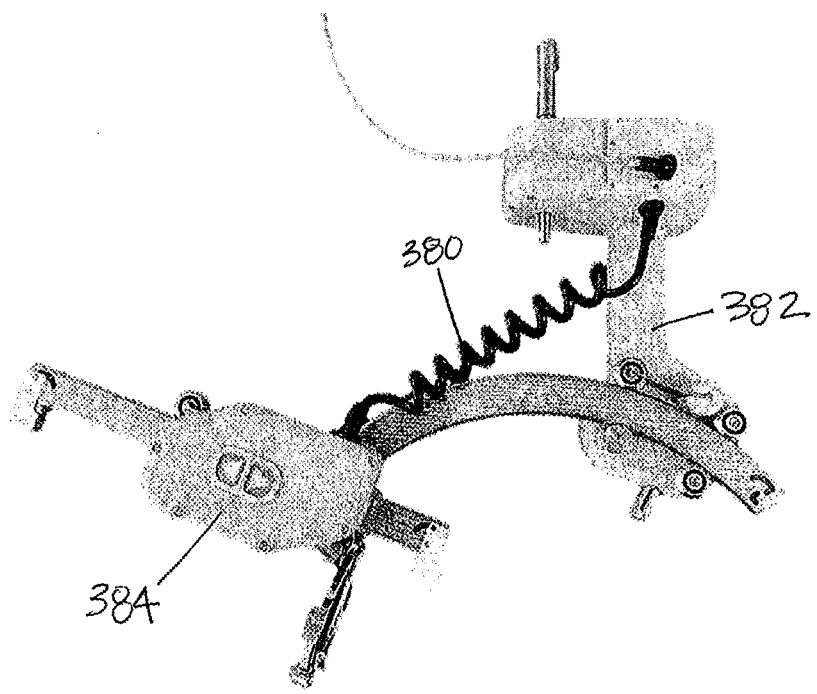
FIG. 14B is another perspective view of the gross positioning system of FIG. 14A.

FIGS. 14A and 14B depict another alternative feature of any gross positioning robotic device disclosed or contemplated herein: a coiled cable 380. In this embodiment, the cable 380 couples the pitch housing 382 to the plunge housing 384 as shown. The cable 380 is coiled to allow for the full range of pitch angles without cable entanglement by naturally retracting and extending as the pitch joint is pitched. In alternative designs, a slip ring or joint capsule could be used on any or all the joints. These designs could have continuous or very large ranges of motion.

Figure 15A:
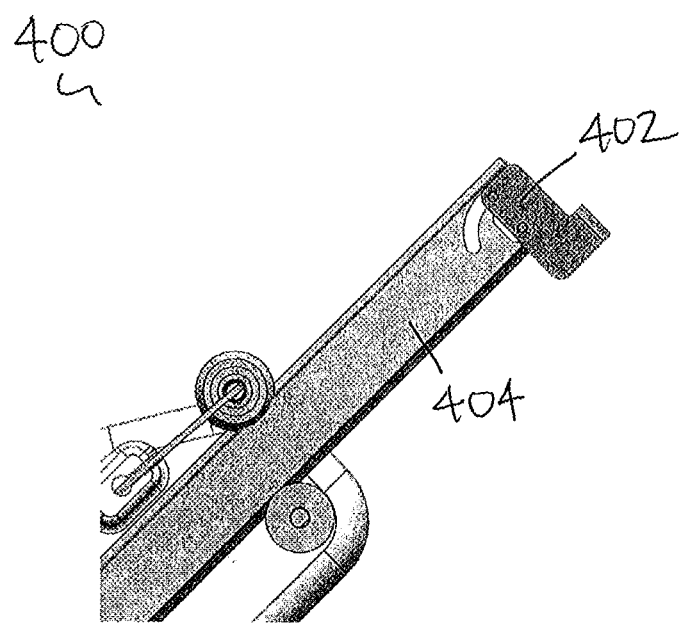
FIG. 15A is a detailed view of a rail of a plunge mechanism of a gross positioning system, according to one embodiment.
Figure 15B:
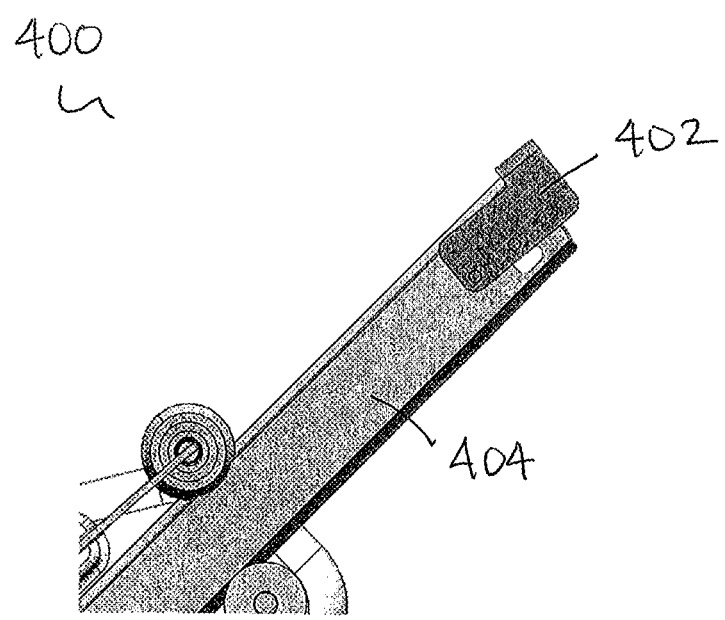
FIG. 15B is another detailed view of the rail of the plunge mechanism of FIG. 15A.

FIGS. 15A and 15B depict another alternative feature of any rail on any gross positioning robotic device disclosed or contemplated herein: a toggleable hard stop or "protrusion" 402. As shown, the hard stop 400 is positioned on the pitch output rail 404. The toggleable hard stop 402 is located at the end of the pitch rail 404 and can be disengaged to allow for the rail 404 to be disengaged from the pitch housing. FIG. 15A shows the hard stop 402 in an engaged position such that the rail 404 cannot be disengaged from the pitch housing. FIG. 15B shows the hard stop 402 toggled from FIG. 15A, and the hard stop 402 is in a disengaged position such that the rail 404 can be disengaged from the pitch housing It is understood that a hard stop can also be positioned on a plunge output rail as shown above in FIG. 13A.

Figure 16:
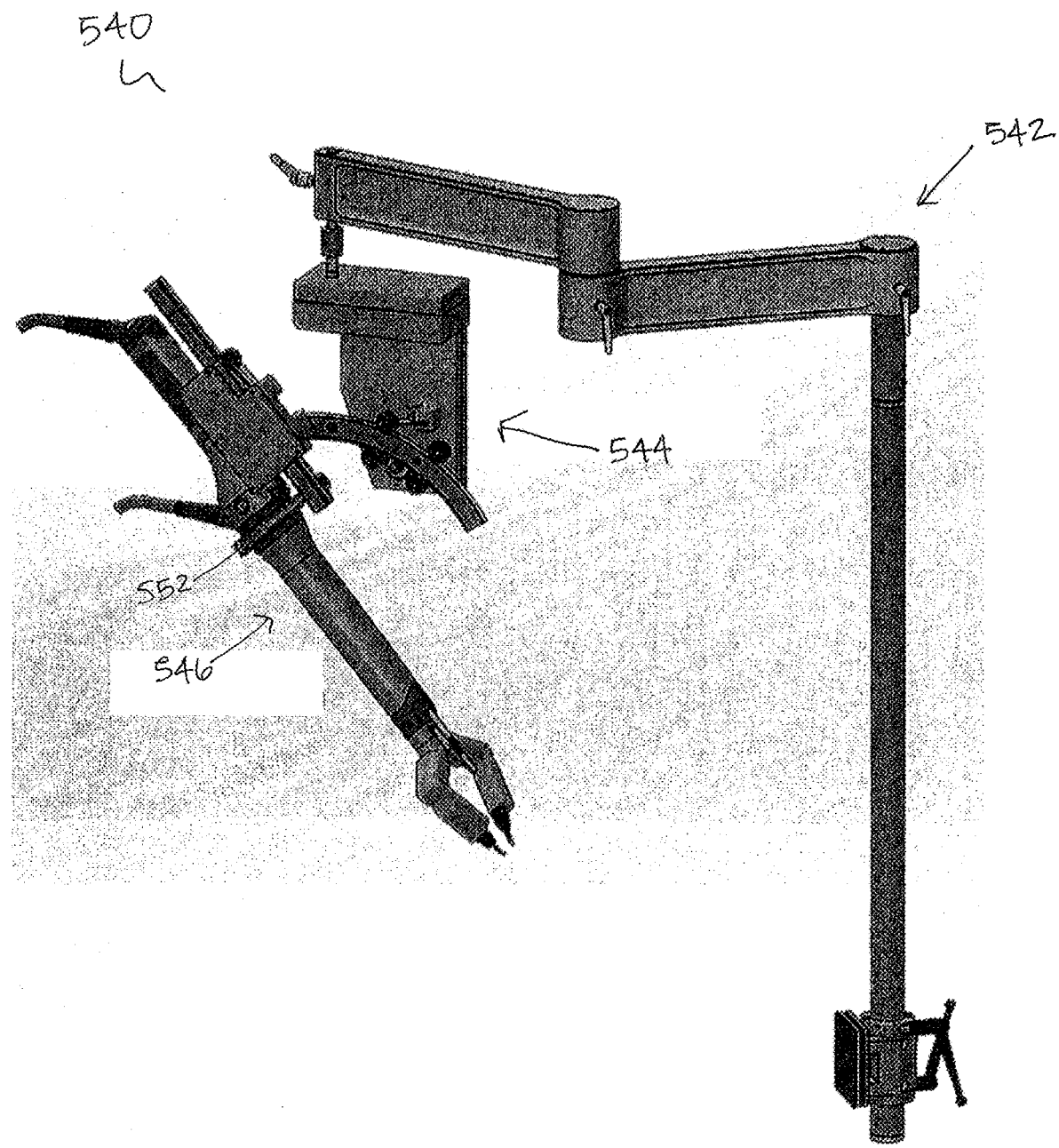
FIG. 16 is a perspective view of a robotic surgical device positioning system coupled to an in vivo robotic device, according to one embodiment.

Another embodiment of a robotic surgical device positioning system 540 is depicted in FIG. 16. It is understood that the various embodiments as disclosed in FIGS. 16-23 are substantially similar to the device implementations disclosed or contemplated above in FIGS. 2A-15B, with substantially similar components, features, and functions, except as expressly discussed herein.

The system 540 in FIG. 16 includes a passive support arm 542 and a gross positioning robotic device 544 rotatably coupled to the arm 542. Further, any known robotic device 546, which in this specific exemplary implementation is represented by the device 546 as shown, can be removably coupled to the device 544 such that the device 546 is disposed through an opening, orifice, incision, or port into the target cavity of the patient.

Figure 17A:
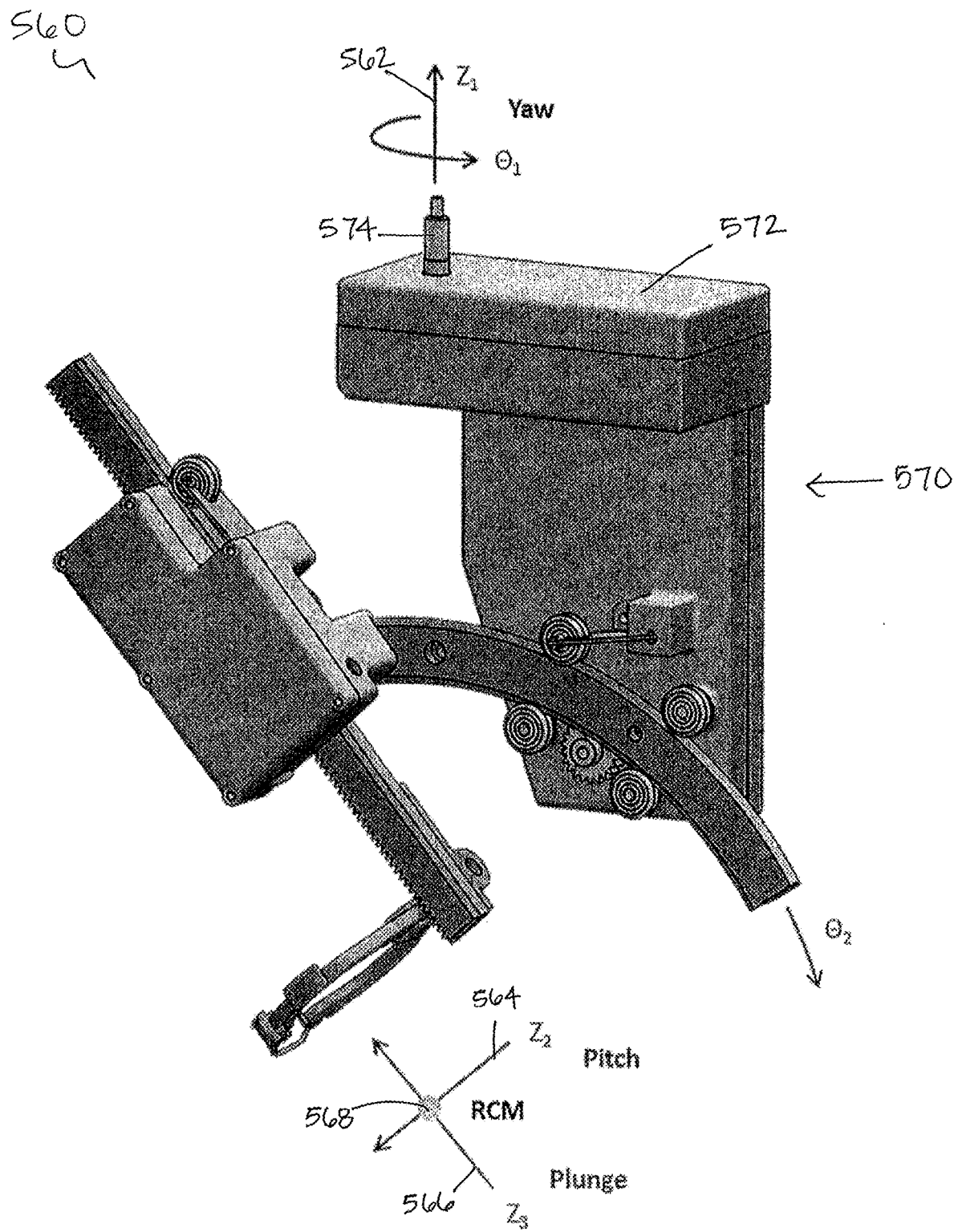
FIG. 17A is a detailed perspective view of a gross positioning system, according to one embodiment.
Figure 17B:
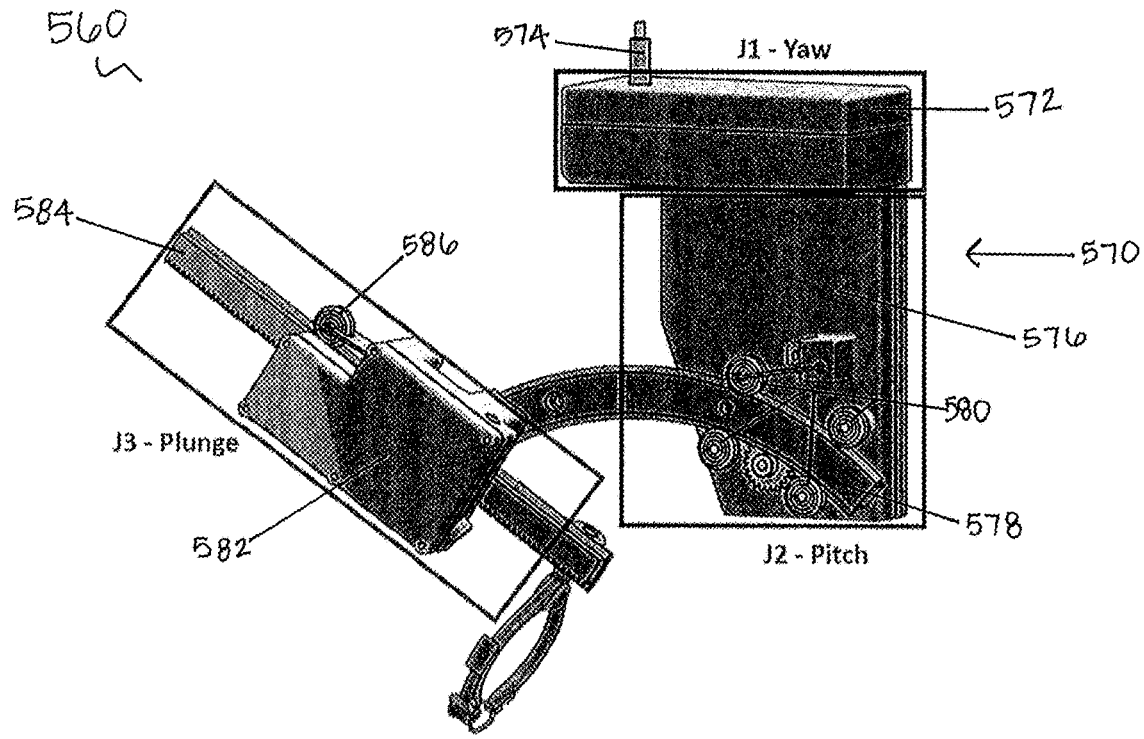
FIG. 17B is another detailed perspective view of the gross positioning system, according to one embodiment.

According to another embodiment of a gross positioning robotic device 560 as shown in FIGS. 17A and 17B, the device 560 has three joints: yaw (joint 1) 562, pitch (joint 2) 564, and plunge (joint 3) 566. Yaw 562 and pitch 564 rotate about the RCM, and the plunge 566 moves through the RCM 568. In this embodiment, each joint is fully decoupled and is controlled independently. Further, in certain embodiments, motors and motor controllers (not shown) are co-located at each joint 562, 564, 566. In addition, it is understood that each joint 562, 564, 566 can be, but does not have to be, backdriveable.

The yaw joint 562 originates from the body 570 of the gross positioning device 560, and more specifically in the yaw mechanism structure 572. More specifically, a rotatable yaw output shaft 574 extends from the yaw mechanism structure 572 and constitutes the yaw joint 562. As such, rotation of the output shaft 574 creates the yaw at the yaw joint 562.

The pitch joint 564 also originates from the body 570 of the device 560, and more specifically in the pitch mechanism structure 576. More specifically, an output rail 578 is operably coupled to the pitch mechanism structure 576 via rotatable bearings 580 such that movement of the output rail 578 in relation to the pitch mechanism structure 576 (as described in detail below) creates the pitch joint 564. As such, actuation of the output rail 578 creates the pitch at the pitch joint 564.

The plunge joint 566 originates from the plunge mechanism structure 582, which is operably coupled to the output rail 578. More specifically, an extendable rail 584 is operably coupled to the plunge mechanisms structure 582 via rotatable bearings 586 (as best shown according to one example in FIGS. 22A and 22B below). As such, extension of the extendable rail 584 creates the plunge at the plunge joint 566.

Figure 18A:
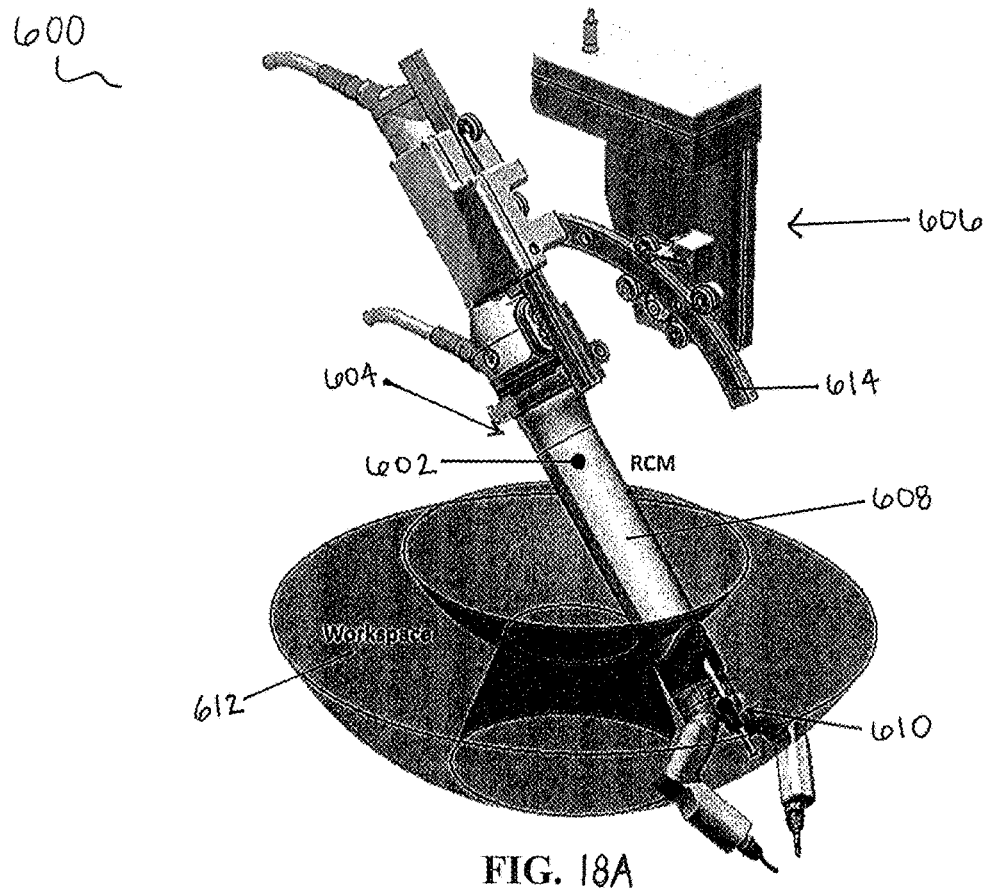
FIG. 18A is a detailed perspective view of the workspace of a gross positioning system coupled to an in vivo robotic device, according to one embodiment.
Figure 18B:
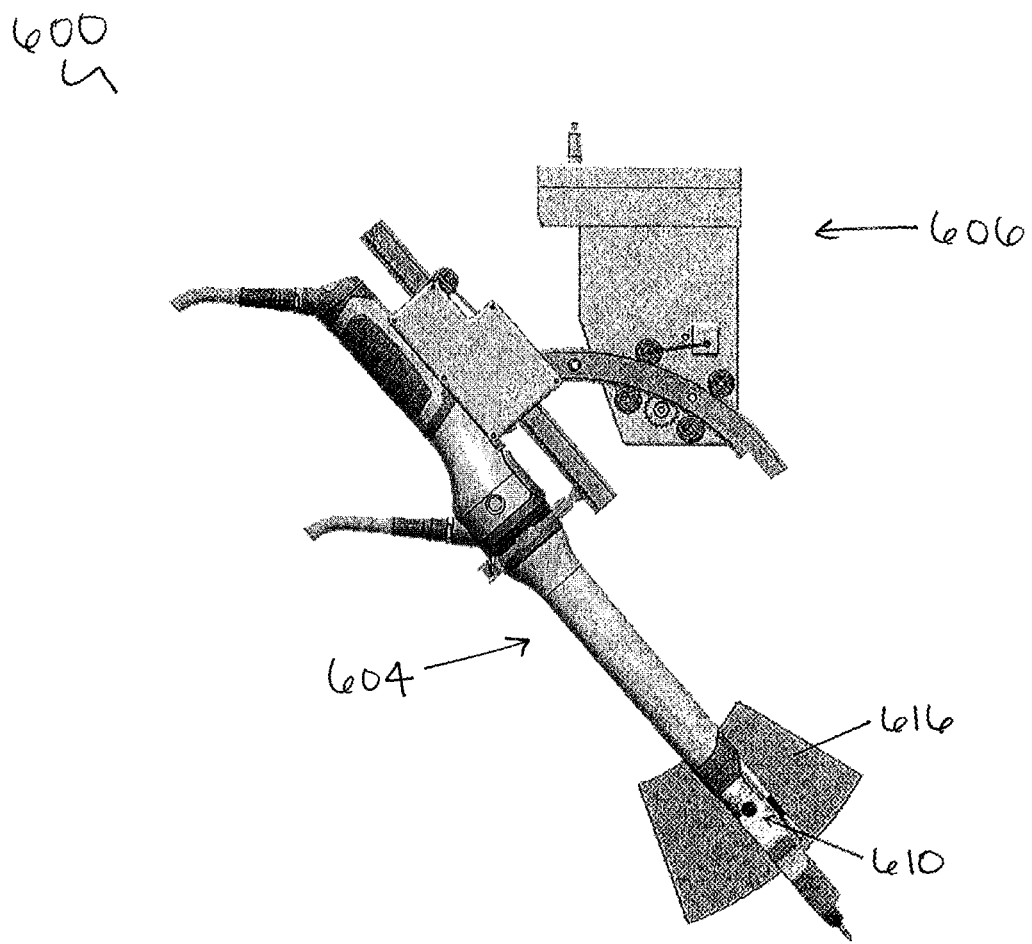
FIG. 18B is a detailed side view of a cross section of the workspace of a gross positioning system coupled to an in vivo robotic device of FIG. 18A.

As best shown in FIGS. 18A and 18B, another implementation of a device positioning system 600 has an RCM 602 that is located at the center of the circular arced rail 614. Alternatively, the RCM 602 can be disposed in any known position in relation to the gross positioning device. When a robotic surgical device—such as device 604—is docked (or otherwise coupled) to the gross positioning robotic device 606, the RCM 602 is within the elongate body (or tube) 608 of the device 604 and approximately colinear with its kinematic origin 610. FIG. 18A also depicts the workspace 612 of the gross positioning device 606 in the context of the robotic surgical device 604. The kinematic origin 610 of the robotic device 604 is shown. The gross positioning device 606 can be used to move the kinematic origin 610 to any location within the toroidal workspace 612. The cross-section of the workspace 612, which is governed by pitch and plunge, is an annulus sector 616 as best shown in FIG. 18B.

Returning to FIG. 18A, the yaw joint (such as joint 562 as discussed in detail above with respect to FIG. 17A) is a rotational joint and can be articulated over a sweep angle of at least 165 degrees. In the embodiment of FIG. 18A, the workspace 612 depicts yaw with 360 degrees of travel, meaning it can rotate endlessly in either direction (as cabling adjustment permits). The pitch joint (such as joint 564 as discussed in detail above with respect to FIG. 17A) allows rotation about the RCM 602 with motion along the output rail 614. For pitch, according to certain implementations, a 40-degree arc can be traversed, with pitch angles approximately between 20 and 60 degrees from vertical. In addition, the plunge joint (such as joint 566 as discussed in detail above with respect to FIG. 17A) is a translational joint and can be translated a total length of at least 100 cm, according to various embodiments.

Figure 19A:
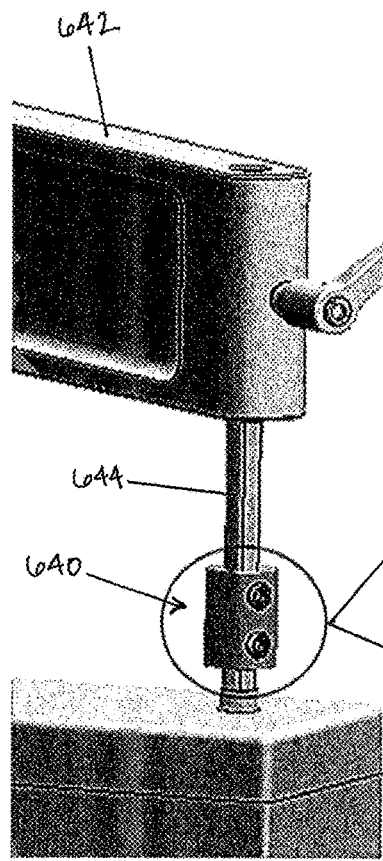
FIG. 19A is a perspective view of a yaw mechanism and the support arm of a gross positioning system, according to one embodiment.
Figure 19B:
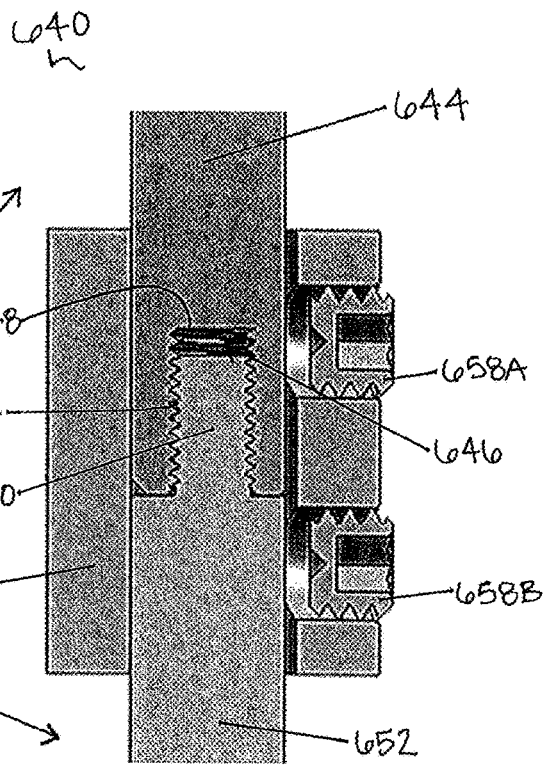
FIG. 19B is an exploded cross-sectional view of the yaw mechanism of a gross positioning system of FIG. 19A.

FIGS. 19A and 19B depict one exemplary embodiment of an output shaft 640 for a yaw joint. FIG. 19A depicts a perspective view of the shaft 640, while FIG. 19B shows an exploded cross-sectional view. As best shown in FIG. 19A, the output shaft 640 is coupled with the robot support arm 642. In this specific implementation, the output shaft 640 is a threaded D-shaft 640. The upper section 644 of the shaft 640 has a female connection opening 646 with threads 648 defined therein that are coupleable with the male connection protrusion 650 of the lower section 652 with threads 654 defined thereon. The coupled threads 648, 654 support the weight of the device(s). A shaft coupler 656 is disposed around the shaft 640 and has locking set screws 658A, 658B that allow the transmission of torque without unscrewing the two sections 644, 652 of the shaft 644. Alternatively, other known quick connection mechanisms can be used for easy docking and undocking of the gross positioning robotic device 660 to the robot support arm 642, such as for cleaning and sterilization.

Figure 20A:
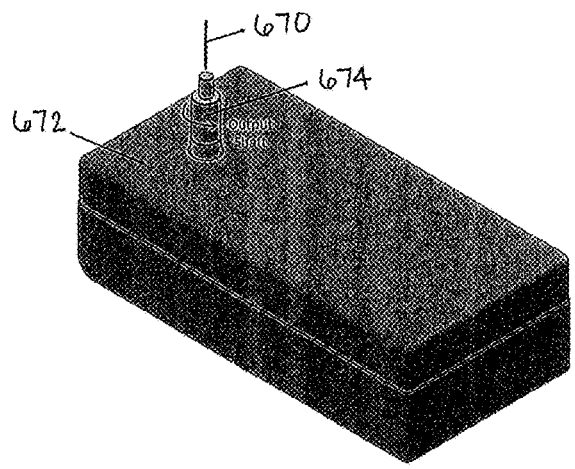
FIG. 20A is a perspective view of a yaw mechanism of a gross positioning system, according to one embodiment.

FIGS. 20A-20D depict the internal mechanisms of a yaw joint (such as joint 562 as discussed above) 670, according to one embodiment. More specifically, FIG. 20A depicts a yaw mechanism structure 672 having an output shaft 674 rotatably extending from the structure 672 such that the yaw joint 670 originates from the output shaft 674. The output shaft 674 rotates to cause the gross positioning robot (not shown) to rotate in relation to the robot support arm (not shown).

Figure 20B:
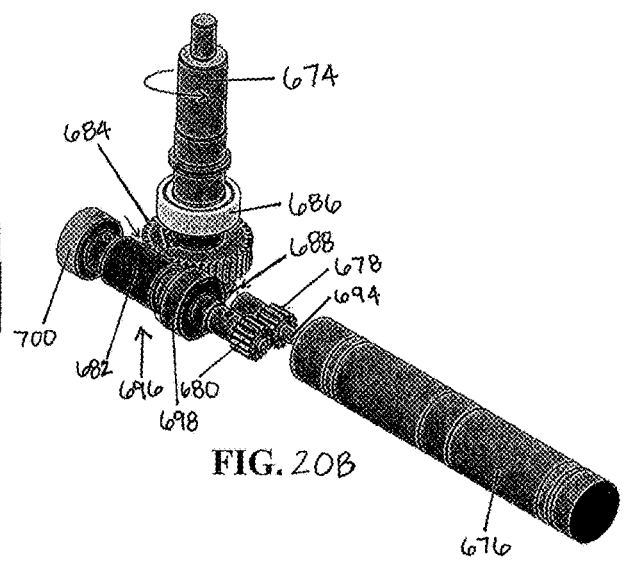
FIG. 20B is a detailed view of the components of the yaw mechanism of FIG. 20A.
Figure 20C:
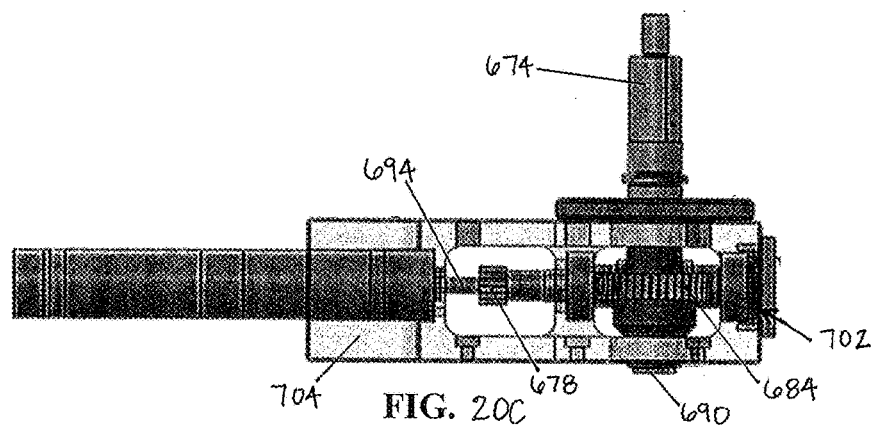
FIG. 20C is a side detailed view of the components of the yaw mechanism of FIG. 20A.
Figure 20D:
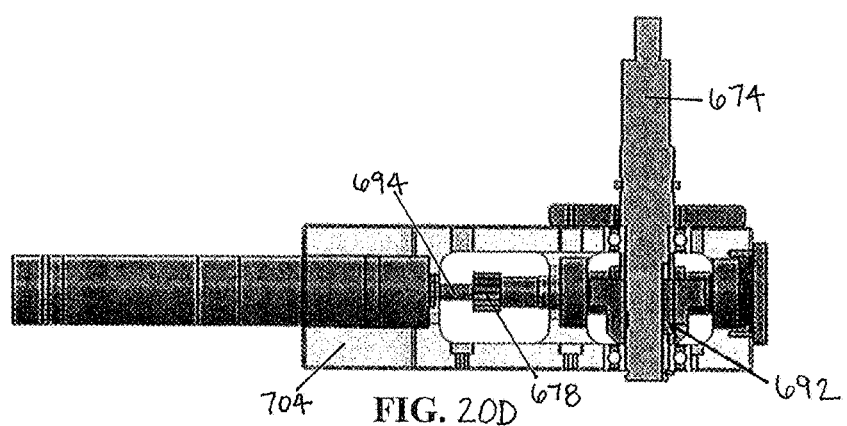
FIG. 20D is a side cross-sectional view of the yaw mechanism of FIG. 20A.

In one embodiment, as best shown in FIGS. 20B-20D, the output shaft 674 is actuated by a motor 676 that is rotatably coupled to the output shaft 674 via a series of rotational elements. The gears include a drive gear 678 rotationally constrained to the motor 676 and rotatably coupled to the driven gear 680. The driven gear 680 is rotationally constrained to a worm screw 682, which is threadably coupled to a worm wheel 684 such that rotation of the driven gear 680 causes rotation of the worm screw 682 and thus rotation of the worm wheel 684. In one implementation, the gears provide a total reduction of 5000:1, converting the high-speed motor output to the low speed and high torque required. The output shaft 674 is supported by two bearings 686, 688 that can be flanged or capped to support the weight of the system. In addition, a retaining ring 690 can be provided that constrains the shaft axially against the bearings 686, 688. Torque is transmitted from the worm gear 682, 684 to the output shaft 674 with a key and keyway 692. The drive gear 678/driven gear 680 stage protects the motor output shaft 694 from axial loads, while the intermediate parallel shaft 696 is supported against axial thrust on the worm with preloaded angular contact bearings 698, 700. The preload can be achieved with an axial wave spring 702 as shown, but other methods include the use of spring washers or disk springs (not shown). Spacers (not shown) can be used to locate all bearing and gears on the shafts. The gear train in one embodiment is disposed within a motor block 704. The assembled motor block 704, motor controller (not shown), and cabling (not shown) can be housed together. Further, the yaw mechanism structure (or "housing") 672 can be securely fastened to the pitch mechanism structure (not shown) using shoulder bolts or the like to better transmit torque and move the entire device.

Figure 21A:
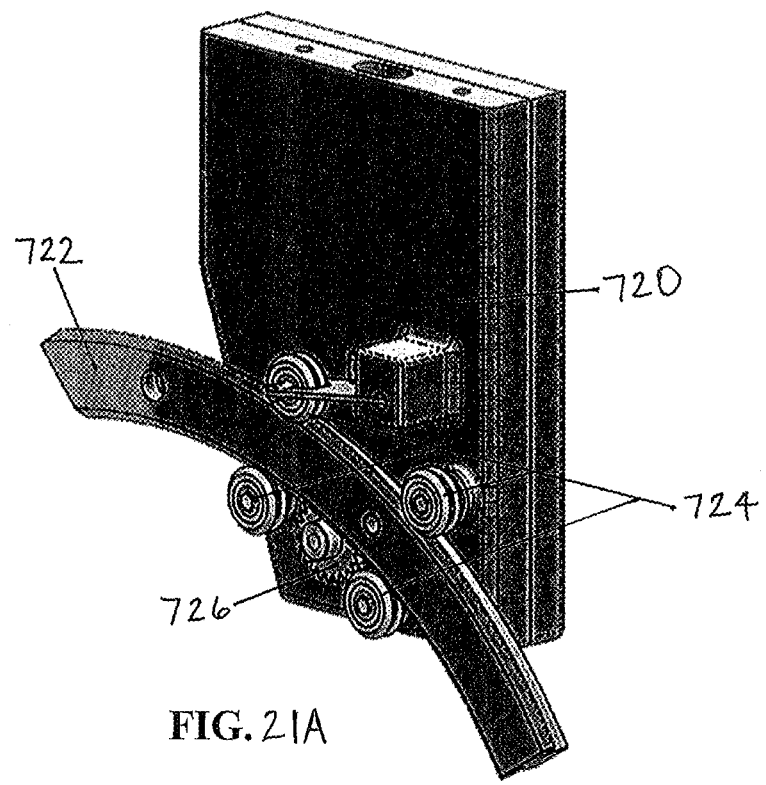
FIG. 21A is a perspective view of a pitch mechanism of a gross positioning system, according to one embodiment.
Figure 21B:
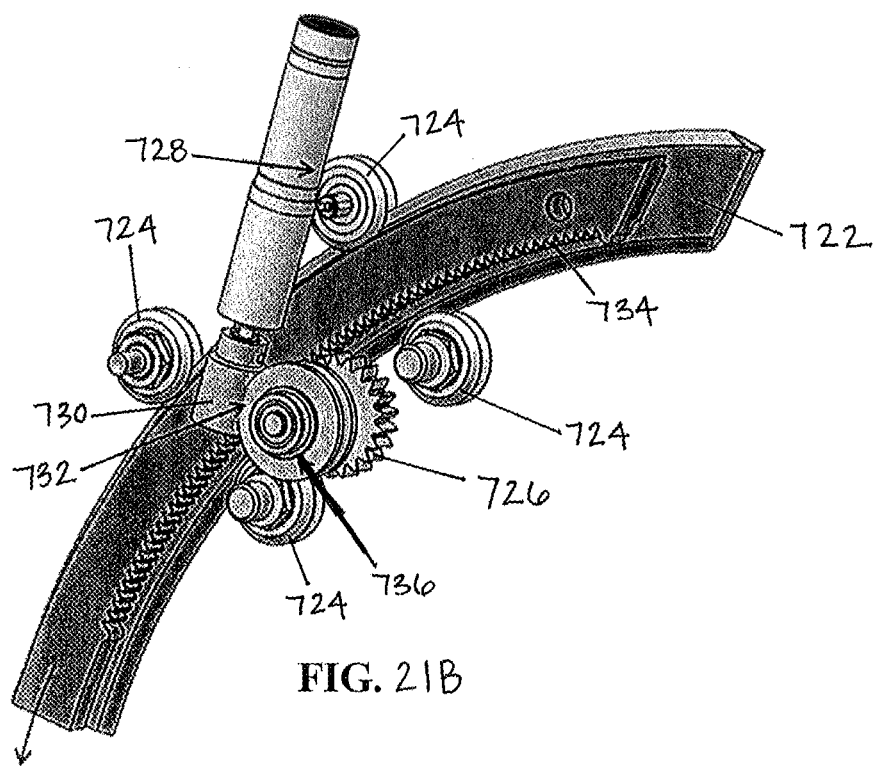
FIG. 21B is a detailed view of the components of the pitch mechanism of FIG. 21A.
Figure 21C:
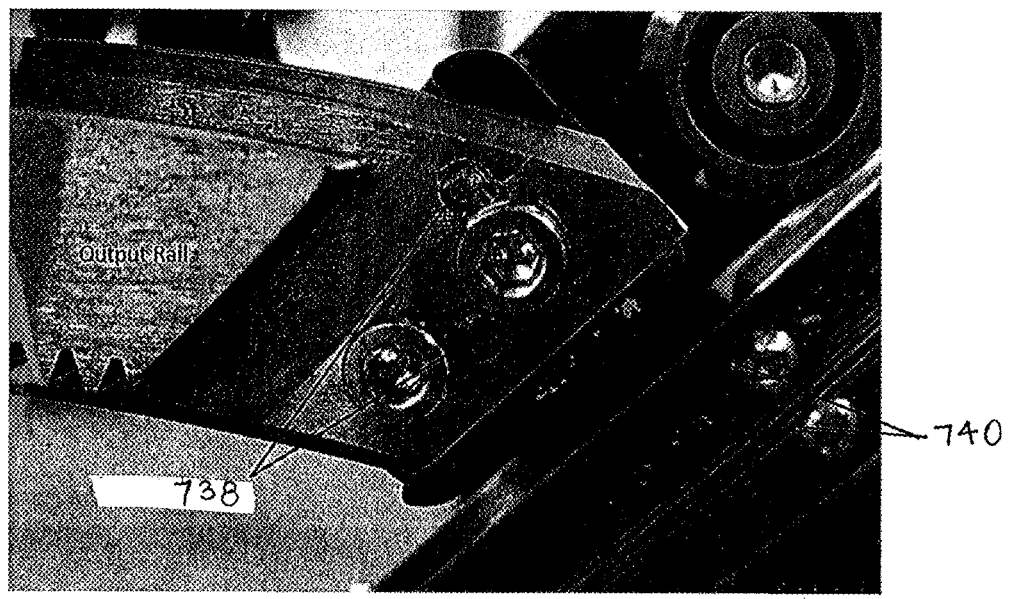
FIG. 21C is a detailed view of the rail of the pitch mechanism connected to a plunge mechanism.

FIGS. 21A-21C depict the internal mechanisms of a pitch joint (such as joint 564 as discussed above), according to one embodiment. More specifically, FIG. 21A depicts a pitch mechanism structure (or "housing") 720 having an output rail 722 slidably coupled to the structure 720 such that the pitch results from movement of the output rail 722 in relation to the structure 720. The output rail 722 is an elongate curved structure 722 that, according to one embodiment, constitutes of segment of a circular arc. Further, the output rail 722 is slidably coupled to the pitch mechanism housing 720 as described below and further is fixedly coupled at one end of the rail 722 to the plunge housing (not shown) such that movement of the rail 722 causes rotation of the plunge housing (and any attached robotic surgical device) about the RCM (not shown).

In one embodiment, the output rail 722 is coupled to the pitch mechanism structure 720 via rotatable bearings 724. In the specific implementation as shown, there are two pairs of bearings 724 that are positioned on either side of the rail 722 such that the rail 722 is in contact with each of the bearings 724 and can move translationally in relation to the bearings 724. Further, as described in additional detail below, the rail 722 is threadably coupled to a rotatable gear 726.

As best shown in FIG. 21B, the output rail 722 is actuated by a motor 728 that is rotatably coupled to the output rail 722 via a series of gears or other rotation elements. The gears include a drive gear 730 that is a worm screw 730 that is rotationally constrained to the motor 728 and threadably/rotatably coupled to a worm wheel 732. The worm wheel 732 is rotationally constrained to the rotatable gear 726, which is threadably coupled to the teeth 734 of the rail 722 such that rotation of the worm wheel 732 causes rotation of the rotatable gear 726 and thus translation of the teeth 734 (and thus the rail 722). In one implementation, the gears provide a total reduction of 12900:1, converting the high-speed motor output to the low speed and high torque required. The shaft containing the worm wheel 732 and the rotatable gear 726 is supported with two bearings 736 on opposing ends of the shaft. In one embodiment, the motor 728, gear train, motor controller (not shown), and cabling (not shown) are housed together in the pitch housing 720. Further, the output rail 722 is fastened to the plunge housing (discussed below) with alignment pins 738 and screws 740, as best shown in FIG. 21C.

Figure 22A:
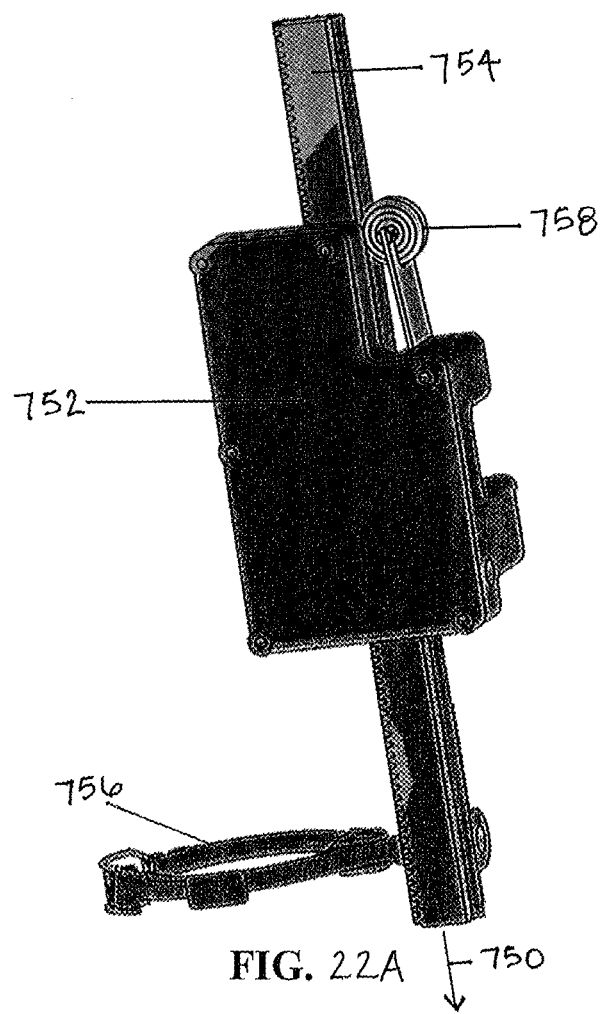
FIG. 22A is a perspective view of a plunge mechanism of a gross positioning system, according to one embodiment.
Figure 22B:
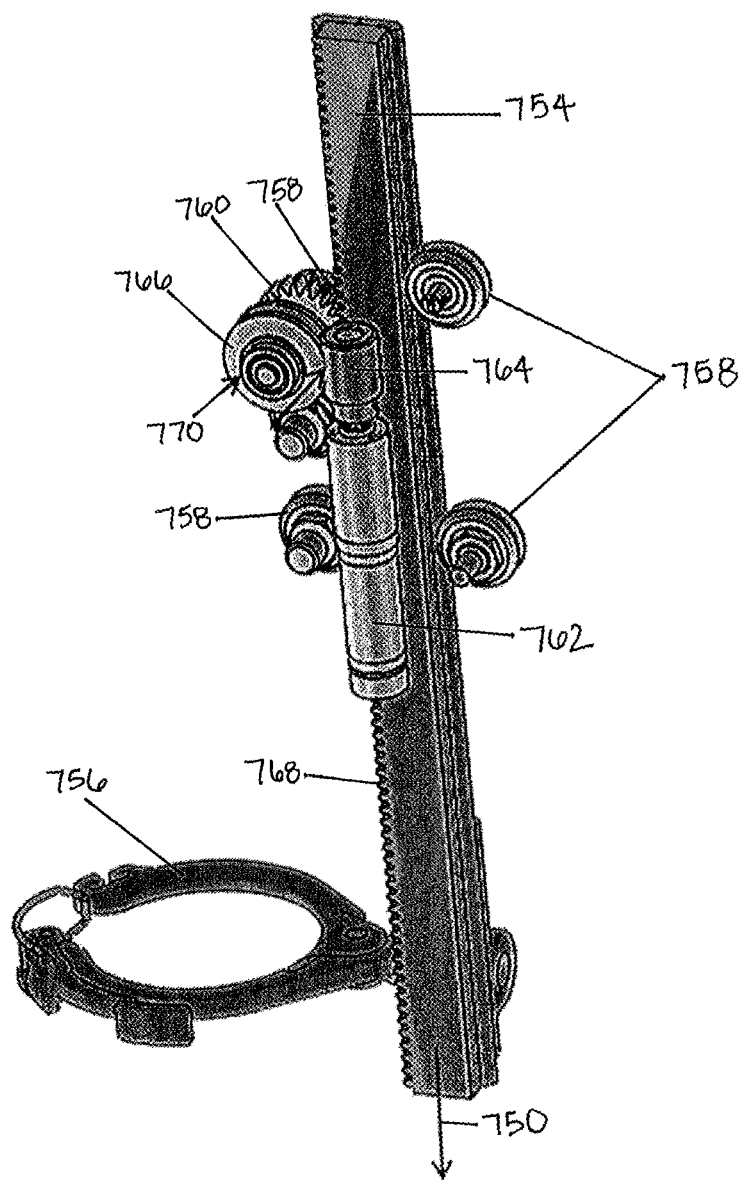
FIG. 22B is a detailed view of the components of the plunge mechanism of FIG. 22A.

FIGS. 22A-22B depict a plunge joint (such as joint 566 as discussed above) 750, according to one embodiment. More specifically, FIG. 22A depicts a plunge mechanism structure (or "housing") 752 having an output rail 754 slidably coupled to the structure 752 such that the plunge or sliding movement results from translational movement of the output rail 754 in relation to the structure 752. The output rail 754 is a substantially straight elongate structure 754 that is slidably coupled to the plunge mechanism housing 752 as described below and further is fixedly coupled at one end of the rail 754 to the robot attachment clamp 756 such that movement of the rail 754 causes movement of any robotic device (not shown) disposed within the clamp 756, thereby translating the robotic device into and out of the port (or incision or opening) at the surgical site.

In one embodiment, the output rail 754 is coupled to the plunge mechanism structure 752 via rotatable bearings 758. In the specific implementation as shown, there are two pairs of bearings 758 that are positioned on either side of the rail 754 such that the rail 754 is in contact with each of the bearings 758 and can move translationally in relation to the bearings 758. Further, as described in additional detail below, the rail 754 is threadably coupled to a rotatable gear 760.

As best shown in FIG. 22B, the output rail 754 is actuated by a motor 762 that is rotatably coupled to the output rail 754 via a series of gears or other rotation elements. The gears include a drive gear 764, for example, a worm screw 764 or other rotatable element, that is rotationally constrained to the motor 762 and threadably/rotatably coupled to a worm wheel 766. The worm wheel 766 is rotationally constrained to the rotatable gear 760, which is threadably coupled to the teeth 768 of the rail 754 such that rotation of the worm wheel 766 causes rotation of the rotatable gear 760 and thus translation of the teeth 768 (and thus the rail 754). In one implementation, the gears provide a total reduction of 840:1, converting the high-speed motor output to the low speed and high torque required. The shaft containing the worm wheel 766 and the rotatable gear 760 is supported with two bearings 770 on opposing ends of the shaft. In one embodiment, the motor 762, gear train, motor controller (not shown), and cabling (not shown) are housed together in the plunge housing 752.

It is understood that alternative versions of these three joints can use any known mechanisms other than gears. For example, each of the joints could be directly driven by a motor. In further alternatives, motion along the rails may not use gears, but may instead simply drive one of the support rollers to produce motion along the rail. In addition, hydraulic, pneumatic, or cable drives could be used in other known designs to produce the desired output motion.

Figure 23:
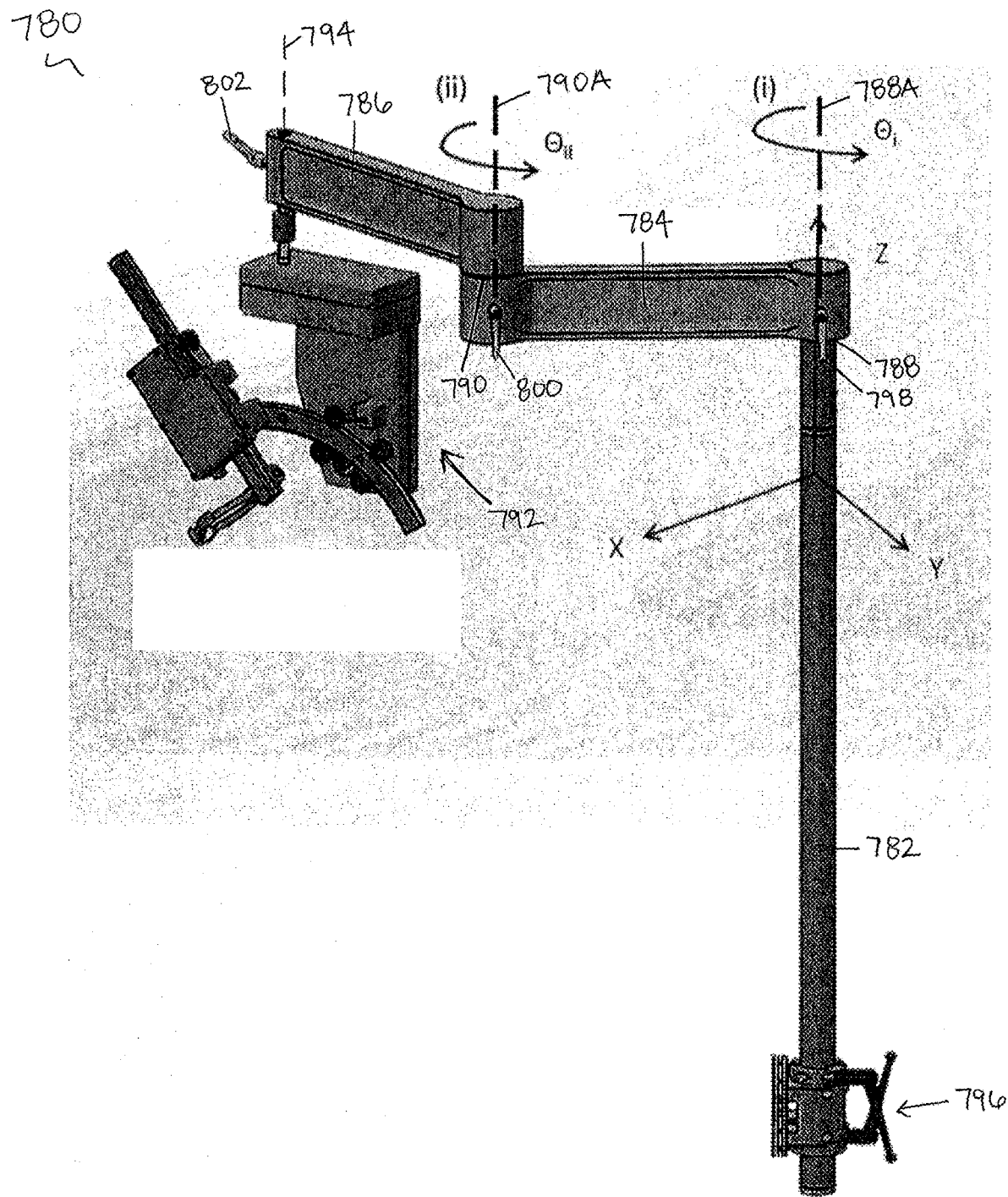
FIG. 23 is a robotic surgical device positioning system, according to one embodiment.

FIG. 23 depicts one embodiment of a robot support arm 780. In this implementation, the support arm 780 has a vertical (or "base") rod 782, a first elongate arm 784 rotatably coupled to the rod 782 at a first rotatable joint 788, and a second elongate arm 786 rotatably coupled to the first arm 784 at a second rotatable joint 790. The first joint 788 has a first axis of rotation 788A, and the second joint 790 has a second axis of rotation 790A such that the two axes of rotation 788A, 790A are vertically parallel. This allows for planar (X/Y directions) positioning of the gross positioning robotic device 792 with respect to the patient. In addition, the yaw axis 794 of the gross positioning robotic device 792 is also vertically parallel to the other two axes of rotation 788A, 790A.

The vertical positioning (Z direction) of the support arm 780 can be adjusted at the bed rail (not shown) using the clamp 796. Once vertical placement has been selected, the gross positioning robotic device 792 can be docked or otherwise attached to the support arm 780. Then the arm 780 can be horizontally positioned as needed, including throughout the robotic surgical device (not shown) insertion process. Once a final position for the robotic surgical device (not shown) has been selected, the gross positioning robotic device 792 is docked with the robotic surgical device (not shown). Typically, this is accomplished by locating the RCM approximately at the port/incision/opening. At this point, the support arm 780 can be locked into position using joint locks 798, 800. Joint lock 802 is used to support the gross positioning robotic device 792 output shaft as noted above.

Figure 24A:
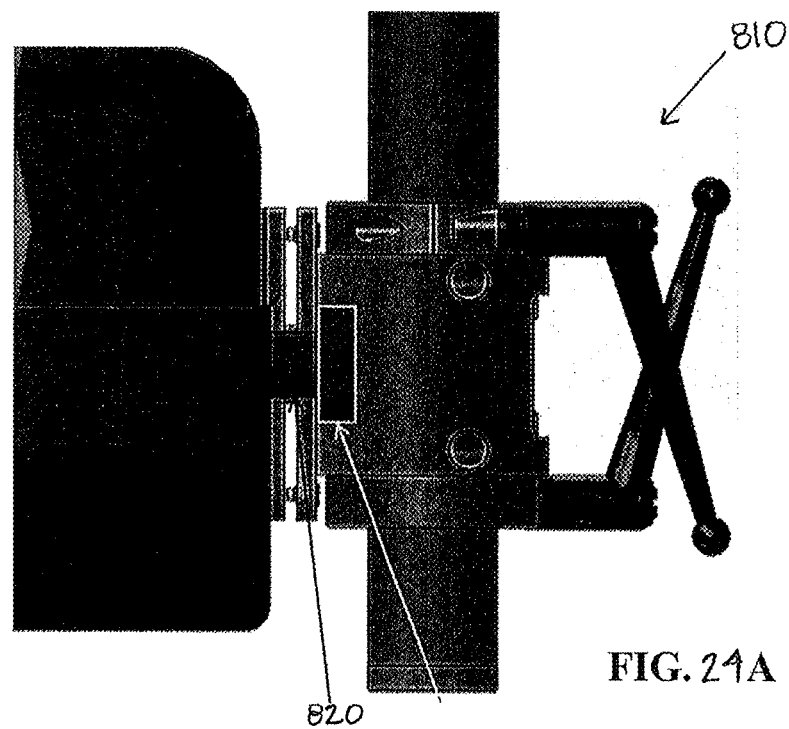
FIG. 24A is a perspective view of a clamping mechanism of a gross positioning system, according to one embodiment.
Figure 24B:
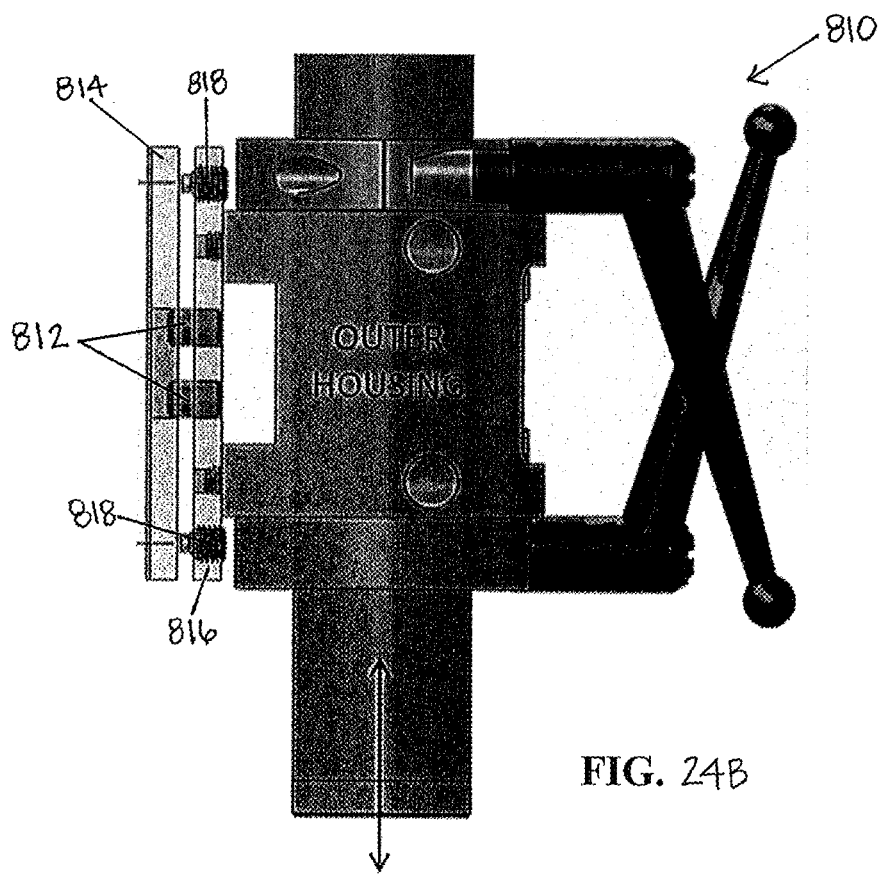
FIG. 24B is a detailed view of the clamping mechanism of FIG. 24A.

In one embodiment, a bed rail clamp 810 (similar to clamp 796) is depicted in FIGS. 24A-24B. Loose or flexible bed rails have the potential to cause large deflections when using bed-mounted support arms, which act as cantilevered beams. To combat this, a robot support arm (such as arm 780) can be fastened to a standard surgical bed rail using the spreading clamp 810. The clamp 810 has two alignment pins 812 that support the back plate 814 and act like linear bearings. The back plate 814 is pushed against the bedside, and the front plate 816 against the bed rail, using four set screws 818. This puts the bed rail mounting bolts 820 in tension, limiting any potential deflection. The outer housing rests on the bed rail and allows for height adjustment of the support arm (such as arm 780).

According to one alternative embodiment, any of the gross positioning robotic device embodiments herein can have an additional feature—laser-aided positioning. More specifically, the gross positioning robotic device 840 embodiment as shown in FIG. 25 has two line lasers 842, 844, with one laser 842 disposed on the plunge housing 846 and one laser 844 disposed on the pitch housing 848. The lasers 842, 844 are positioned and aimed to cause the laser light from each laser 842, 844 to intersect at the RCM 850. Thus, the lasers 842, 844 can help with easy docking and positioning of the gross positioning robotic device 840, and the RCM 850 as shown by the lasers can easily be located at the patient incision/port/opening by the user.

Figure 26A:
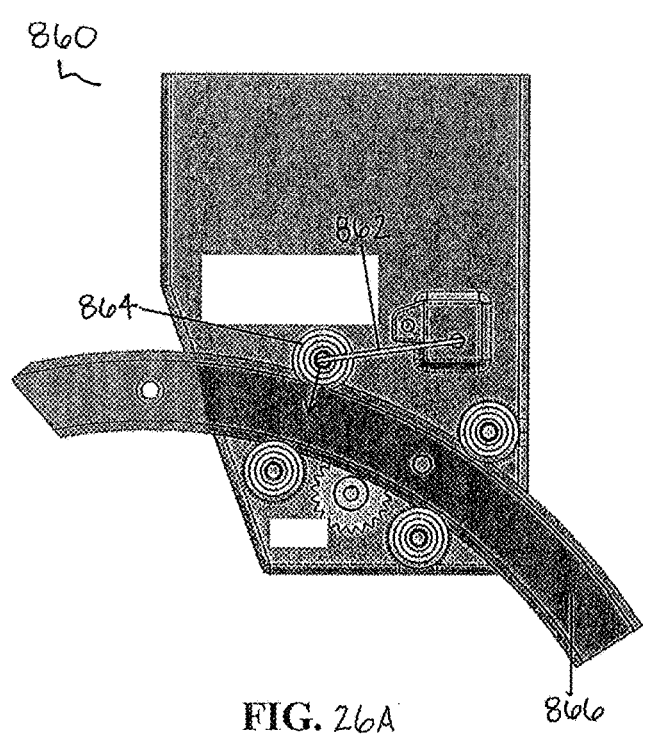
FIG. 26A is a perspective view of a pitch mechanism of a gross positioning system, according to one embodiment.
Figure 26B:
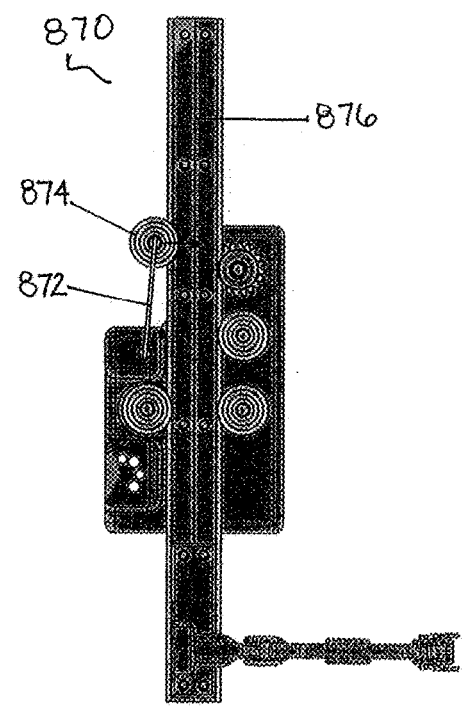
FIG. 26B is a perspective view of a plunge mechanism of a gross positioning system, according to one embodiment.

As shown in FIGS. 26A and 26B, various implementations of the gross positioning device embodiments herein can also include tensioned mechanisms that provide tensioned force applied to at least one bearing of the pitch housing and/or the plunge housing to ensure contact of the bearings with the rails. More specifically, as shown in FIG. 26A, one embodiment of a pitch housing 860 has a leaf spring 862 that applies force to the bearing 864 that urges the bearing 864 into contact with the rail 866. The leaf spring 862 can be manually de-tensioned, removing the bearing 864 from contacting the rail 866. This allows the rail 866 to be disengaged from the pitch housing 860. Then each subcomponent is easily disassembled as needed for cleaning and sterilization. Similarly, as shown in FIG. 26B, one embodiment of a plunge housing 870 has a leaf spring 872 that applies force to the bearing 874 that urges the bearing 874 into contact with the rail 876. The leaf spring 872 can be manually de-tensioned, removing the bearing 874 from contacting the rail 876. This allows the rail 876 to be disengaged from the pitch housing 870. Then each subcomponent is easily disassembled as needed for cleaning and sterilization. It is understood that any known tensioning mechanism can be used in place of the leaf springs.

In a further alternative embodiment, any gross positioning robotic device as disclosed or contemplated herein can be controlled at the bedside using a local interface, such as a button or a joystick (not shown), to drive each joint independently. The user can jog each joint individually or simultaneously with the interface. The gross positioning robotic device can be set aside while the robotic surgical device is inserted and then easily be introduced for docking when needed with this function. The interface can be intuitive, with the button or joystick articulation direction corresponding to the drive direction. To achieve this, the user interface can be localized at each joint or can be centrally located. For robot extraction, the robotic surgical device can be un-docked, and the gross positioning robotic device can be jogged out of the way.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

Although the various embodiments have been described with reference to preferred implementations, persons skilled in the art will recognize that changes may be made in form and detail without departing from the spirit and scope thereof.

What is claimed is:

1. A gross positioning system for use with a robotic surgical device, the system comprising:
   (a) a positioning body;
   (b) a yaw mechanism operably coupled to the positioning body at a first rotational joint;
   (c) a pitch mechanism operably coupled to the positioning body at a second rotational joint; and
   (d) a plunge mechanism slidably coupled to the pitch mechanism such that the plunge mechanism can move along a length of a plunge axis, wherein the plunge mechanism is configured to be coupleable to the robotic surgical device;
   wherein the yaw mechanism is configured to rotate the robotic surgical device about an incision without changing a pitch angle or plunge distance of the robotic surgical device with respect to the incision.

2. The gross positioning system of claim 1, wherein the yaw mechanism further comprises a motor operably engaged with an output shaft configured to rotate the positioning body around the first rotational joint.

3. The gross positioning system of claim 2, wherein the yaw mechanism further comprises:
   (a) a drive gear coupled to the motor;
   (b) a driven gear operably engaged with the drive gear;
   (c) a screw coupled to the driven gear; and
   (d) a wheel is coupled to the output shaft, wherein the wheel is operably engaged with the screw.

4. The gross positioning system of claim 1, wherein the pitch mechanism further comprises a motor operably engaged with a curved output rail configured to rotate the plunge mechanism around the second rotational joint.

5. The gross positioning system of claim 4, wherein the pitch mechanism further comprises:
   (a) a screw coupled to the motor;
   (b) a wheel operably engaged with the screw; and
   (c) a rotatable gear operably coupled to the wheel, wherein the rotatable gear is operably engaged with the curved output rail.

6. The gross positioning system of claim 1, wherein the plunge mechanism further comprises a motor operably engaged with an elongate output rail configured to translationally move the plunge mechanism along the plunge axis.

7. The gross positioning system of claim 1, wherein the plunge mechanism further comprises a clamp configured to be coupleable to the robotic surgical device.

8. The gross positioning system of claim 1, wherein a first axis of rotation of the first rotational joint, a second axis of rotation of the second rotational joint, and the plunge axis intersect at a single point of intersection.

9. The gross positioning system of claim 8, further comprising two or more lasers configured to emit light beams intersecting at the single point of intersection.

10. The gross positioning system of claim 1, further comprising a controller operably coupled to the gross positioning system and the robotic surgical device, wherein the gross positioning system and robotic surgical device are configured to operate together to position the robotic surgical device within a body cavity of a patient.

11. A gross positioning system for use with a robotic surgical device, the system comprising:
   (a) a positioning body;
   (b) a yaw mechanism operably coupled to the positioning body at a first rotational joint;
   (c) a pitch mechanism operably coupled to the positioning body at a second rotational joint;
   (d) a plunge mechanism slidably coupled to the pitch mechanism such that the plunge mechanism can move along a length of a plunge axis, wherein the plunge mechanism is configured to translationally move the robotic surgical device along the length of the plunge axis; and
   (e) the robotic surgical device operably coupled to the plunge mechanism, the robotic surgical device comprising:
      (i) a device body; and
      (ii) an arm operably coupled to the device body, the arm comprising an end effector,
   wherein the robotic surgical device is positionable through an insertion point in a patient such that the arm and at least a portion of the device body is positionable within a body cavity of the patient at a desired yaw angle, pitch angle, and plunge depth, and wherein the yaw mechanism is configured to change the yaw angle without changing the pitch angle and plunge depth.

12. The gross positioning system of claim 11, wherein a first axis of rotation of the first rotational joint, a second axis of rotation of the second rotational joint, and the plunge axis intersect at a single point of intersection.

13. The gross positioning system of claim 12, wherein the single point of intersection is disposed at some point along a portion of the robotic surgical device.

14. The gross positioning system of claim 12, wherein the single point of intersection is disposed at an insertion point of a patient and the arm is partially disposed through the single point of intersection.

15. The gross positioning system of claim 14, wherein the insertion point comprises an incision or a natural orifice.

16. An external gross positioning system for use with an internal robotic surgical device, the system comprising:
   (a) a support arm;
   (b) a positioning body operably coupled to the support arm;
   (c) a yaw mechanism operably coupled to the positioning body at a first rotational joint;
   (d) a pitch mechanism operably coupled to the positioning body at a second rotational joint;
   (e) a plunge mechanism slidably coupled to the pitch mechanism such that the plunge mechanism can move along a length of a plunge axis, wherein the plunge mechanism is configured to be coupleable to the internal robotic surgical device; and
   (f) a single point of intersection of an axis of rotation of the first rotational joint, an axis of rotation of the second rotational joint, and the plunge axis:

wherein yaw mechanism rotates the positioning body about the single point of intersection without changing an angle of the second axis of rotation and a plunge depth of the positioning body with respect to the single point intersection.

17. The external gross positioning system of claim 16, wherein the support arm further comprises:
   (a) a clamp configured to couple with a bed rail;
   (b) a rod coupled to the clamp;
   (c) a first elongate arm operably coupled to the rod at a third rotational joint; and
   (d) a second elongate arm operably coupled to the first elongate arm at a fourth rotational joint and operably coupled to the positioning body at a fifth rotational joint.

18. The external gross positioning system of claim 17, wherein the third rotational joint, the fourth rotational joint, and the fifth rotational joint are each configured to rotate around parallel axes.

19. The external gross positioning system of claim 16, wherein the robotic surgical device comprises at least one arm, wherein the external gross positioning system and robotic surgical device are configured to operate together to position the robotic surgical device within a body cavity of a patient.

20. The external gross positioning system of claim 19, further comprising:
   (a) a central processing unit operably coupled to the external gross positioning system and the robotic surgical device, wherein the central processing unit comprises software configured to transmit control instructions to the external gross positioning system and the robotic surgical device; and
   (b) a controller operably coupled to the central processing unit.

* * * * *